(12) United States Patent
Bendels et al.

(10) Patent No.: US 9,505,762 B2
(45) Date of Patent: Nov. 29, 2016

(54) PURINE DERIVATIVES AS CB2 RECEPTOR AGONISTS

(71) Applicant: Hoffmann-La Roche Inc., Little Falls, NJ (US)

(72) Inventors: Stefanie Bendels, Riehen (CH); Uwe Grether, Efringen-Kirchen (DE); Atsushi Kimbara, Shizuoka (JP); Matthias Nettekoven, Grenzach-Wyhlen (DE); Stephan Roever, Inzlingen (DE); Mark Rogers-Evans, Bottmingen (CH); Tanja Schulz-Gasch, Ziefen (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/923,177

(22) Filed: Oct. 26, 2015

(65) Prior Publication Data

US 2016/0046631 A1    Feb. 18, 2016

Related U.S. Application Data

(63) Continuation of application No. PCT/EP2014/058545, filed on Apr. 28, 2014.

(30) Foreign Application Priority Data

May 2, 2013 (EP) .................... 13166293

(51) Int. Cl.
| | | |
|---|---|---|
| C07D 473/34 | (2006.01) | |
| C07D 473/16 | (2006.01) | |
| C07D 473/18 | (2006.01) | |
| C07D 519/00 | (2006.01) | |

(52) U.S. Cl.
    CPC .......... C07D 473/34 (2013.01); C07D 473/16 (2013.01); C07D 473/18 (2013.01); C07D 519/00 (2013.01)

(58) Field of Classification Search
    None
    See application file for complete search history.

(56) References Cited

U.S. PATENT DOCUMENTS 5,057,517 A * 10/1991 Johnston .............. C07D 471/04
                                                    514/252.16
2012/0316147 A1    12/2012 Bissantz

FOREIGN PATENT DOCUMENTS

| WO | 01/58869 A2 | 8/2001 |
|---|---|---|
| WO | 03/082191 A2 | 10/2003 |
| WO | 03/093269 A2 | 11/2003 |
| WO | 2004/037823 A1 | 5/2004 |
| WO | 2006/047516 A2 | 5/2006 |
| WO | 2009/051705 A1 | 4/2009 |
| WO | 2010/019762 A1 | 2/2010 |
| WO | 2010/118367 A2 | 10/2010 |
| WO | 2013/068306 A1 | 5/2013 |
| WO | 2014/005968 A1 | 1/2014 |
| WO | 2014/086705 A1 | 6/2014 |
| WO | 2014/086805 A1 | 6/2014 |
| WO | 2014/086806 A1 | 6/2014 |
| WO | 2014/086807 | 6/2014 |
| WO | 2014/135507 A1 | 9/2014 |

OTHER PUBLICATIONS

Pertwee, Roger. British Journal of Pharmacology (2009), 156, 397-411.*
WebMD. Chronic Pain-Prevention. (2014) Web <http://www.webmd.com/pain-management/tc/chronic-pain-prevention>.*
Qu, Gui-Rong. Green Chem., 2008, 10, 287-289.*
(Database Registry (Online) Chemical Abstracts Service, Columbus, Ohio, US, Qu Gui-Rong et al 'Microwave assisted rapid synthesis of 6-(1-pyrrolidinyl)purine and its derivatives', XP002724678 retrieved from STN Database accession No. 2008:1015363 abstract & Henan Shifan Daxue Xuebao, Ziran Kexueban (2008), 36(3), 145-147 Coden: Hesker; ISSN: 1000-2367, 2008).
(Database Registry (Online) Chemical Abstracts Service, Columbus, Ohio, US; Aug. 31, 2007, '1-[2-chloro-9-(1-methylethyl)-9H-purin-6-yl]-3-pyrrolidinol', XP002724679, retrieved from STN Database accession No. 945895-33-0 abstract).
Cheng et al., "Potential Purine Antagonists VII. Synthesis of 6-Alkylpyrazolo[3,4-d]pyrimidines" Journal of Organic Chemistry 23:191-200 ( 1958).
Cheng et al., "Potential Purine Antagonists. XII. Synthesis of 1-Alkyl(aryl)-4,6-disubstituted Pyra~olo(3,4-d]pyrimidines" Journal of Organic Chemistry 23:852-861 ( 1958).

(Continued)

*Primary Examiner* — Golam M M Shameem
*Assistant Examiner* — Laura Daniel
(74) *Attorney, Agent, or Firm* — Alex Andrus

(57) ABSTRACT

The invention relates to a compound of formula (I)

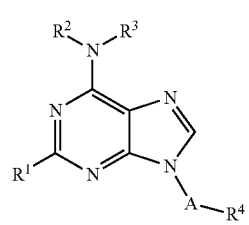

wherein A and $R^1$ to $R^4$ are defined as in the description and in the claims. The compound of formula (I) can be used as a medicament.

13 Claims, No Drawings

(56) References Cited

OTHER PUBLICATIONS

ISR for PCT/EP2014/058545, Dated Nov. 6, 2014.
Nettekoven et al., "Highly potent and selective cannabinoid receptor 2 agonists: initial hit optimization of an adamantyl hit series identified from high-through-put screening" Bioorg Med Chem Lett. 23(5):1177-81 ( 2013).
Nettekoven et al., "Novel Triazolopyrimidine-Derived Cannabinoid Receptor 2 Agonists as Potential Treatment for Inflammatory Kidney Diseases" ChemMedChem. 11(2):179-89 ( 2016).
Senga et al., "Synthesis and Xanthine Oxidase Inhibitory Activity of 4,6-Disubstituted 1-p-Chlorophenylpyrazolo[3,4-d]pyrimidines" Journal of Hererocyclic Chemistry 19(6):1565-67 ( 1982).
Slavik et al., "Discovery of a high affinity and selective pyridine analog as a potential positron emission tomography imaging agent for cannabinoid type 2 receptor" J Med Chem. 58(10):4266-77 ( 2015).

\* cited by examiner

PURINE DERIVATIVES AS CB2 RECEPTOR AGONISTS

CROSS REFERENCE TO RELATED APPLICATIONS

This application is a continuation of International Application No. PCT/EP2014/058545 having an International Filing Date of 28 Apr. 2014, the entire contents of which are incorporated herein by reference, and which claims the benefit of priority under 35 U.S.C. §119 to EP 13166293.4, filed 2 May 2013.

FIELD OF THE INVENTION

The present invention relates to organic compounds useful for therapy and/or prophylaxis in a mammal, and in particular to compounds that are preferential agonists of the Cannabinoid Receptor 2.

SUMMARY OF THE INVENTION

The invention relates in particular to a compound of formula (I)

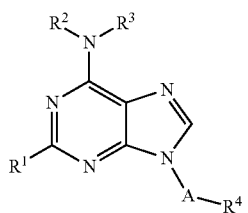

wherein
A is $CH_2$, $CH_2CH_2$, $CH_2CO$ or absent;
$R^1$ is tert.-butyl, tert.-butylamino, 2,2-dimethylpropyloxy or halogen;
$R^2$ and $R^3$, together with the nitrogen atom to which they are attached, form pyrrolidinyl, substituted pyrrolidinyl, thiazolidinyl, alkylpiperazinyl, 2-oxa-7-azaspiro[3.4]octyl, 2-oxa-6-azaspiro[3.3]heptyl, azetidinyl, substituted azetidinyl, 2,2-dioxo-$2\lambda^6$-thia-6-azaspiro[3.3]heptyl or halo-5-azaspiro[2.4]heptyl, wherein substituted pyrrolidinyl is pyrrolidinyl substituted with one to four substituents independently selected from halogen, hydroxyl, alkyl, hydroxyalkyl, cyano, alkylcarbonylamino, alkylcarbonyloxy and haloalkyl and wherein substituted azetidinyl is azetidinyl substituted with one or two substituents selected from halogen, hydroxyl, alkyl and haloalkyl; and
$R^4$ is hydrogen, phenyl, halophenyl, alkylphenyl, haloalkylphenyl, pyridinyl, halopyridinyl, cycloalykl, alkyl, alkyloxadiazolyl, oxolanyl, alkyltetrazolyl, alkoxy, alkylsulfonylphenyl, haloalkyl, alkoxyphenyl, dioxothietanyl, cycloalkyltetrazolyl, haloalkyl-1H-pyrazolyl or cycloalkylalkyltetrazolyl;
or a pharmaceutically acceptable salt or ester thereof.

The compound of formula (I) is particularly useful in the treatment or prophylaxis of e.g. pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis.

The compound of formula (I) is in particular useful in the treatment or prophylaxis of diabetic retinopathy, retinal vein occlusion or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in pre-conditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

DEFINITIONS

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. A particular example of alkyl is methyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular examples of "cycloalkyl" are cyclopropyl and cyclohexyl, in particular cyclohexyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy. A particular "alkoxy" is methoxy.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. Particular "halogen" are fluorine and chlorine. In the definition of $R^2$ and $R^3$, fluorine is a particular halogen.

The term "haloalkyl", alone or in combination, denotes an alkyl group substituted with at least one halogen, particularly substituted with one to five halogens, particularly one to three halogens. A particular "haloalkyl" is trifluoromethyl.

The terms "hydroxyl" and "hydroxy", alone or in combination, signify the —OH group.

The term "carbonyl", alone or in combination, signifies the —C(O)— group.

The term "oxy", alone or in combination, signifies the —O— group.

The term "amino", alone or in combination, signifies the primary amino group (—$NH_2$), the secondary amino group (—NH—), or the tertiary amino group (—N—). A particular amino is —NH—.

The term "aminocarbonyl", alone or in combination, signifies the $NH_2$—C(O)—, —NH—C(O)— or —N—C(O)— group.

The term "carbonylamino", alone or in combination, signifies the —C(O)—NH— or —C(O)—N— group. A particular carbonylamino is —C(O)—N—.

The term "sulfonyl", alone or in combination, signifies the —$S(O)_2$— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, $3^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

DETAILED DESCRIPTION OF EXEMPLARY EMBODIMENTS

The invention is directed in particular to a compound of formula (I) wherein:
A is $CH_2$, $CH_2CH_2$, $CH_2CO$ or absent;
$R^1$ is tert.-butyl, tert.-butylamino or 2,2-dimethylpropyloxy;
$R^2$ and $R^3$, together with the nitrogen atom to which they are attached, form pyrrolidinyl, substituted pyrrolidinyl, thiazolidinyl, alkylpiperazinyl, 2-oxa-7-azaspiro[3.4]octyl or 2-oxa-6-azaspiro[3.3]heptyl, wherein substituted pyrrolidinyl is pyrrolidinyl substituted with one to four substituents independently selected from halogen, hydroxyl, alkyl, hydroxyalkyl, cyano and alkylcarbonylamino; and
$R^4$ is phenyl, halophenyl, alkylphenyl, haloalkylphenyl, pyridinyl, halopyridinyl, cycloalkyl, alkyl, alkyloxadiazolyl, oxolanyl, alkyltetrazolyl, alkoxy, alkylsulfonylphenyl, haloalkyl, alkoxyphenyl, dioxothietanyl, cycloalkyltetrazolyl or haloalkyl-1H-pyrazolyl;
or a pharmaceutically acceptable salt or ester thereof.
The invention further relates in particular to:
A compound of formula (I) wherein A is $CH_2$;
A compound of formula (I) wherein $R^1$ is tert.-butyl or 2,2-dimethylpropyloxy;
A compound of formula (I) wherein $R^1$ is tert.-butyl;

A compound of formula (I) wherein $R^2$ and $R^3$, together with the nitrogen atom to which they are attached, form thiazolidinyl, substituted pyrrolidinyl or substituted azetidinyl, wherein substituted pyrrolidinyl is pyrrolidinyl substituted with one or two substituents independently selected from halogen, hydroxyl, hydroxyalkyl and cyano and wherein substituted azetidinyl is azetidinyl substituted with one or two substituents selected from halogen, hydroxyl and haloalkyl;

A compound of formula (I) wherein $R^2$ and $R^3$, together with the nitrogen atom to which they are attached, form thiazolidinyl, substituted pyrrolidinyl or substituted azetidinyl, wherein substituted pyrrolidinyl is pyrrolidinyl substituted with one or two substituents independently selected from fluorine, hydroxyl, hydroxymethyl and cyano and wherein substituted azetidinyl is azetidinyl substituted with one or two substituents selected from fluoro, hydroxyl and trifluoromethyl;

A compound of formula (I) wherein $R^2$ and $R^3$, together with the nitrogen atom to which they are attached, form thiazolidinyl, difluoropyrrolidinyl, hydroxypyrrolidinyl, hydroxymethylpyrrolidinyl, cyanopyrrolidinyl, difluoroazetidinyl or (hydroxyl)(trifluoromethyl)azetidinyl;

A compound of formula (I) wherein $R^2$ and $R^3$, together with the nitrogen atom to which they are attached, form substituted pyrrolidinyl, wherein substituted pyrrolidinyl is pyrrolidinyl substituted with one or two substituents independently selected from halogen and hydroxyl;

A compound of formula (I) wherein $R^2$ and $R^3$, together with the nitrogen atom to which they are attached, form substituted pyrrolidinyl, wherein substituted pyrrolidinyl is pyrrolidinyl substituted with one or two substituents independently selected from fluorine and hydroxyl;

A compound of formula (I) wherein $R^2$ and $R^3$, together with the nitrogen atom to which they are attached, form difluoropyrrolidinyl or hydroxypyrrolidinyl;

A compound of formula (I) wherein $R^2$ and $R^3$, together with the nitrogen atom to which they are attached, form difluoropyrrolidinyl, hydroxypyrrolidinyl, tetrafluoropyrrolidinyl, methylcarbonylamino, thiazolidinyl, methylpiperazinyl, 2-oxa-7-azaspiro[3.4]octyl or 2-oxa-6-azaspiro[3.3]heptyl, (methyl)(hydroxyl)pyrrolidinyl, hyydroxyalkylpyrrolidinyl or cyanopyrrolidinyl;

A compound of formula (I) wherein $R^4$ is halophenyl, haloalkylphenyl, halopyridinyl, oxolanyl, alkylsulfonylphenyl, pyridinyl or cycloalkyltetrazolyl;

A compound of formula (I) wherein $R^4$ is chlorophenyl, chlorofluorophenyl, trifluoromethylphenyl, chloropyridinyl, oxolanyl, methylsulfonylphenyl, pyridinyl or cyclopropyltetrazolyl;

A compound of formula (I) wherein $R^4$ is halophenyl, haloalkylphenyl, halopyridinyl, oxolanyl, alkylsulfonylphenyl or pyridinyl;

A compound of formula (I) wherein $R^4$ is chlorophenyl, chlorofluorophenyl, trifluoromethylphenyl, chloropyridinyl, oxolanyl, methylsulfonylphenyl or pyridinyl; and A compound of formula (I) wherein $R^4$ is phenyl, chlorophenyl, chlorofluorophenyl, methylphenyl, trifluoromethylphenyl, chloropyridinyl, oxolanyl, methylsulfonylphenyl, pyridinyl, mehtyloxadiazolyl, cyclohexyl, methyl, oxolanyl, methyltetrazolyl, methoxy, trifluoromethyl, methoxyphenyl, thietanyl, trifluoromethyl-1H-pyrazolyl or cyclopropyltetrazolyl.

The invention further relates to a compound of formula (I) selected from:
2-tert-butyl-9-[(4-chlorophenyl)methyl]-6-(3,3-difluoropyrrolidin-1-yl)purine;

2-tert-butyl-9-[(2-chlorophenyl)methyl]-6-(3,3-difluoropyr-rolidin-1-yl)purine;
2-tert-butyl-6-(3,3-difluoropyrrolidin-1-yl)-9-[(4-methyl-phenyl)methyl]purine;
2-tert-butyl-9-[(2-chloro-4-fluorophenyl)methyl]-6-(3,3-di-fluoropyrrolidin-1-yl)purine;
2-tert-butyl-6-(3,3-difluoropyrrolidin-1-yl)-9-[[2-(trifluo-romethyl)phenyl]methyl]purine;
2-tert-butyl-9-[(2-chloropyridin-3-yl)methyl]-6-(3,3-difluo-ropyrrolidin-1-yl)purine;
5-[[2-tert-butyl-6-(3,3-difluoropyrrolidin-1-yl)purin-9-yl] methyl]-3-methyl-1,2,4-oxadiazole;
2-tert-butyl-9-(cyclohexylmethyl)-6-(3,3-difluoropyrroli-din-1-yl)purine;
2-tert-butyl-6-(3,3-difluoropyrrolidin-1-yl)-9-ethylpurine;
2-tert-butyl-6-(3,3-difluoropyrrolidin-1-yl)-9-propylpurine;
2-[[2-tert-butyl-6-(3,3-difluoropyrrolidin-1-yl)purin-9-yl] methyl]-5-methyl-1,3,4-oxadiazole;
2-tert-butyl-6-(3,3-difluoropyrrolidin-1-yl)-9-(oxolan-3-yl) purine;
2-tert-butyl-6-(3,3-difluoropyrrolidin-1-yl)-9-(2-phenyl-ethyl)purine;
2-tert-butyl-6-(3,3-difluoropyrrolidin-1-yl)-9-[(1-methyltet-razol-5-yl)methyl]purine;
2-tert-butyl-6-(3,3-difluoropyrrolidin-1-yl)-9-(2-methoxy-ethyl)purine;
3-[[2-tert-butyl-6-(3,3-difluoropyrrolidin-1-yl)purin-9-yl] methyl]-4-methyl-1,2,5-oxadiazole;
2-[2-tert-butyl-6-(3,3-difluoropyrrolidin-1-yl)purin-9-yl]-1-(2-chlorophenyl)ethanone;
2-tert-butyl-6-(3,3-difluoropyrrolidin-1-yl)-9-[(2-methyl-sulfonylphenyl)methyl]purine;
2-tert-butyl-6-(3,3-difluoropyrrolidin-1-yl)-9-(3,3,3-trifluo-ropropyl)purine;
2-tert-butyl-6-(3,3-difluoropyrrolidin-1-yl)-9-[(4-methoxy-phenyl)methyl]purine;
2-tert-butyl-9-[(3-chloropyridin-2-yl)methyl]-6-(3,3-difluo-ropyrrolidin-1-yl)purine;
1-[2-tert-butyl-9-[(2-chlorophenyl)methyl]purin-6-yl]pyrro-lidin-3-ol;
2-tert-butyl-6-(3,3-difluoropyrrolidin-1-yl)-9-(2-pyridin-3-ylethyl)purine;
2-[2-tert-butyl-6-(3,3-difluoropyrrolidin-1-yl)purin-9-yl]-1-pyridin-2-ylethanone;
1-[2-tert-butyl-9-[(3-chlorophenyl)methyl]purin-6-yl]pyrro-lidin-3-ol;
1-[2-tert-butyl-9-[(4-chlorophenyl)methyl]purin-6-yl]pyrro-lidin-3-ol;
3-[2-tert-butyl-6-(3,3-difluoropyrrolidin-1-yl)purin-9-yl] thietane 1,1-dioxide;
1-[2-tert-butyl-9-[[2-(trifluoromethyl)phenyl]methyl]purin-6-yl]pyrrolidin-3-ol;
1-[2-tert-butyl-9-[(3-methyl-1,2,4-oxadiazol-5-yl)methyl] purin-6-yl]pyrrolidin-3-ol;
1-[2-tert-butyl-9-[(1-methyltetrazol-5-yl)methyl]purin-6-yl] pyrrolidin-3-ol;
1-[2-tert-butyl-9-[(4-methoxyphenyl)methyl]purin-6-yl] pyrrolidin-3-ol;
1-[2-tert-butyl-9-[(3-chloropyridin-2-yl)methyl]purin-6-yl] pyrrolidin-3-ol;
1-[2-tert-butyl-9-[(2-chloropyridin-3-yl)methyl]purin-6-yl] pyrrolidin-3-ol;
1-[2-tert-butyl-9-[(2-methylsulfonylphenyl)methyl]purin-6-yl]pyrrolidin-3-ol;
1-(2-tert-butyl-9-ethylpurin-6-yl)pyrrolidin-3-ol;
1-(2-tert-butyl-9-propylpurin-6-yl)pyrrolidin-3-ol;
1-[2-tert-butyl-9-(2-methoxyethyl)purin-6-yl]pyrrolidin-3-ol;
1-[2-tert-butyl-9-(2-phenylethyl)purin-6-yl]pyrrolidin-3-ol;
1-[2-tert-butyl-9-[(4-methylphenyl)methyl]purin-6-yl]pyr-rolidin-3-ol;
1-[2-tert-butyl-9-(cyclohexylmethyl)purin-6-yl]pyrrolidin-3-ol;
2-tert-butyl-6-(3,3-difluoropyrrolidin-1-yl)-9-[[3-(trifluo-romethyl)-1H-pyrazol-4-yl]methyl]purine;
1-[2-tert-butyl-9-[(2-chloro-4-fluorophenyl)methyl]purin-6-yl]pyrrolidin-3-ol;
1-[2-tert-butyl-9-[(4-methyl-1,2,5-oxadiazol-3-yl)methyl] purin-6-yl]pyrrolidin-3-ol;
1-[2-tert-butyl-9-[[3-(trifluoromethyl)-1H-pyrazol-4-yl] methyl]purin-6-yl]pyrrolidin-3-ol;
1-[2-tert-butyl-9-(3,3,3-trifluoropropyl)purin-6-yl]pyrroli-din-3-ol;
1-[2-tert-butyl-9-(oxolan-3-yl)purin-6-yl]pyrrolidin-3-ol;
2-[2-tert-butyl-6-(3-hydroxypyrrolidin-1-yl)purin-9-yl]-1-(2-chlorophenyl)ethanone;
N—{(S)-1-[2-tert-Butyl-9-(2-chloro-benzyl)-9H-purin-6-yl]-pyrrolidin-3-yl}-acetamide;
N—[(S)-1-[2-tert-butyl-9-[(3-chlorophenyl)methyl]purin-6-yl]pyrrolidin-3-yl]acetamide;
N—[(S)-1-[2-tert-butyl-9-[(4-chlorophenyl)methyl]purin-6-yl]pyrrolidin-3-yl]acetamide;
N—[(S)-1-[2-tert-butyl-9-[[2-(trifluoromethyl)phenyl] methyl]purin-6-yl]pyrrolidin-3-yl]acetamide;
N—[(S)-1-[2-tert-butyl-9-[(2-methylsulfonylphenyl) methyl]purin-6-yl]pyrrolidin-3-yl]acetamide;
N—[(S)-1-[2-tert-butyl-9-[(2-chloropyridin-3-yl)methyl] purin-6-yl]pyrrolidin-3-yl]acetamide;
N—[(S)-1-[2-tert-butyl-9-[(3-chloropyridin-2-yl)methyl] purin-6-yl]pyrrolidin-3-yl]acetamide
N—[(S)-1-[2-tert-butyl-9-[(4-methyl-1,2,5-oxadiazol-3-yl) methyl]purin-6-yl]pyrrolidin-3-yl]acetamide;
7-[2-tert-butyl-9-[(2-chlorophenyl)methyl]purin-6-yl]-2-oxa-7-azaspiro[3.4]octane;
7-[2-tert-butyl-9-[(3-chlorophenyl)methyl]purin-6-yl]-2-oxa-7-azaspiro[3.4]octane;
7-[2-tert-butyl-9-[(4-chlorophenyl)methyl]purin-6-yl]-2-oxa-7-azaspiro[3.4]octane;
7-[2-tert-butyl-9-[[2-(trifluoromethyl)phenyl]methyl]purin-6-yl]-2-oxa-7-azaspiro[3.4]octane;
7-[2-tert-butyl-9-[(2-methylsulfonylphenyl)methyl]purin-6-yl]-2-oxa-7-azaspiro[3.4]octane;
7-[2-tert-butyl-9-[(2-chloropyridin-3-yl)methyl]purin-6-yl]-2-oxa-7-azaspiro[3.4]octane;
7-[2-tert-butyl-9-[(4-methyl-1,2,5-oxadiazol-3-yl)methyl] purin-6-yl]-2-oxa-7-azaspiro[3.4]octane;
7-[2-tert-butyl-9-(2-methoxyethyl)purin-6-yl]-2-oxa-7-azaspiro[3.4]octane;
1-[2-tert-butyl-9-[(2-chlorophenyl)methyl]purin-6-yl]-3-methylpyrrolidin-3-ol;
1-[2-tert-butyl-9-[(3-chlorophenyl)methyl]purin-6-yl]-3-methylpyrrolidin-3-ol;
1-[2-tert-butyl-9-[(4-chlorophenyl)methyl]purin-6-yl]-3-methylpyrrolidin-3-ol;
1-[2-tert-butyl-9-[[2-(trifluoromethyl)phenyl]methyl]purin-6-yl]-3-methylpyrrolidin-3-ol;
1-[2-tert-butyl-9-[(2-chloropyridin-3-yl)methyl]purin-6-yl]-3-methylpyrrolidin-3-ol;
1-[2-tert-butyl-9-[(3-chloropyridin-2-yl)methyl]purin-6-yl]-3-methylpyrrolidin-3-ol;
1-[2-tert-butyl-9-[(4-methyl-1,2,5-oxadiazol-3-yl)methyl] purin-6-yl]-3-methylpyrrolidin-3-ol;

1-[2-tert-butyl-9-(2-methoxyethyl)purin-6-yl]-3-methylpyrrolidin-3-ol;
2-tert-butyl-9-[(2-chlorophenyl)methyl]-6-(3,3,4,4-tetrafluoropyrrolidin-1-yl)purine;
2-tert-butyl-9-[(3-chlorophenyl)methyl]-6-(3,3,4,4-tetrafluoropyrrolidin-1-yl)purine;
1-[2-tert-butyl-9-[(2-methylsulfonylphenyl)methyl]purin-6-yl]-3-methylpyrrolidin-3-ol;
N—[(S)-1-[2-tert-butyl-9-[[4-(trifluoromethyl)-1H-pyrazol-3-yl]methyl]purin-6-yl]pyrrolidin-3-yl]acetamide;
7-[2-tert-butyl-9-[[3-(trifluoromethyl)-1H-pyrazol-4-yl]methyl]purin-6-yl]-2-oxa-7-azaspiro[3.4]octane;
N-[1-[2-tert-butyl-9-[[4-(trifluoromethyl)-1H-pyrazol-3-yl]methyl]purin-6-yl]pyrrolidin-3-yl]acetamide;
7-[2-tert-butyl-9-[[4-(trifluoromethyl)-1H-pyrazol-3-yl]methyl]purin-6-yl]-2-oxa-7-azaspiro[3.4]octane;
2-[[2-tert-butyl-6-(3,3,4,4-tetrafluoropyrrolidin-1-yl)purin-9-yl]methyl]-5-methyl-1,3,4-oxadiazole;
5-[[2-tert-butyl-6-(3,3,4,4-tetrafluoropyrrolidin-1-yl)purin-9-yl]methyl]-3-methyl-1,2,4-oxadiazole;
2-tert-butyl-9-[(1-methyltetrazol-5-yl)methyl]-6-(3,3,4,4-tetrafluoropyrrolidin-1-yl)purine;
3-[[2-tert-butyl-6-(3,3,4,4-tetrafluoropyrrolidin-1-yl)purin-9-yl]methyl]-4-methyl-1,2,5-oxadiazole;
2-tert-butyl-9-(2-methoxyethyl)-6-(3,3,4,4-tetrafluoropyrrolidin-1-yl)purine;
1-[2-tert-butyl-9-[[3-(trifluoromethyl)-1H-pyrazol-4-yl]methyl]purin-6-yl]-3-methylpyrrolidin-3-ol;
1-[2-tert-butyl-9-[[4-(trifluoromethyl)-1H-pyrazol-3-yl]methyl]purin-6-yl]-3-methylpyrrolidin-3-ol;
(3S)-1-[2-tert-butyl-9-[[2-(trifluoromethyl)phenyl]methyl]purin-6-yl]pyrrolidin-3-ol;
(3S)-1-[2-tert-butyl-9-[(3-chlorophenyl)methyl]purin-6-yl]pyrrolidin-3-ol;
(3S)-1-[2-tert-butyl-9-[(4-chlorophenyl)methyl]purin-6-yl]pyrrolidin-3-ol;
7-[2-tert-butyl-9-(3,3,3-trifluoropropyl)purin-6-yl]-2-oxa-7-azaspiro[3.4]octane;
(3S)-1-[2-tert-butyl-9-[(2-methylsulfonylphenyl)methyl]purin-6-yl]pyrrolidin-3-ol;
(3S)-1-[2-tert-butyl-9-[(2-chloropyridin-3-yl)methyl]purin-6-yl]pyrrolidin-3-ol;
(3S)-1-[2-tert-butyl-9-[(3-chloropyridin-2-yl)methyl]purin-6-yl]pyrrolidin-3-ol;
2-tert-butyl-6-(3,3,4,4-tetrafluoropyrrolidin-1-yl)-9-(3,3,3-trifluoropropyl)purine;
(3S)-1-[2-tert-butyl-9-(2-methoxyethyl)purin-6-yl]pyrrolidin-3-ol;
(3S)-1-[2-tert-butyl-9-[(1-methyltetrazol-5-yl)methyl]purin-6-yl]pyrrolidin-3-ol;
(3S)-1-[2-tert-butyl-9-[(4-methyl-1,2,5-oxadiazol-3-yl)methyl]purin-6-yl]pyrrolidin-3-ol;
(3S)-1-[2-tert-butyl-9-[(2-chlorophenyl)methyl]purin-6-yl]pyrrolidin-3-ol;
(3S)-1-[2-tert-butyl-9-[[3-(trifluoromethyl)-1H-pyrazol-4-yl]methyl]purin-6-yl]pyrrolidin-3-ol;
(3S)-1-[2-tert-butyl-9-(3,3,3-trifluoropropyl)purin-6-yl]pyrrolidin-3-ol;
(3S)-1-[2-tert-butyl-9-[[4-(trifluoromethyl)-1H-pyrazol-3-yl]methyl]purin-6-yl]pyrrolidin-3-ol;
(3S)-1-[2-tert-butyl-9-[(3-methyl-1,2,4-oxadiazol-5-yl)methyl]purin-6-yl]pyrrolidin-3-ol;
1-[2-tert-butyl-9-(3,3,3-trifluoropropyl)purin-6-yl]-3-methylpyrrolidin-3-ol;
N-[(3S)-1-[2-tert-butyl-9-(3,3,3-trifluoropropyl)purin-6-yl]pyrrolidin-3-yl]acetamide;
7-[2-tert-butyl-9-[(3-chloropyridin-2-yl)methyl]purin-6-yl]-2-oxa-7-azaspiro[3.4]octane;
2-tert-butyl-6-(3,3,4,4-tetrafluoropyrrolidin-1-yl)-9-[[2-(trifluoromethyl)phenyl]methyl]purine;
2-tert-butyl-9-[(2-methylsulfonylphenyl)methyl]-6-(3,3,4,4-tetrafluoropyrrolidin-1-yl)purine;
N-tert-butyl-9-[(2-chlorophenyl)methyl]-6-(3,3-difluoropyrrolidin-1-yl)purin-2-amine;
N-tert-butyl-6-(3,3-difluoropyrrolidin-1-yl)-9-[[2-(trifluoromethyl)phenyl]methyl]purin-2-amine;
N-tert-butyl-6-(3,3-difluoropyrrolidin-1-yl)-9-[(5-methyl-1,3,4-oxadiazol-2-yl)methyl]purin-2-amine;
N-tert-butyl-6-(3,3-difluoropyrrolidin-1-yl)-9-(3,3,3-trifluoropropyl)purin-2-amine;
N-tert-butyl-6-(3,3-difluoropyrrolidin-1-yl)-9-[(4-methyl-1,2,5-oxadiazol-3-yl)methyl]purin-2-amine;
N-tert-butyl-9-[(3-chloropyridin-2-yl)methyl]-6-(3,3-difluoropyrrolidin-1-yl)purin-2-amine;
N-tert-butyl-6-(3,3-difluoropyrrolidin-1-yl)-9-[(1-methyltetrazol-5-yl)methyl]purin-2-amine;
N-tert-butyl-6-(3,3-difluoropyrrolidin-1-yl)-9-[(2-methylsulfonylphenyl)methyl]purin-2-amine;
N-tert-butyl-6-(3,3-difluoropyrrolidin-1-yl)-9-[(3-methyl-1,2,4-oxadiazol-5-yl)methyl]purin-2-amine;
(3S)-1-[2-(tert-butylamino)-9-[(2-chlorophenyl)methyl]purin-6-yl]pyrrolidin-3-ol;
(3S)-1-[2-(tert-butylamino)-9-[[2-(trifluoromethyl)phenyl]methyl]purin-6-yl]pyrrolidin-3-ol;
(3S)-1-[2-(tert-butylamino)-9-[(3-chloropyridin-2-yl)methyl]purin-6-yl]pyrrolidin-3-ol;
(3S)-1-[2-(tert-butylamino)-9-[(4-methyl-1,2,5-oxadiazol-3-yl)methyl]purin-6-yl]pyrrolidin-3-ol;
1-[2-(tert-butylamino)-9-[(2-chlorophenyl)methyl]purin-6-yl]-3-methylpyrrolidin-3-ol;
1-[2-(tert-butylamino)-9-[[2-(trifluoromethyl)phenyl]methyl]purin-6-yl]-3-methylpyrrolidin-3-ol;
(3S)-1-[2-(tert-butylamino)-9-[[3-(trifluoromethyl)-1H-pyrazol-4-yl]methyl]purin-6-yl]pyrrolidin-3-ol;
1-[2-(tert-butylamino)-9-[(4-methyl-1,2,5-oxadiazol-3-yl)methyl]purin-6-yl]-3-methylpyrrolidin-3-ol;
9-[(2-chlorophenyl)methyl]-6-(3,3-difluoropyrrolidin-1-yl)-2-(2,2-dimethylpropoxy)purine;
6-(3,3-difluoropyrrolidin-1-yl)-2-(2,2-dimethylpropoxy)-9-[[2-(trifluoromethyl)phenyl]methyl]purine;
6-(3,3-difluoropyrrolidin-1-yl)-2-(2,2-dimethylpropoxy)-9-[(2-methylsulfonylphenyl)methyl]purine;
2-[[6-(3,3-difluoropyrrolidin-1-yl)-2-(2,2-dimethylpropoxy)purin-9-yl]methyl]-5-methyl-1,3,4-oxadiazole;
5-[[6-(3,3-difluoropyrrolidin-1-yl)-2-(2,2-dimethylpropoxy)purin-9-yl]methyl]-3-methyl-1,2,4-oxadiazole;
6-(3,3-difluoropyrrolidin-1-yl)-2-(2,2-dimethylpropoxy)-9-[(1-methyltetrazol-5-yl)methyl]purine;
(3S)-1-[2-(tert-butylamino)-9-(3,3,3-trifluoropropyl)purin-6-yl]pyrrolidin-3-ol;
1-[9-[(2-chlorophenyl)methyl]-2-(2,2-dimethylpropoxy)purin-6-yl]-3-methylpyrrolidin-3-ol;
1-[2-(2,2-dimethylpropoxy)-9-[[2-(trifluoromethyl)phenyl]methyl]purin-6-yl]-3-methylpyrrolidin-3-ol;
1-[2-(2,2-dimethylpropoxy)-9-[(2-methylsulfonylphenyl)methyl]purin-6-yl]-3-methylpyrrolidin-3-ol;
1-[9-[(3-chloropyridin-2-yl)methyl]-2-(2,2-dimethylpropoxy)purin-6-yl]-3-methylpyrrolidin-3-ol;
1-[2-(2,2-dimethylpropoxy)-9-[(4-methyl-1,2,5-oxadiazol-3-yl)methyl]purin-6-yl]-3-methylpyrrolidin-3-ol;
1-[2-(tert-butylamino)-9-[[3-(trifluoromethyl)-1H-pyrazol-4-yl]methyl]purin-6-yl]-3-methylpyrrolidin-3-ol;

N-tert-butyl-6-(2-oxa-6-azaspiro[3.3]heptan-6-yl)-9-[[2-(trifluoromethyl)phenyl]methyl]purin-2-amine;
N-tert-butyl-9-[(2-chlorophenyl)methyl]-6-(2-oxa-6-azaspiro[3.3]heptan-6-yl)purin-2-amine;
(3S)-1-[2-tert-butyl-9-[(1-cyclopropyltetrazol-5-yl)methyl]purin-6-yl]pyrrolidin-3-ol;
3-[[6-(3,3-difluoropyrrolidin-1-yl)-2-(2,2-dimethylpropoxy)purin-9-yl]methyl]-4-methyl-1,2,5-oxadiazole;
N-tert-butyl-9-[(3-methyl-1,2,4-oxadiazol-5-yl)methyl]-6-(2-oxa-6-azaspiro[3.3]heptan-6-yl)purin-2-amine;
N-tert-butyl-6-(2-oxa-6-azaspiro[3.3]heptan-6-yl)-9-(3,3,3-trifluoropropyl)purin-2-amine;
6-[9-[(2-chlorophenyl)methyl]-2-(2,2-dimethylpropoxy)purin-6-yl]-2-oxa-6-azaspiro[3.3]heptane;
3-[[2-tert-butyl-6-(4-methylpiperazin-1-yl)purin-9-yl]methyl]-4-methyl-1,2,5-oxadiazole;
[(2R)-1-[2-tert-butyl-9-[(4-methyl-1,2,5-oxadiazol-3-yl)methyl]purin-6-yl]pyrrolidin-2-yl]methanol;
[(2R)-1-[2-tert-butyl-9-[(1-cyclopropyltetrazol-5-yl)methyl]purin-6-yl]pyrrolidin-2-yl]methanol;
(2R)-1-[2-tert-butyl-9-[(1-cyclopropyltetrazol-5-yl)methyl]purin-6-yl]pyrrolidine-2-carbonitrile;
(2R)-1-[2-tert-butyl-9-[(4-methyl-1,2,5-oxadiazol-3-yl)methyl]purin-6-yl]pyrrolidine-2-carbonitrile;
6-[2-tert-butyl-9-[(4-methyl-1,2,5-oxadiazol-3-yl)methyl]purin-6-yl]-2-oxa-6-azaspiro[3.3]heptane; and
3-[[2-tert-butyl-6-(1,3-thiazolidin-3-yl)purin-9-yl]methyl]-4-methyl-1,2,5-oxadiazole.

The invention particularly also relates to a compound of formula (I) selected from:
6-(3,3-Difluoropyrrolidin-1-yl)-2-(2,2-dimethylpropoxy)-9H-purine;
[(3S)-1-[2-(tert-Butylamino)-9-[(4-methyl-1,2,5-oxadiazol-3-yl)methyl]purin-6-yl]pyrrolidin-3-yl]acetate;
[1-[2-(tert-Butylamino)-9-[(4-methyl-1,2,5-oxadiazol-3-yl)methyl]purin-6-yl]-3-methylpyrrolidin-3-yl]acetate;
9-Benzyl-2-chloro-6-(3,3-difluoropyrrolidin-1-yl)purine;
(3S)-1-[2-tert-Butyl-9-[(1-propan-2-yltetrazol-5-yl)methyl]purin-6-yl]pyrrolidin-3-ol;
2-tert-Butyl-9-[(1-cyclopropyltetrazol-5-yl)methyl]-6-(3,3-difluoropyrrolidin-1-yl)purine;
[(2R)-1-[2-tert-Butyl-9-[(3-chloropyridin-2-yl)methyl]purin-6-yl]pyrrolidin-2-yl]methanol;
(3S)-1-[2-tert-Butyl-9-[(1-propyltetrazol-5-yl)methyl]purin-6-yl]pyrrolidin-3-ol;
(2R,3S)-1-[2-tert-Butyl-9-[(3-chloropyridin-2-yl)methyl]purin-6-yl]-2-(hydroxymethyl)pyrrolidin-3-ol;
2-tert-Butyl-9-[(3-chloropyridin-2-yl)methyl]-6-(3,3-difluoroazetidin-1-yl)purine;
3-[2-tert-Butyl-9-[(3-chloropyridin-2-yl)methyl]purin-6-yl]-1,3-thiazolidine;
6-[2-tert-Butyl-9-[(3-chloropyridin-2-yl)methyl]purin-6-yl]-2λ6-thia-6-azaspiro[3.3]heptane 2,2-dioxide;
(2R)-1-[2-tert-Butyl-9-[(3-chloropyridin-2-yl)methyl]purin-6-yl]pyrrolidine-2-carbonitrile;
(3S)-1-[2-tert-Butyl-9-[[1-(cyclopropylmethyl)tetrazol-5-yl]methyl]purin-6-yl]pyrrolidin-3-ol;
1-[2-tert-Butyl-9-[(3-chloropyridin-2-yl)methyl]purin-6-yl]-3-(trifluoromethyl)pyrrolidin-3-ol;
(3S)-1-[2-tert-Butyl-9-[(1-tert-butyltetrazol-5-yl)methyl]purin-6-yl]pyrrolidin-3-ol;
1-[2-tert-butyl-9-[(3-chloropyridin-2-yl)methyl]purin-6-yl]-3-(trifluoromethyl)azetidin-3-ol;
2-tert-Butyl-9-[(3-chloropyridin-2-yl)methyl]-6-(2,2-difluoro-5-azaspiro[2.4]heptan-5-yl)purine; and
1-[2-tert-Butyl-9-[(3-chloropyridin-2-yl)methyl]purin-6-yl]-3-methylazetidin-3-ol.

The invention further relates to a compound of formula (I) selected from:
2-tert-butyl-9-[(2-chlorophenyl)methyl]-6-(3,3-difluoropyrrolidin-1-yl)purine;
2-tert-butyl-9-[(2-chloro-4-fluorophenyl)methyl]-6-(3,3-difluoropyrrolidin-1-yl)purine;
2-tert-butyl-6-(3,3-difluoropyrrolidin-1-yl)-9-[[2-(trifluoromethyl)phenyl]methyl]purine;
2-tert-butyl-9-[(2-chloropyridin-3-yl)methyl]-6-(3,3-difluoropyrrolidin-1-yl)purine;
2-tert-butyl-6-(3,3-difluoropyrrolidin-1-yl)-9-(oxolan-3-yl)purine;
2-[2-tert-butyl-6-(3,3-difluoropyrrolidin-1-yl)purin-9-yl]-1-(2-chlorophenyl)ethanone;
2-tert-butyl-6-(3,3-difluoropyrrolidin-1-yl)-9-[(2-methylsulfonylphenyl)methyl]purine;
2-tert-butyl-9-[(3-chloropyridin-2-yl)methyl]-6-(3,3-difluoropyrrolidin-1-yl)purine;
2-tert-butyl-6-(3,3-difluoropyrrolidin-1-yl)-9-(2-pyridin-3-ylethyl)purine;
1-[2-tert-butyl-9-[[2-(trifluoromethyl)phenyl]methyl]purin-6-yl]pyrrolidin-3-ol;
1-[2-tert-butyl-9-[(3-chloropyridin-2-yl)methyl]purin-6-yl]pyrrolidin-3-ol;
1-[2-tert-butyl-9-[(2-chloropyridin-3-yl)methyl]purin-6-yl]pyrrolidin-3-ol;
1-[2-tert-butyl-9-[(2-chloro-4-fluorophenyl)methyl]purin-6-yl]pyrrolidin-3-ol;
(3S)-1-[2-tert-butyl-9-[[2-(trifluoromethyl)phenyl]methyl]purin-6-yl]pyrrolidin-3-ol;
(3S)-1-[2-tert-butyl-9-[(3-chlorophenyl)methyl]purin-6-yl]pyrrolidin-3-ol;
(3S)-1-[2-tert-butyl-9-[(2-chloropyridin-3-yl)methyl]purin-6-yl]pyrrolidin-3-ol;
(3S)-1-[2-tert-butyl-9-[(2-chlorophenyl)methyl]purin-6-yl]pyrrolidin-3-ol;
9-[(2-chlorophenyl)methyl]-6-(3,3-difluoropyrrolidin-1-yl)-2-(2,2-dimethylpropoxy)purine; and
6-(3,3-difluoropyrrolidin-1-yl)-2-(2,2-dimethylpropoxy)-9-[[2-(trifluoromethyl)phenyl]methyl]purine.

The invention also particularly relates to a compound of formula (I) selected from:
2-tert-Butyl-9-[(1-cyclopropyltetrazol-5-yl)methyl]-6-(3,3-difluoropyrrolidin-1-yl)purine;
[(2R)-1-[2-tert-Butyl-9-[(3-chloropyridin-2-yl)methyl]purin-6-yl]pyrrolidin-2-yl]methanol;
2-tert-Butyl-9-[(3-chloropyridin-2-yl)methyl]-6-(3,3-difluoroazetidin-1-yl)purine;
3-[2-tert-Butyl-9-[(3-chloropyridin-2-yl)methyl]purin-6-yl]-1,3-thiazolidine;
(2R)-1-[2-tert-Butyl-9-[(3-chloropyridin-2-yl)methyl]purin-6-yl]pyrrolidine-2-carbonitrile; and
1-[2-tert-butyl-9-[(3-chloropyridin-2-yl)methyl]purin-6-yl]-3-(trifluoromethyl)azetidin-3-ol.

The invention also relates in particular to:
The use of a compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis;

A compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis; and A method for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis, which method comprises administering an effective amount of a compound of formula (I) to a patient in need thereof. The invention particularly relates to a compound of formula (I) for the treatment or prophylaxis of ischemia, reperfusion injury, liver fibrosis or kidney fibrosis, in particular ischemia or reperfusion injury.

The invention particularly relates to a compound of formula (I) for the treatment or prophylaxis of myocardial infarction.

The invention further particularly relates to a compound of formula (I) for the treatment or prophylaxis of age-related macular degeneration, diabetic retinopathy, glaucoma, retinal vein occlusion, retinopathy of prematurity, ocular ischemic syndrome, geographic atrophy or uveitis.

The invention further particularly relates to a compound of formula (I) for the treatment or prophylaxis of amyotrophic lateral sclerosis or multiple sclerosis.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 2nd Edition, Richard C. Larock. John Wiley & Sons, New York, N.Y. 1999). There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The synthesis of the compound of formula (I) can, for example, be accomplished according to the following schemes.

Scheme 1

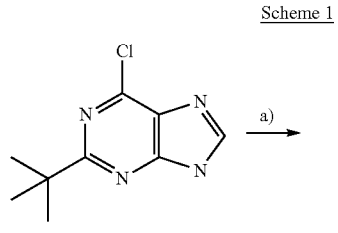

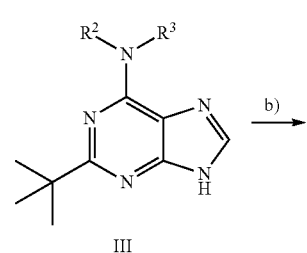

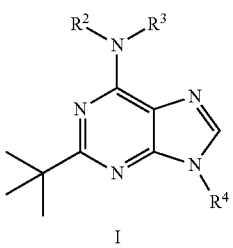

I a) 2-tert-Butyl-6-chloro-9H-purine II can conveniently be reacted with an amine (commercially available, or known in the art) in the presence or the absence of a base to afford intermediate III.

b) Intermediate III can conveniently be reacted with an electrophile (commercially available, or known in the art) in the presence or absence of a base to yield title compound I. This might be the final desired compound however any protecting group either on $R^3$ or $NR^2R^3$ can conveniently be cleaved under appropriate conditions to yield the desired final compound I.

Scheme 2

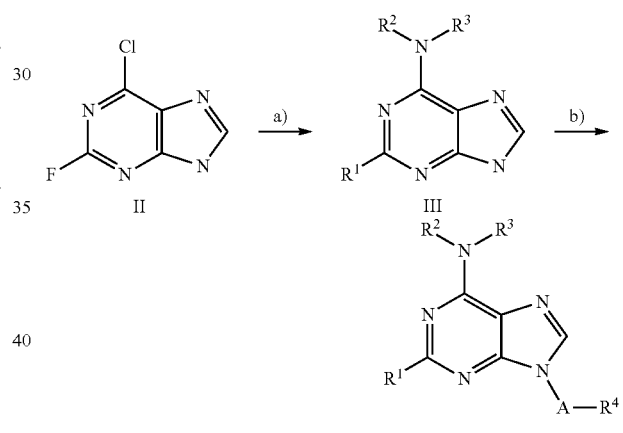

a) 6-Chloro-2-fluoro-9H-purine II is commercially available (any other suitable substituted purine serves as equal starting material) or can be accessed by methods known in the art and can conveniently be reacted with nucleophiles (1. amine 2. alcohol alternatively: 1. amine 2. amine, depending on the nature and reactivity of the respective amines) to access substituted imidazopyrimidine derivatives III. The use of protecting groups is optionally advised depending on the nature and the reactivity of the reagents.

b) Intermediate III can conveniently be reacted with an electrophile (commercially available, or known in the art) in the presence or absence of a base to yield title compound I. This might be the final desired compound however any protecting group either on $R^4$ or $NR^2R^3$ can conveniently be cleaved under appropriate conditions to yield the desired final compound I.

The invention thus also relates to a process for the preparation of a compound of formula (I) comprising the reaction of a compound of formula (A)

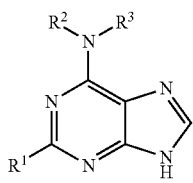

in the presence of Y-A-R⁴ wherein Y is a leaving group and wherein A and $R^1$ to $R^4$ are as defined above.

In the process of the invention, suitable leaving groups are for example chlorine or bromine.

The process of the invention can be carried out in the presence of a base. Examples of suitable bases are NaH or KOtBu.

The process of the invention can be carried out for example in NMP (N-Methyl-2-pyrrolidone), DMF (dimethylformamide) or THF (tetrahydrofurane).

The invention is further directed to a compound of formula (I), when manufactured according to a process according to the invention.

The invention will now be illustrated by the following examples which have no limiting character.

EXAMPLES

Example 1

2-Tert-Butyl-9-[(4-Chlorophenyl)Methyl]-6-(3,3-Difluoropyrrolidin-1-Yl)Purine

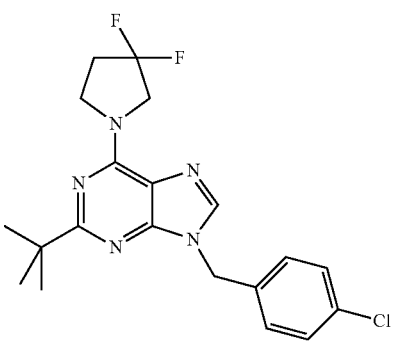 [SMILES: CC(C)(C)c1nc(N2CCC(F)(F)C2)c2ncn(Cc3ccc(Cl)cc3)c2n1]

a) 5-(2,2-Dimethyl-propionylamino)-1H-imidazole-4-carboxylic acid amide

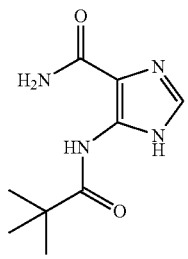

To a solution of 5-amino-1H-imidazole-4-carboxylic acid amide (10 g, 79.36 mmol) and DMAP (291 mg, 2.38 mmol) in anhydrous pyridine (200 mL) was slowly added 2,2-dimethyl-propionyl chloride (10.74 mL, 87.30 mmol) and the reaction mixture was stirred at 80° C. for 8 h. The solvent was evaporated under reduced pressure and the residue was diluted with cold water (50 mL). The precipitate was filtered, washed with water (30 mL) and dried to get yield the title compound (9 g, 54%) as ash-color solid. MS(m/e): 211.4 (M+H).

b) 2-tert-Butyl-1,9-dihydro-purin-6-one

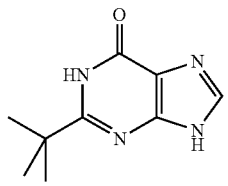

A solution 5-(2,2-dimethyl-propionylamino)-1H-imidazole-4-carboxylic acid amide (22 g, 174.6 mmol) in aqueous $KHCO_3$ solution (0.5N, 400 mL) was heated to reflux for 48 h. The reaction mixture was concentrated under reduced pressure, the residue was cooled to 0° C. and pH was adjusted to 6 using 10% aqueous HCl solution. The precipitate was filtered, washed with water and azeotroped with toluene to access a brown solid that was purified by column chromatography over silica gel (2-5% MeOH/DCM) to get yield the title compound (12 g, 36%) as pale yellow solid. MS(m/e): 191.0 (M+H).

c) 2-tert-Butyl-6-chloro-9H-purine

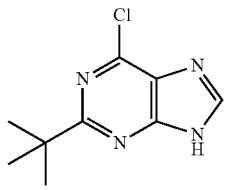

To a solution of 2-tert-butyl-5,9-dihydro-purin-6-one (4 g, 20.83 mmol) in $CHCl_3$ (100 mL) was added DMF (4 mL) followed by $SOCl_2$ (3.04 mL, 41.66 mmol) and the reaction mixture was refluxed for 3 h. Volatilities were removed in vacuo and the residue was diluted with water (50 mL), stirred for 10 min at 25° C. and filtered. The precipitate was washed with water and pentane yield the title compound (3.6 g, 82%) as off-white solid. MS(m/e): 211.2 (M+H).

d) 2-tert-Butyl-6-(3,3-difluoro-pyrrolidin-1-yl)-9H-purine

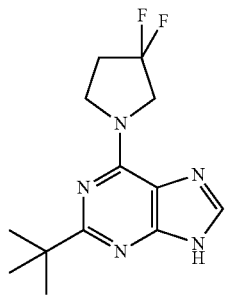 [SMILES: CC(C)(C)c1nc(N2CCC(F)(F)C2)c2nc[nH]c2n1]

To a solution of 2-tert-butyl-6-chloro-9H-purine (970 mg, 4.62 mmol) and 3,3-difluoro-pyrrolidine (995 mg, 6.93 mmol) in EtOH (10 mL) was added DIPEA (2.29 mL, 13.86 mmol) and the reaction mixture was stirred at 100° C. for 16 h. The solvent was evaporated, the residue was dissolved with DCM (60 mL) and washed with water. The organic layer was dried over Na₂SO₄, filtered and evaporated. The residue was purified by column chromatography over silica gel (25-30% EtOAc/hexane) to yield (1 g, 77%) as off-white solid. MS(m/e): 282.2 (M+H).

e) 2-tert-butyl-9-[(4-chlorophenyl)methyl]-6-(3,3-difluoropyrrolidin-1-yl)purine To a solution of 2-tert-butyl-6-(3,3-difluoro-pyrrolidin-1-yl)-9H-purine (50 mg, 0.178 mmol) in dry DMF (3 mL) at 0° C. was added NaH (60% in mineral oil) (10 mg, 0.214 mmol) and the reaction mixture was stirred at 25° C. for 45 min. 1-Bromomethyl-4-chloro-benzene (54.7 mg, 0.267 mmol) was added to reaction mixture at 0° C., and the reaction mixture was heated to 60° C. for 16 h. The mixture was quenched with water (10 mL) and extracted with EtOAc (2×15 mL). The combined organic layer was dried over Na₂SO₄, filtered and evaporated. The residue was purified by column chromatography over silica gel (20-30% EtOAc/hexane) to yield (54.7 mg, 61%) as pale yellow liquid. MS(m/e): 406.4 (M+H).

Example 2

2-tert-butyl-9-[(2-chlorophenyl)methyl]-6-(3,3-difluoropyrrolidin-1-yl)purine

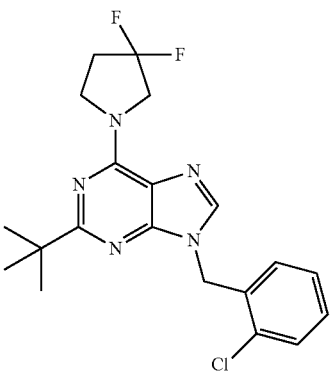 [SMILES: CC(C)(C)c1nc(N2CCC(F)(F)C2)c2ncn(Cc3ccccc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 1-bromomethyl-2-chloro-benzene. MS(m/e): 406.4 (M+H).

Example 3

2-tert-butyl-6-(3,3-difluoropyrrolidin-1-yl)-9-[(4-methylphenyl)methyl]purine

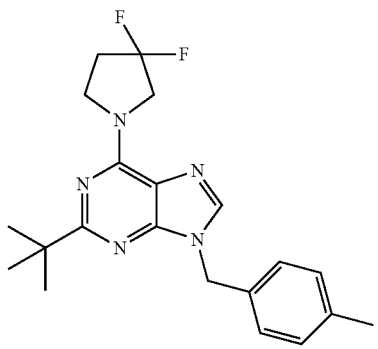 [SMILES: Cc1ccc(Cn2cnc3c(N4CCC(F)(F)C4)nc(C(C)(C)C)nc32)cc1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 1-bromomethyl-4-methyl-benzene. MS(m/e): 386.0 (M+H).

Example 4

2-tert-butyl-9-[(2-chloro-4-fluorophenyl)methyl]-6-(3,3-difluoropyrrolidin-1-yl)purine

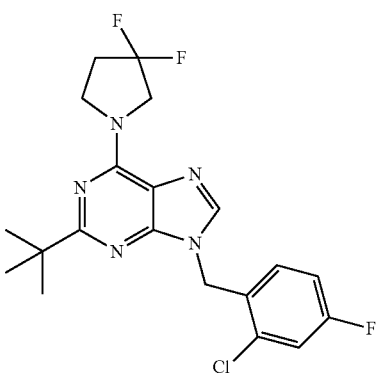 [SMILES: CC(C)(C)c1nc(N2CCC(F)(F)C2)c2ncn(Cc3ccc(F)cc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 1-bromomethyl-2-chloro-4-fluoro-benzene. MS(m/e): 424.0 (M+H).

Example 5

2-tert-butyl-6-(3,3-difluoropyrrolidin-1-yl)-9-[[2-(trifluoromethyl)phenyl]methyl]purine

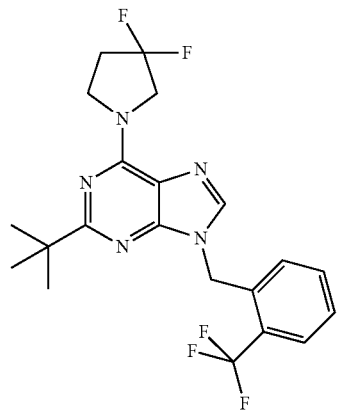 [SMILES: CC(C)(C)c1nc(N2CCC(F)(F)C2)c2ncn(Cc3ccccc3C(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 1-bromomethyl-2-trifluoromethyl-benzene. MS(m/e): 440.0 (M+H).

Example 6

2-tert-butyl-9-[(2-chloropyridin-3-yl)methyl]-6-(3,3-difluoropyrrolidin-1-yl)purine

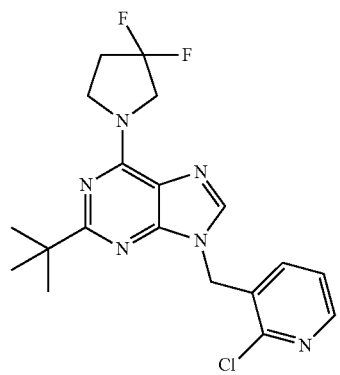 [SMILES: CC(C)(C)c1nc(N2CCC(F)(F)C2)c2ncn(Cc3cccnc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 2-chloro-3-chloromethyl-pyridine. MS(m/e): 407.0 (M+H).

Example 7

5-[[2-tert-butyl-6-(3,3-difluoropyrrolidin-1-yl)purin-9-yl]methyl]-3-methyl-1,2,4-oxadiazole

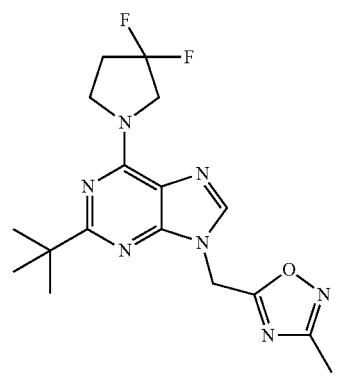 [SMILES: Cc1noc(Cn2cnc3c(N4CCC(F)(F)C4)nc(C(C)(C)C)nc32)n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 5-chloromethyl-3-methyl-[1,2,4]oxadiazole. MS(m/e): 378.2 (M+H).

Example 8

2-tert-butyl-9-(cyclohexylmethyl)-6-(3,3-difluoropyrrolidin-1-yl)purine

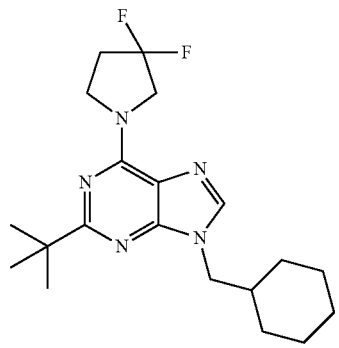 [SMILES: CC(C)(C)c1nc(N2CCC(F)(F)C2)c2ncn(CC3CCCCC3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and bromomethyl-cyclohexane. MS(m/e): 378.2 (M+H).

Example 9

2-tert-butyl-6-(3,3-difluoropyrrolidin-1-yl)-9-ethyl-purine

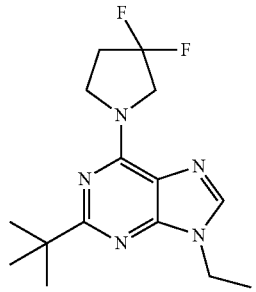 [SMILES: CCn1cnc2c(N3CCC(F)(F)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and iodo-ethane. MS(m/e): 310.2 (M+H).

Example 10

2-tert-butyl-6-(3,3-difluoropyrrolidin-1-yl)-9-propyl-purine

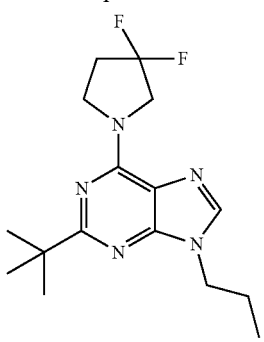

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 1-iodo-propane. MS(m/e): 324.0 (M+H).

Example 11

2-[[2-tert-butyl-6-(3,3-difluoropyrrolidin-1-yl)purin-9-yl]methyl]-5-methyl-1,3,4-oxadiazole

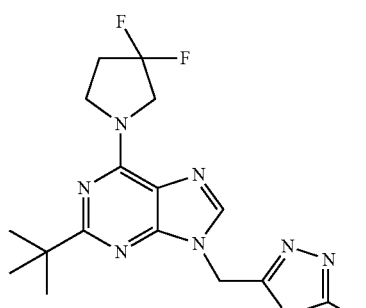

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 2-chloromethyl-5-methyl-[1,3,4]oxadiazole. MS(m/e): 378.2 (M+H).

Example 12

2-tert-butyl-6-(3,3-difluoropyrrolidin-1-yl)-9-(oxolan-3-yl)purine

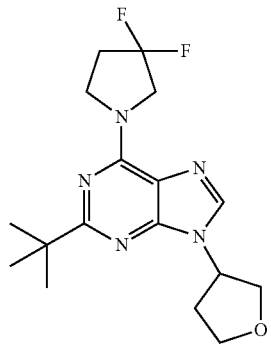 [SMILES: CC(C)(C)c1nc(N2CCC(F)(F)C2)c2ncn(C3CCOC3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 3-bromo-tetrahydrofuran. MS(m/e): 352.0 (M+H).

Example 13

2-tert-butyl-6-(3,3-difluoropyrrolidin-1-yl)-9-(2-phenylethyl)purine

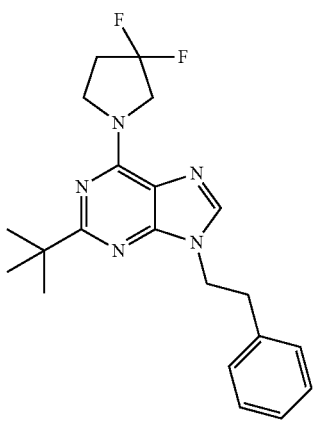 [SMILES: CC(C)(C)c1nc(N2CCC(F)(F)C2)c2ncn(CCc3ccccc3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 2-bromo-ethyl)-benzene. MS(m/e): 386.0 (M+H).

Example 14

2-tert-butyl-6-(3,3-difluoropyrrolidin-1-yl)-9-[(1-methyltetrazol-5-yl)methyl]purine

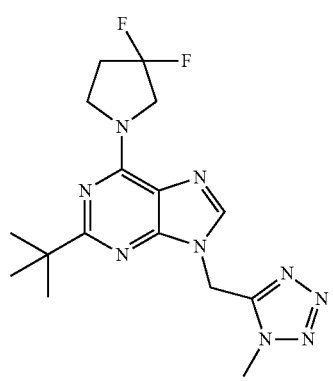 [SMILES: Cn1nnnc1Cn1cnc2c(N3CCC(F)(F)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 5-chloromethyl-1-methyl-1H-tetrazole. MS(m/e): 378.2 (M+H).

Example 15

2-tert-butyl-6-(3,3-difluoropyrrolidin-1-yl)-9-(2-methoxyethyl)purine

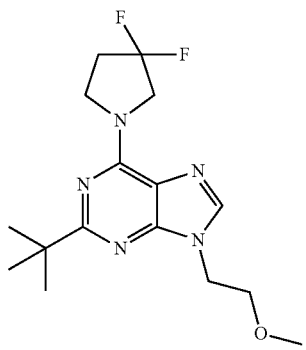 [SMILES: COCCn1cnc2c(N3CCC(F)(F)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 1-Iodo-2-methoxy-ethane. MS(m/e): 340.0 (M+H).

Example 16

3-[[2-tert-butyl-6-(3,3-difluoropyrrolidin-1-yl)purin-9-yl]methyl]-4-methyl-1,2,5-oxadiazole

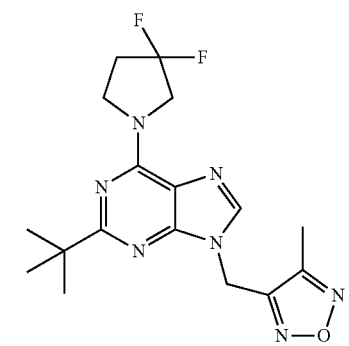 [SMILES: Cc1nonc1Cn1cnc2c(N3CCC(F)(F)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 3-chloromethyl-4-methyl-furazan. MS(m/e): 378.2 (M+H).

Example 17

2-[2-tert-butyl-6-(3,3-difluoropyrrolidin-1-yl)purin-9-yl]-1-(2-chlorophenyl)ethanone

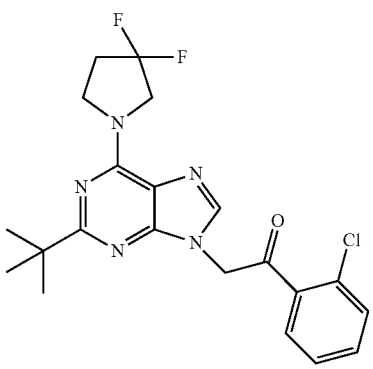 [SMILES: CC(C)(C)c1nc(N2CCC(F)(F)C2)c2ncn(CC(=O)c3ccccc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 2-bromo-1-(2-chlorophenyl)-ethanone. MS(m/e): 434.0 (M+H).

Example 18

2-tert-butyl-6-(3,3-difluoropyrrolidin-1-yl)-9-[(2-methylsulfonylphenyl)methyl]purine

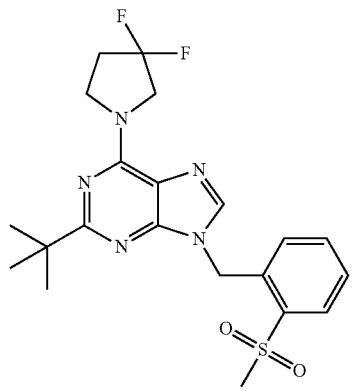 [SMILES: CC(C)(C)c1nc(N2CCC(F)(F)C2)c2ncn(Cc3ccccc3S(C)(=O)=O)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 1-bromomethyl-2-methanesulfonyl-benzene. MS(m/e): 450.0 (M+H).

Example 19

2-tert-butyl-6-(3,3-difluoropyrrolidin-1-yl)-9-(3,3,3-trifluoropropyl)purine

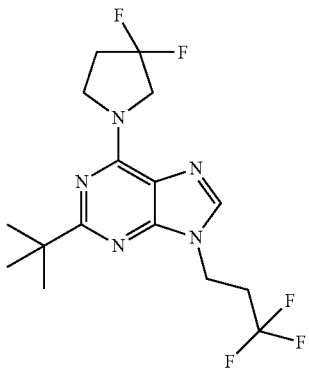 [SMILES: CC(C)(C)c1nc(N2CCC(F)(F)C2)c2ncn(CCC(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 1,1,1-trifluoro-3-iodo-propane. MS(m/e): 378.2 (M+H).

Example 20

2-tert-butyl-6-(3,3-difluoropyrrolidin-1-yl)-9-[(4-methoxyphenyl)methyl]purine

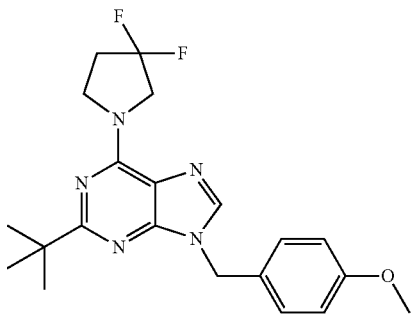 [SMILES: COc1ccc(Cn2cnc3c(N4CCC(F)(F)C4)nc(C(C)(C)C)nc32)cc1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 1-bromomethyl-4-methoxy-benzene. MS(m/e): 402.2 (M+H).

Example 21

2-tert-butyl-9-[(3-chloropyridin-2-yl)methyl]-6-(3,3-difluoropyrrolidin-1-yl)purine

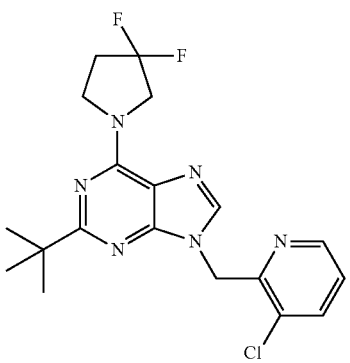 [SMILES: CC(C)(C)c1nc(N2CCC(F)(F)C2)c2ncn(Cc3ncccc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 3-chloro-2-chloromethyl-pyridine. MS(m/e): 407.0 (M+H).

Example 22

1-[2-tert-butyl-9-[(2-chlorophenyl)methyl]purin-6-yl]pyrrolidin-3-ol

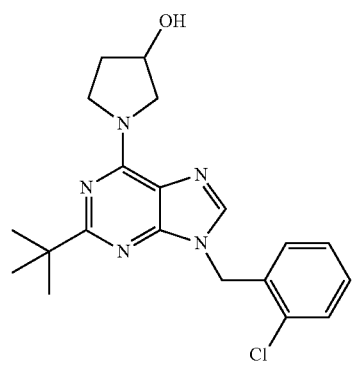

a) Acetic acid 1-(2-tert-butyl-9H-purin-6-yl)-pyrrolidin-3-yl ester

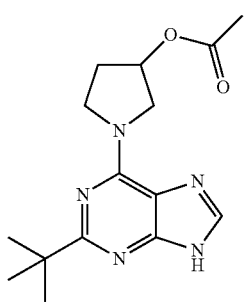 [SMILES: CC(=O)OC1CCN(c2nc(C(C)(C)C)nc3[nH]cnc23)C1]

To a solution of 2-tert-butyl-6-chloro-9H-purine (1.2 g, 5.71 mmol) and acetic acid pyrrolidin-3-yl ester (1.66 g, 6.85 mmol) in EtOH (7 mL) was added Et$_3$N (2.37 mL, 17.14 mmol) at 25° C., and the reaction mixture was stirred at 100° C. for 5 h. The solvent was evaporated and the residue was purified by column chromatography over silica (30-45% EtOAc/hexane) to yield the title compound (1.1 g, 63%) as off white solid. MS(m/e): 304.0 (M+H).

b) 1-[2-tert-butyl-9-[(2-chlorophenyl)methyl]purin-6-yl]pyrrolidin-3-ol

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 1-bromomethyl-2-chloro-benzene plus subsequent treatment of the crude mixture/residue with K$_2$CO$_3$ in MeOH to cleave the ester moiety. MS(m/e): 386.2 (M+H).

Example 23

2-tert-butyl-6-(3,3-difluoropyrrolidin-1-yl)-9-(2-pyridin-3-ylethyl)purine

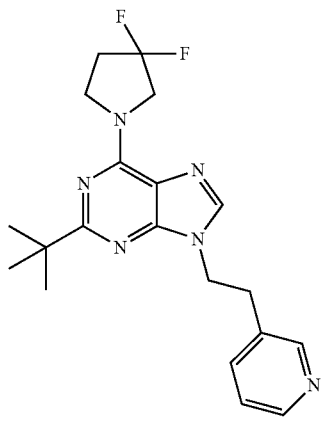 [SMILES: CC(C)(C)c1nc(N2CCC(F)(F)C2)c2ncn(CCc3cccnc3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 3-(2-bromo-ethyl)-pyridine. MS(m/e): 387.2 (M+H).

Example 24

2-[2-tert-butyl-6-(3,3-difluoropyrrolidin-1-yl)purin-9-yl]-1-pyridin-2-ylethanone

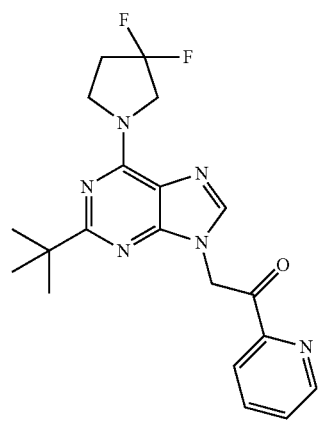 [SMILES: CC(C)(C)c1nc(N2CCC(F)(F)C2)c2ncn(CC(=O)c3ccccn3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 2-bromo-1-pyridin-2-yl-ethanone. MS(m/e): 401.2 (M+H).

Example 25

1-[2-tert-butyl-9-[(3-chlorophenyl)methyl]purin-6-yl]pyrrolidin-3-ol

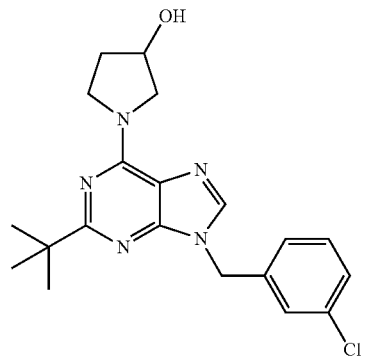 [SMILES: CC(C)(C)c1nc(N2CCC(O)C2)c2ncn(Cc3cccc(Cl)c3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 1-bromomethyl-3-chloro-benzene plus subsequent treatment of the crude mixture/residue with $K_2CO_3$ in MeOH to cleave the ester moiety. MS(m/e): 386.2 (M+H).

Example 26

1-[2-tert-butyl-9-[(4-chlorophenyl)methyl]purin-6-yl]pyrrolidin-3-ol

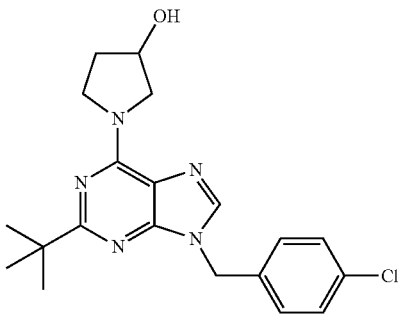 [SMILES: CC(C)(C)c1nc(N2CCC(O)C2)c2ncn(Cc3ccc(Cl)cc3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 1-bromomethyl-4-chloro-benzene plus subsequent treatment of the crude mixture/residue with $K_2CO_3$ in MeOH to cleave the ester moiety. MS(m/e): 386.2 (M+H).

Example 27

3-[2-tert-butyl-6-(3,3-difluoropyrrolidin-1-yl)purin-9-yl]thietane 1,1-dioxide

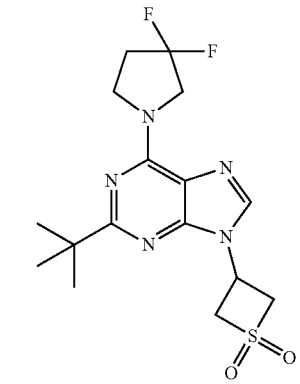 [SMILES: CC(C)(C)c1nc(N2CCC(F)(F)C2)c2ncn(C3CS(=O)(=O)C3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 3-bromo-thietane 1,1-dioxide. MS(m/e): 386.2 (M+H).

Example 28

1-[2-tert-butyl-9-[[2-(trifluoromethyl)phenyl]methyl]purin-6-yl]pyrrolidin-3-ol

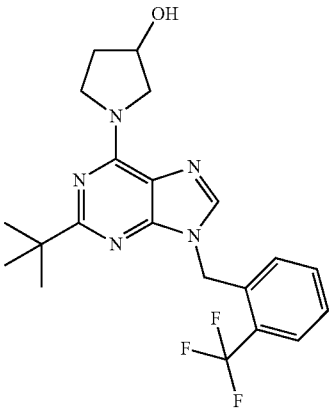 [SMILES: CC(C)(C)c1nc(N2CCC(O)C2)c2ncn(Cc3ccccc3C(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 1-bromomethyl-2-trifluoromethyl-benzene plus subsequent treatment of the crude mixture/residue with $K_2CO_3$ in MeOH to cleave the ester moiety. MS(m/e): 420.2 (M+H).

Example 29

1-[2-tert-butyl-9-[(3-methyl-1,2,4-oxadiazol-5-yl)methyl]purin-6-yl]pyrrolidin-3-ol

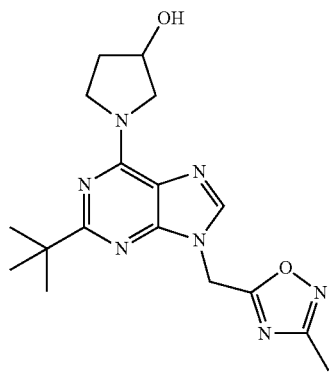 [SMILES: Cc1noc(Cn2cnc3c(N4CCC(O)C4)nc(C(C)(C)C)nc32)n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 5-chloromethyl-3-methyl-[1,2,4]oxadiazole plus subsequent treatment of the crude mixture/residue with $K_2CO_3$ in MeOH to cleave the ester moiety. MS(m/e): 358.0 (M+H).

Example 30

1-[2-tert-butyl-9-[(1-methyltetrazol-5-yl)methyl]purin-6-yl]pyrrolidin-3-ol

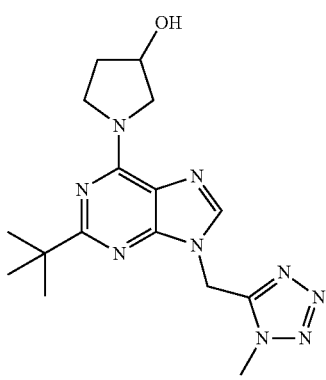 [SMILES: Cn1nnnc1Cn1cnc2c(N3CCC(O)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 5-chloromethyl-1-methyl-1H-tetrazole plus subsequent treatment of the crude mixture/residue with $K_2CO_3$ in MeOH to cleave the ester moiety. MS(m/e): 358.2 (M+H).

Example 31

1-[2-tert-butyl-9-[(4-methoxyphenyl)methyl]purin-6-yl]pyrrolidin-3-ol

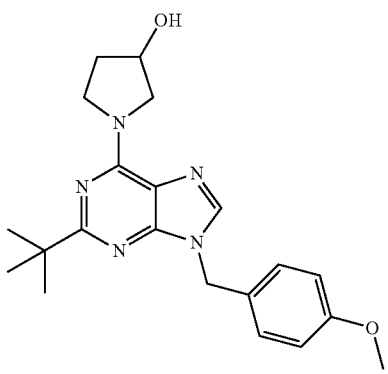 [SMILES: COc1ccc(Cn2cnc3c(N4CCC(O)C4)nc(C(C)(C)C)nc32)cc1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 1-bromomethyl-4-methoxy-benzene plus subsequent treatment of the crude mixture/residue with $K_2CO_3$ in MeOH to cleave the ester moiety. MS(m/e): 382.0 (M+H).

Example 32

1-[2-tert-butyl-9-[(3-chloropyridin-2-yl)methyl]purin-6-yl]pyrrolidin-3-ol

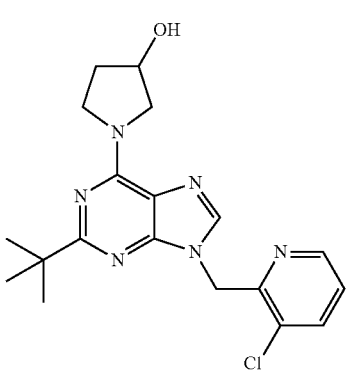 [SMILES: CC(C)(C)c1nc(N2CCC(O)C2)c2ncn(Cc3ncccc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 3-chloro-2-chloromethyl-pyridine plus subsequent treatment of the crude mixture/residue with $K_2CO_3$ in MeOH to cleave the ester moiety. MS(m/e): 387.0 (M+H).

Example 33

1-[2-tert-butyl-9-[(2-chloropyridin-3-yl)methyl]pu-
rin-6-yl]pyrrolidin-3-ol

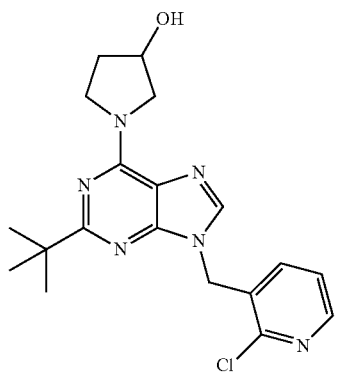 [SMILES: CC(C)(C)c1nc(N2CCC(O)C2)c2ncn(Cc3cccnc3Cl)c2n1]

In analogy to the procedure described for the synthesis of 2-tert-butyl-9-[(4-chlorophenyl)methyl]-6-(3,3-difluoropyr-rolidin-1-yl)purine (example 1) the title compound was prepared from Acetic acid 1-(2-tert-butyl-9H-purin-6-yl)-pyrrolidin-3-yl ester (example 22, step a) and 2-chloro-3-chloromethyl-pyridine plus subsequent treatment of the crude mixture/residue with K₂CO₃ in MeOH to cleave the ester moiety. MS(m/e): 387.0 (M+H).

Example 34

1-[2-tert-butyl-9-[(2-methylsulfonylphenyl)methyl]
purin-6-yl]pyrrolidin-3-ol

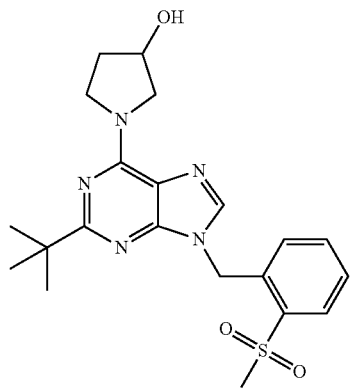 [SMILES: CC(C)(C)c1nc(N2CCC(O)C2)c2ncn(Cc3ccccc3S(C)(=O)=O)c2n1]

In analogy to the procedure described for the synthesis of 2-tert-butyl-9-[(4-chlorophenyl)methyl]-6-(3,3-difluoropyr-rolidin-1-yl)purine (example 1) the title compound was prepared from Acetic acid 1-(2-tert-butyl-9H-purin-6-yl)-pyrrolidin-3-yl ester (example 22, step a) and 1-bromom-ethyl-2-methanesulfonyl-benzene plus subsequent treatment of the crude mixture/residue with K₂CO₃ in MeOH to cleave the ester moiety. MS(m/e): 430.0 (M+H).

Example 35

1-(2-tert-butyl-9-ethylpurin-6-yl)pyrrolidin-3-ol

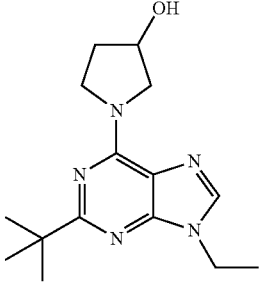 [SMILES: CCn1cnc2c(N3CCC(O)C3)nc(C(C)(C)C)nc21]

In analogy to the procedure described for the synthesis of 2-tert-butyl-9-[(4-chlorophenyl)methyl]-6-(3,3-difluoropyr-rolidin-1-yl)purine (example 1) the title compound was prepared from Acetic acid 1-(2-tert-butyl-9H-purin-6-yl)-pyrrolidin-3-yl ester (example 22, step a) and iodo-ethane plus subsequent treatment of the crude mixture/residue with K₂CO₃ in MeOH to cleave the ester moiety. MS(m/e): 290.0 (M+H).

Example 36

1-(2-tert-butyl-9-propylpurin-6-yl)pyrrolidin-3-ol

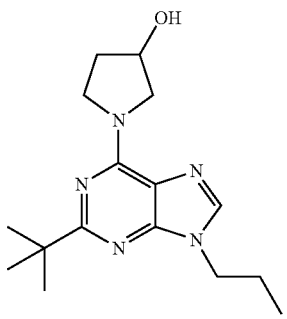 [SMILES: CCCn1cnc2c(N3CCC(O)C3)nc(C(C)(C)C)nc21]

In analogy to the procedure described for the synthesis of 2-tert-butyl-9-[(4-chlorophenyl)methyl]-6-(3,3-difluoropyr-rolidin-1-yl)purine (example 1) the title compound was prepared from Acetic acid 1-(2-tert-butyl-9H-purin-6-yl)-pyrrolidin-3-yl ester (example 22, step a) and iodo-propane plus subsequent treatment of the crude mixture/residue with K₂CO₃ in MeOH to cleave the ester moiety. MS(m/e): 304.0 (M+H).

Example 37

1-[2-tert-butyl-9-(2-methoxyethyl)purin-6-yl]pyrrolidin-3-ol

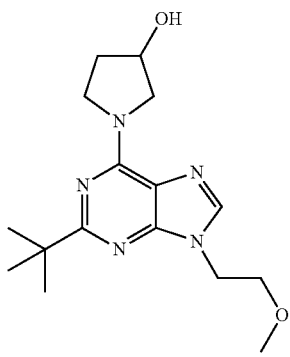 [SMILES: COCCn1cnc2c(N3CCC(O)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 1-iodo-2-methoxy-ethane plus subsequent treatment of the crude mixture/residue with K$_2$CO$_3$ in MeOH to cleave the ester moiety. MS(m/e): 320.2 (M+H).

Example 38

1-[2-tert-butyl-9-(2-phenylethyl)purin-6-yl]pyrrolidin-3-ol

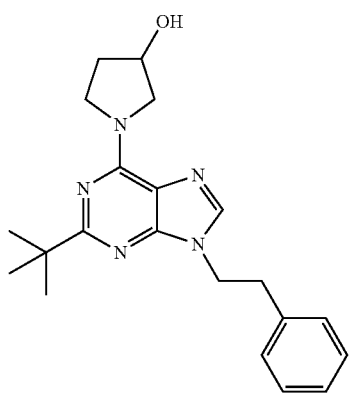 [SMILES: CC(C)(C)c1nc(N2CCC(O)C2)c2ncn(CCc3ccccc3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 2-(bromoethyl)-benzene plus subsequent treatment of the crude mixture/residue with K$_2$CO$_3$ in MeOH to cleave the ester moiety. MS(m/e): 365.9 (M+H).

Example 39

1-[2-tert-butyl-9-[(4-methylphenyl)methyl]purin-6-yl]pyrrolidin-3-ol

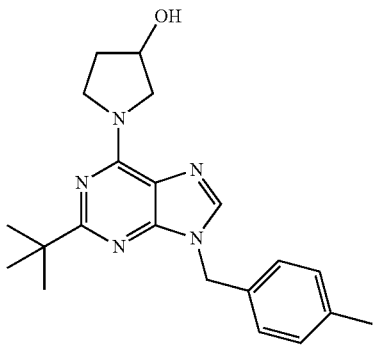 [SMILES: Cc1ccc(Cn2cnc3c(N4CCC(O)C4)nc(C(C)(C)C)nc32)cc1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 1-bromomethyl-4-methyl-benzene plus subsequent treatment of the crude mixture/residue with K$_2$CO$_3$ in MeOH to cleave the ester moiety. MS(m/e): 365.9 (M+H).

Example 40

1-[2-tert-butyl-9-(cyclohexylmethyl)purin-6-yl]pyrrolidin-3-ol

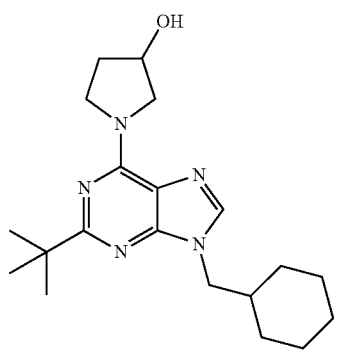 [SMILES: CC(C)(C)c1nc(N2CCC(O)C2)c2ncn(CC3CCCCC3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and bromomethyl-cyclohexane plus subsequent treatment of the crude mixture/residue with K$_2$CO$_3$ in MeOH to cleave the ester moiety. MS(m/e): 358.0 (M+H).

Example 41

2-tert-butyl-6-(3,3-difluoropyrrolidin-1-yl)-9-[[3-(trifluoromethyl)-1H-pyrazol-4-yl]methyl]purine

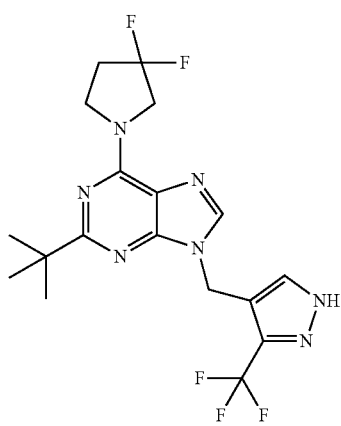 [SMILES: CC(C)(C)c1nc(N2CCC(F)(F)C2)c2ncn(Cc3c[nH]nc3C(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3-difluoro-pyrrolidin-1-yl)-9H-purine (example 1, step d) and 4-bromomethyl-3-trifluoromethyl-1-trityl-1H-pyrazole. MS(m/e): 430.0 (M+H).

Example 42

1-[2-tert-butyl-9-[(2-chloro-4-fluorophenyl)methyl]purin-6-yl]pyrrolidin-3-ol

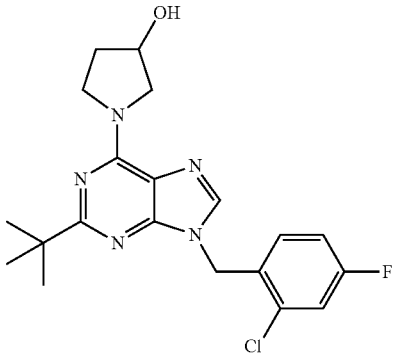 [SMILES: CC(C)(C)c1nc(N2CCC(O)C2)c2ncn(Cc3ccc(F)cc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 1-bromomethyl-2-chloro-4-fluoro-benzene plus subsequent treatment of the crude mixture/residue with K₂CO₃ in MeOH to cleave the ester moiety. MS(m/e): 404.2 (M+H).

Example 43

1-[2-tert-butyl-9-[(4-methyl-1,2,5-oxadiazol-3-yl)methyl]purin-6-yl]pyrrolidin-3-ol

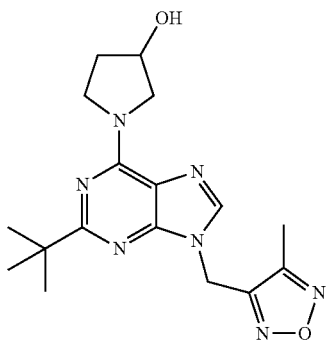 [SMILES: Cc1nonc1Cn1cnc2c(N3CCC(O)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 3-chloromethyl-4-methyl-furazan plus subsequent treatment of the crude mixture/residue with K₂CO₃ in MeOH to cleave the ester moiety. MS(m/e): 358.4 (M+H).

Example 44

1-[2-tert-butyl-9-[[3-(trifluoromethyl)-1H-pyrazol-4-yl]methyl]purin-6-yl]pyrrolidin-3-ol

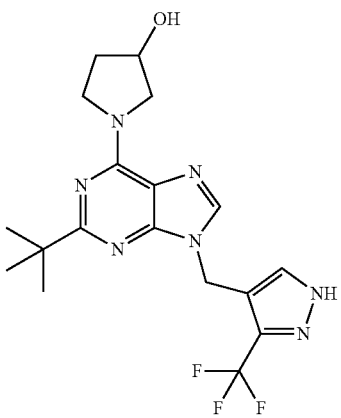 [SMILES: CC(C)(C)c1nc(N2CCC(O)C2)c2ncn(Cc3c[nH]nc3C(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 4-bromomethyl-3-trifluoromethyl-1-trityl-1H-pyrazole plus subsequent treatment of the crude mixture/residue with K₂CO₃ in MeOH to cleave the ester moiety. Subsequently the trityl-protecting group was cleaved with TFA. MS(m/e): 410.0 (M+H).

Example 45

1-[2-tert-butyl-9-(3,3,3-trifluoropropyl)purin-6-yl]pyrrolidin-3-ol

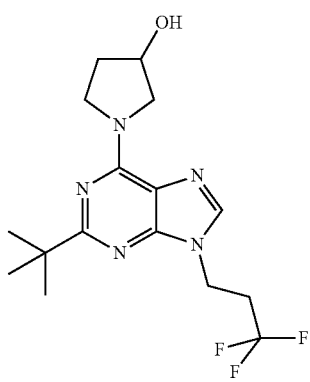 [SMILES: CC(C)(C)c1nc(N2CCC(O)C2)c2ncn(CCC(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 1,1,1-trifluoro-3-iodo-propane plus subsequent treatment of the crude mixture/residue with K$_2$CO$_3$ in MeOH to cleave the ester moiety. MS(m/e): 358.0 (M+H).

Example 46

1-[2-tert-butyl-9-(oxolan-3-yl)purin-6-yl]pyrrolidin-3-ol

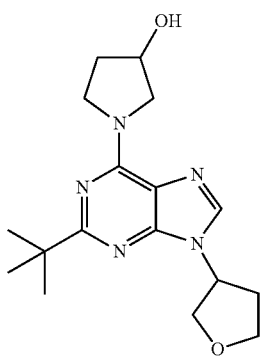 [SMILES: CC(C)(C)c1nc(N2CCC(O)C2)c2ncn(C3CCOC3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 3-bromotetrahydrofuran plus subsequent treatment of the crude mixture/residue with K$_2$CO$_3$ in MeOH to cleave the ester moiety. MS(m/e): 332.2 (M+H).

Example 47

2-[2-tert-butyl-6-(3-hydroxypyrrolidin-1-yl)purin-9-yl]-1-(2-chlorophenyl)ethanone

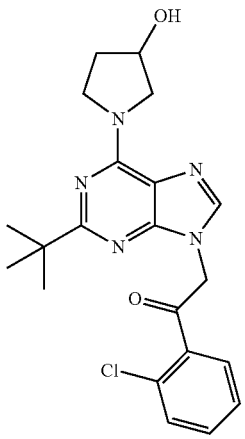 [SMILES: CC(C)(C)c1nc(N2CCC(O)C2)c2ncn(CC(=O)c3ccccc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-pyrrolidin-3-yl ester (example 22, step a) and 2-bromo-1-(2-chloro-phenyl)-ethanone plus subsequent treatment of the crude mixture/residue with K$_2$CO$_3$ in MeOH to cleave the ester moiety. MS(m/e): 414.0 (M+H).

Example 48

N—{(S)-1-[2-tert-Butyl-9-(2-chloro-benzyl)-9H-purin-6-yl]-pyrrolidin-3-yl}-acetamide

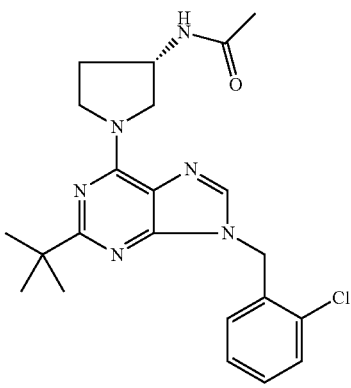 [SMILES: CC(=O)N[C@H]1CCN(c2nc(C(C)(C)C)nc3c2ncn3Cc2ccccc2Cl)C1]

a) N—[(S)-1-(2-tert-Butyl-9H-purin-6-yl)-pyrrolidin-3-yl]-acetamide

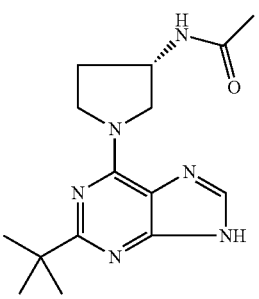 [SMILES: CC(=O)N[C@H]1CCN(c2nc(C(C)(C)C)nc3[nH]cnc23)C1]

To a solution of 2-tert-butyl-6-chloro-9H-purine (600 mg, 2.857 mmol) and (S)—N-pyrrolidin-3-yl-acetamide (402.28 mg, 3.143 mmol) in EtOH (30 mL) was added DIPEA (1.49 ml, 8.571 mmol), and the resultant reaction mixture was stirred at 100° C. for 16 h. Volatilities were evaporated and the residue was diluted with DCM (200 mL) and washed with water (2×75 mL). The organic layer was dried over anhydrous Na$_2$SO$_4$, filtered and evaporated. The residue was purified by column chromatography over silica gel (30-40% EtOAc/hexane) to yield the title compound (660 mg, 76%) as off white solid. MS(m/e): 303.0 (M+H).

b) N—{(S)-1-[2-tert-Butyl-9-(2-chloro-benzyl)-9H-purin-6-yl]-pyrrolidin-3-yl}-acetamide In analogy to the procedure described for the synthesis of 2-tert-butyl-9-[(4-chlorophenyl)methyl]-6-(3,3-difluoropyrrolidin-1-yl)purine (example 1) the title compound was prepared from N—[(S)-1-(2-tert-Butyl-9H-purin-6-yl)-pyrrolidin-3-yl]-acetamide (example 4, step a) and 1-bromomethyl-2-chloro-benzene. MS(m/e): 427.4 (M+H).

Example 49

N—[(S)-1-[2-tert-butyl-9-[(3-chlorophenyl)methyl]purin-6-yl]pyrrolidin-3-yl]acetamide

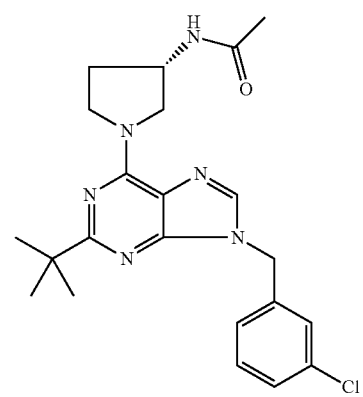 [SMILES: CC(=O)N[C@H]1CCN(c2nc(C(C)(C)C)nc3c2ncn3Cc2cccc(Cl)c2)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from N—[(S)-1-(2-tert-Butyl-9H-purin-6-yl)-pyrrolidin-3-yl]-acetamide (example 48, step a) and 1-bromomethyl-3-chloro-benzene. MS(m/e): 427.4 (M+H).

Example 50

N—[(S)-1-[2-tert-butyl-9-[(4-chlorophenyl)methyl]purin-6-yl]pyrrolidin-3-yl]acetamide

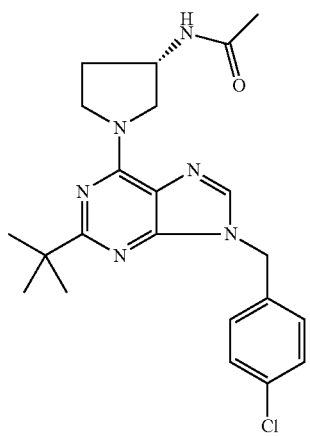 [SMILES: CC(=O)N[C@H]1CCN(c2nc(C(C)(C)C)nc3c2ncn3Cc2ccc(Cl)cc2)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from N—[(S)-1-(2-tert-Butyl-9H-purin-6-yl)-pyrrolidin-3-yl]-acetamide (example 48, step a) and 1-bromomethyl-4-chloro-benzene. MS(m/e): 427.0 (M+H).

Example 51

N—[(S)-1-[2-tert-butyl-9-[[2-(trifluoromethyl)phenyl]methyl]purin-6-yl]pyrrolidin-3-yl]acetamide

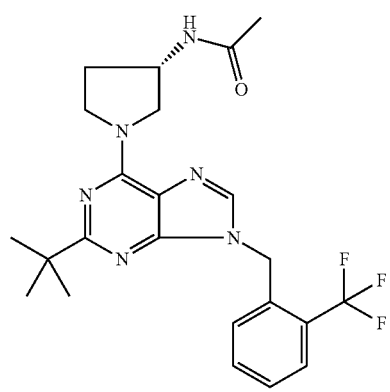 [SMILES: CC(=O)N[C@H]1CCN(c2nc(C(C)(C)C)nc3c2ncn3Cc2ccccc2C(F)(F)F)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from N—[(S)-1-(2-tert-Butyl-9H-purin-6-yl)-pyrrolidin-3-yl]-acetamide (example 48, step a) and 1-bromomethyl-2-trifluoromethyl-benzene. MS(m/e): 461.2 (M+H).

Example 52

N—[(S)-1-[2-tert-butyl-9-[(2-methylsulfonylphenyl)methyl]purin-6-yl]pyrrolidin-3-yl]acetamide

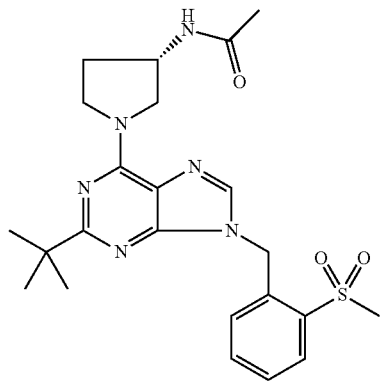 [SMILES: CC(=O)N[C@H]1CCN(c2nc(C(C)(C)C)nc3c2ncn3Cc2ccccc2S(C)(=O)=O)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from N—[(S)-1-(2-tert-Butyl-9H-purin-6-yl)-pyrrolidin-3-yl]-acetamide (example 48, step a) and 1-bromomethyl-2-methanesulfonyl-benzene. MS(m/e): 471.2 (M+H).

Example 53

N—[(S)-1-[2-tert-butyl-9-[(2-chloropyridin-3-yl)methyl]purin-6-yl]pyrrolidin-3-yl]acetamide

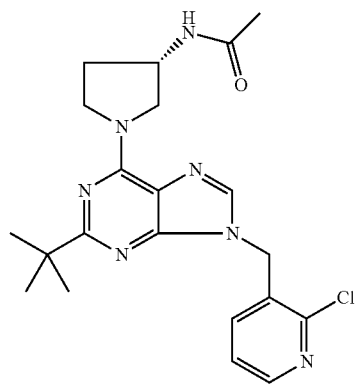 [SMILES: CC(=O)N[C@H]1CCN(c2nc(C(C)(C)C)nc3c2ncn3Cc2cccnc2Cl)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from N—[(S)-1-(2-tert-Butyl-9H-purin-6-yl)-pyrrolidin-3-yl]-acetamide (example 48, step a) and 2-chloro-3-chloromethyl-pyridine. MS(m/e): 428.2 (M+H).

Example 54

N—[(S)-1-[2-tert-butyl-9-[(3-chloropyridin-2-yl)methyl]purin-6-yl]pyrrolidin-3-yl]acetamide

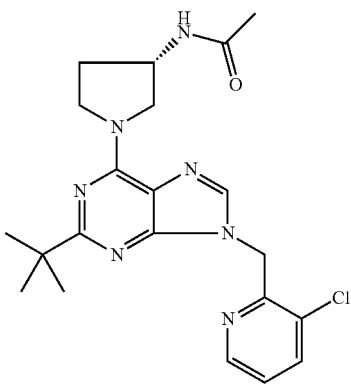 [SMILES: CC(=O)N[C@H]1CCN(c2nc(C(C)(C)C)nc3c2ncn3Cc2ncccc2Cl)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from N—[(S)-1-(2-tert-Butyl-9H-purin-6-yl)-pyrrolidin-3-yl]-acetamide (example 48, step a) and 3-chloro-2-chloromethyl-pyridine. MS(m/e): 428.2 (M+H).

Example 55

N—[(S)-1-[2-tert-butyl-9-[(4-methyl-1,2,5-oxadiazol-3-yl)methyl]purin-6-yl]pyrrolidin-3-yl]acetamide

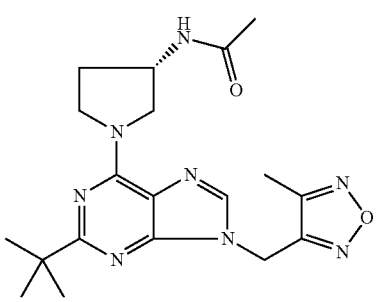 [SMILES: CC(=O)N[C@H]1CCN(c2nc(C(C)(C)C)nc3c2ncn3Cc2nonc2C)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from N—[(S)-1-(2-tert-Butyl-9H-purin-6-yl)-pyrrolidin-3-yl]-acetamide (example 48, step a) and 2-chloromethyl-5-methyl-[1,3,4]oxadiazole. MS(m/e): 399.0 (M+H).

Example 56

7-[2-tert-butyl-9-[(2-chlorophenyl)methyl]purin-6-yl]-2-oxa-7-azaspiro[3.4]octane

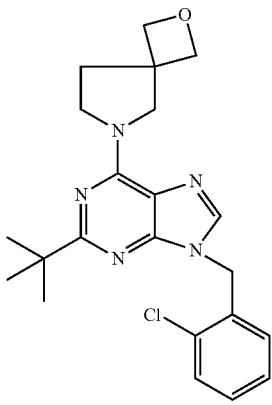 [SMILES: CC(C)(C)c1nc(N2CCC3(COC3)C2)c2ncn(Cc3ccccc3Cl)c2n1]

a) 2-tert-Butyl-6-(2-oxa-6-aza-spiro[3.4]oct-6-yl)-9H-purine

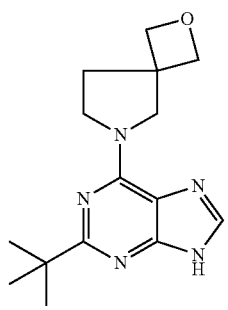 [SMILES: CC(C)(C)c1nc(N2CCC3(COC3)C2)c2nc[nH]c2n1]

In analogy to the procedure described for the synthesis of N—[(S)-1-(2-tert-Butyl-9H-Aurin-6-yl)-pyrrolidin-3-yl]-acetamide (example 48, a) the title compounds was prepared from 2-tert-butyl-6-chloro-9H-purine and 2-oxa-6-aza-spiro[3.4]octane. MS(m/e): 288.0 (M+H).

b) 7-[2-tert-butyl-9-[(2-chlorophenyl)methyl]purin-6-yl]-2-oxa-7-azaspiro[3.4]octane In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(2-oxa-6-aza-spiro[3.4]oct-6-yl)-9H-purine (example 56, step a) and 1-bromomethyl-2-chloro-benzene. MS(m/e): 412.4 (M+H).

Example 57

7-[2-tert-butyl-9-[(3-chlorophenyl)methyl]purin-6-yl]-2-oxa-7-azaspiro[3.4]octane

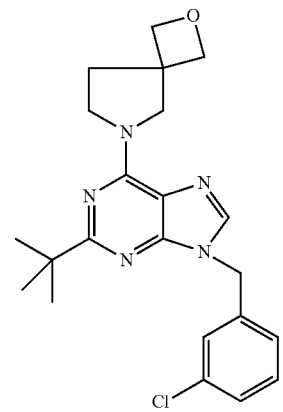 [SMILES: CC(C)(C)c1nc(N2CCC3(COC3)C2)c2ncn(Cc3cccc(Cl)c3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(2-oxa-6-aza-spiro[3.4]oct-6-yl)-9H-purine (example 56, step a) and 1-bromomethyl-3-chloro-benzene. MS(m/e): 412.2 (M+H).

Example 58

7-[2-tert-butyl-9-[(4-chlorophenyl)methyl]purin-6-yl]-2-oxa-7-azaspiro[3.4]octane

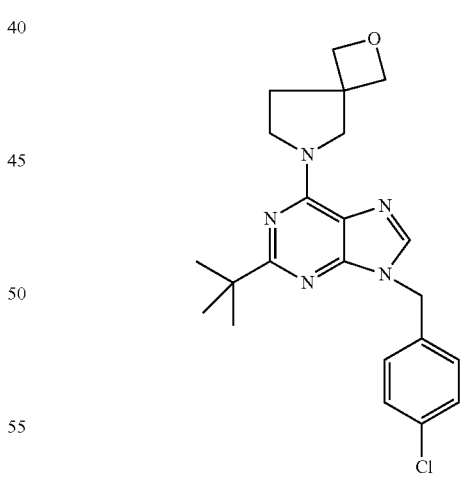

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(2-oxa-6-aza-spiro[3.4]oct-6-yl)-9H-purine (example 56, step a) and 1-bromomethyl-4-chloro-benzene. MS(m/e): 412.2 (M+H).

Example 59

7-[2-tert-butyl-9-[[2-(trifluoromethyl)phenyl]methyl]purin-6-yl]-2-oxa-7-azaspiro[3.4]octane

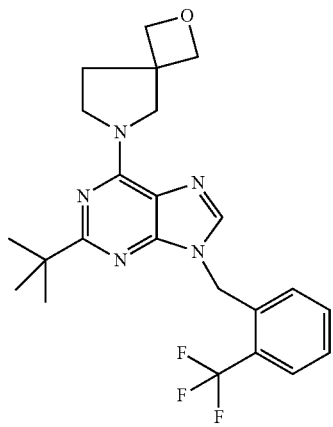 [SMILES: CC(C)(C)c1nc(N2CCC3(COC3)C2)c2ncn(Cc3ccccc3C(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(2-oxa-6-aza-spiro[3.4]oct-6-yl)-9H-purine (example 56, step a) and 1-bromomethyl-2-trifluoromethyl-benzene. MS(m/e): 446.0 (M+H).

Example 60

7-[2-tert-butyl-9-[(2-methylsulfonylphenyl)methyl]purin-6-yl]-2-oxa-7-azaspiro[3.4]octane

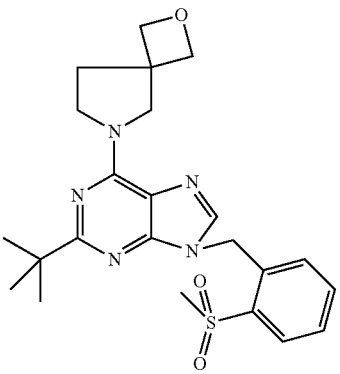 [SMILES: CC(C)(C)c1nc(N2CCC3(COC3)C2)c2ncn(Cc3ccccc3S(C)(=O)=O)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(2-oxa-6-aza-spiro[3.4]oct-6-yl)-9H-purine (example 56, step a) and 1-bromomethyl-2-methanesulfonyl-benzene. MS(m/e): 456.0 (M+H).

Example 61

7-[2-tert-butyl-9-[(2-chloropyridin-3-yl)methyl]purin-6-yl]-2-oxa-7-azaspiro[3.4]octane

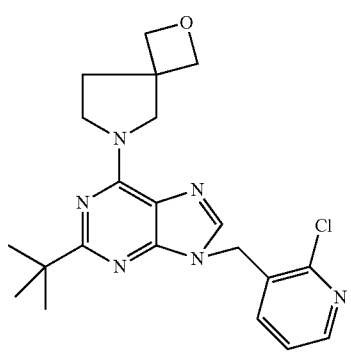 [SMILES: CC(C)(C)c1nc(N2CCC3(COC3)C2)c2ncn(Cc3cccnc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(2-oxa-6-aza-spiro[3.4]oct-6-yl)-9H-purine (example 56, step a) and 2-Chloro-3-chloromethyl-pyridine. MS(m/e): 413.2 (M+H).

Example 62

7-[2-tert-butyl-9-[(4-methyl-1,2,5-oxadiazol-3-yl)methyl]purin-6-yl]-2-oxa-7-azaspiro[3.4]octane

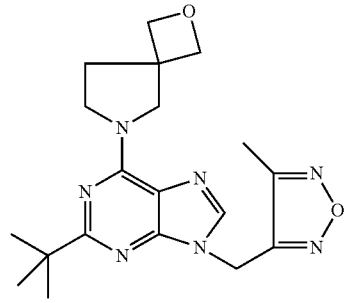 [SMILES: Cc1nonc1Cn1cnc2c(N3CCC4(COC4)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(2-oxa-6-aza-spiro[3.4]oct-6-yl)-9H-purine (example 56, step a) and 3-Chloromethyl-4-methyl-furazan. MS(m/e): 384.2 (M+H).

Example 63

7-[2-tert-butyl-9-(2-methoxyethyl)purin-6-yl]-2-oxa-7-azaspiro[3.4]octane

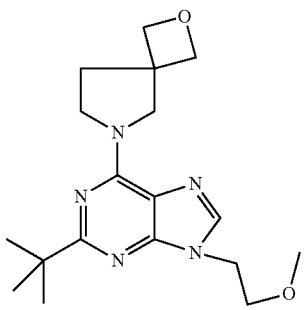 [SMILES: COCCn1cnc2c(N3CCC4(COC4)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(2-oxa-6-aza-spiro[3.4]oct-6-yl)-9H-purine (example 56, step a) and 1-bromo-2-methoxy-ethane. MS(m/e): 346.0 (M+H).

Example 64

1-[2-tert-butyl-9-[(2-chlorophenyl)methyl]purin-6-yl]-3-methylpyrrolidin-3-ol

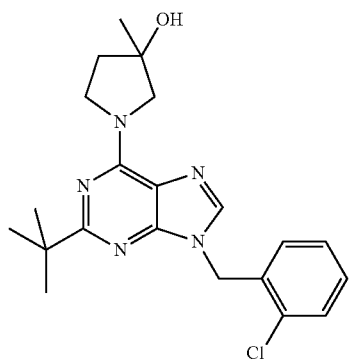 [SMILES: CC1(O)CCN(c2nc(C(C)(C)C)nc3c2ncn3Cc2ccccc2Cl)C1]

a) Acetic acid 1-(2-tert-butyl-9H-purin-6-yl)-3-methyl-pyrrolidin-3-yl ester

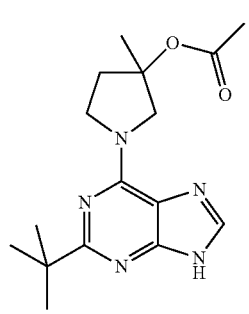 [SMILES: CC(=O)OC1(C)CCN(c2nc(C(C)(C)C)nc3[nH]cnc23)C1]

In analogy to the procedure described for the synthesis of N—[(S)-1-(2-tert-Butyl-9H-purin-6-yl)-pyrrolidin-3-yl]-acetamide (example 48, a) the title compounds was prepared from 2-tert-butyl-6-chloro-9H-purine and acetic acid 3-methyl-pyrrolidin-3-yl ester. MS(m/e): 317.8 (M+H).

b) 1-[2-tert-butyl-9-[(2-chlorophenyl)methyl]purin-6-yl]-3-methylpyrrolidin-3-ol In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 1-bromomethyl-2-chloro-benzene. MS(m/e): 400.0 (M+H).

Example 65

1-[2-tert-butyl-9-[(3-chlorophenyl)methyl]purin-6-yl]-3-methylpyrrolidin-3-ol

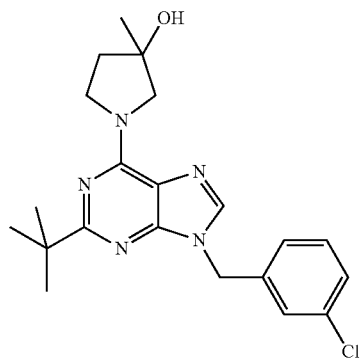 [SMILES: CC1(O)CCN(c2nc(C(C)(C)C)nc3c2ncn3Cc2cccc(Cl)c2)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 1-bromomethyl-3-chloro-benzene. MS(m/e): 400.0 (M+H).

Example 66

1-[2-tert-butyl-9-[(4-chlorophenyl)methyl]purin-6-yl]-3-methylpyrrolidin-3-ol

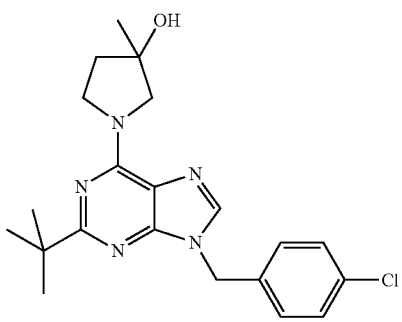 [SMILES: CC1(O)CCN(c2nc(C(C)(C)C)nc3c2ncn3Cc2ccc(Cl)cc2)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 1-bromomethyl-4-chloro-benzene. MS(m/e): 400.0 (M+H).

Example 67

1-[2-tert-butyl-9-[[2-(trifluoromethyl)phenyl]methyl]purin-6-yl]-3-methylpyrrolidin-3-ol

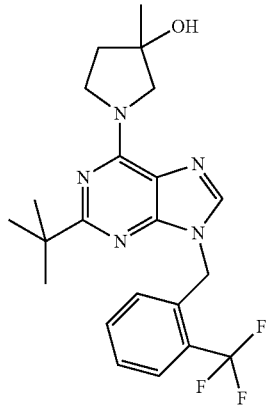 [SMILES: CC1(O)CCN(c2nc(C(C)(C)C)nc3c2ncn3Cc2ccccc2C(F)(F)F)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 1-bromomethyl-2-trifluoromethyl-benzene. MS(m/e): 434.0 (M+H).

Example 68

1-[2-tert-butyl-9-[(2-chloropyridin-3-yl)methyl]purin-6-yl]-3-methylpyrrolidin-3-ol

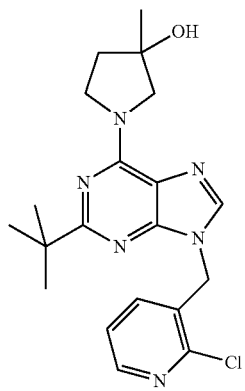 [SMILES: CC1(O)CCN(c2nc(C(C)(C)C)nc3c2ncn3Cc2cccnc2Cl)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 2-chloro-3-chloromethyl-pyridine. MS(m/e): 401.0 (M+H).

Example 69

1-[2-tert-butyl-9-[(3-chloropyridin-2-yl)methyl]purin-6-yl]-3-methylpyrrolidin-3-ol

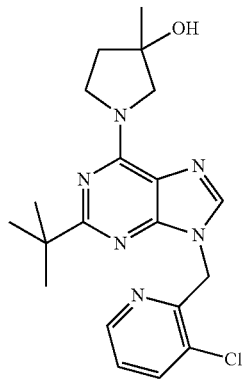 [SMILES: CC1(O)CCN(c2nc(C(C)(C)C)nc3c2ncn3Cc2ncccc2Cl)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 3-chloro-2-chloromethyl-pyridine. MS(m/e): 401.0 (M+H).

Example 70

1-[2-tert-butyl-9-[(4-methyl-1,2,5-oxadiazol-3-yl)methyl]purin-6-yl]-3-methylpyrrolidin-3-ol

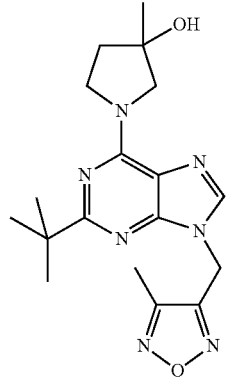 [SMILES: Cc1nonc1Cn1cnc2c(N3CCC(C)(O)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 3-chloromethyl-4-methyl-furazan. MS(m/e): 372.2 (M+H).

Example 71

1-[2-tert-butyl-9-(2-methoxyethyl)purin-6-yl]-3-methylpyrrolidin-3-ol

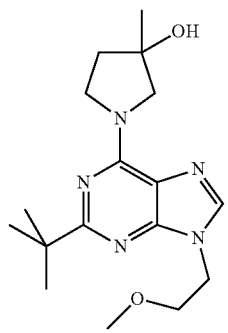 [SMILES: COCCn1cnc2c(N3CCC(C)(O)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 1-bromo-2-methoxy-ethane. MS(m/e): 334.0 (M+H).

Example 72

2-tert-butyl-9-[(2-chlorophenyl)methyl]-6-(3,3,4,4-tetrafluoropyrrolidin-1-yl)purine

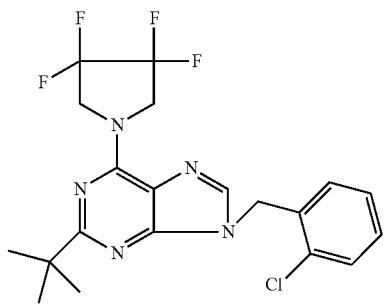 [SMILES: CC(C)(C)c1nc(N2CC(F)(F)C(F)(F)C2)c2ncn(Cc3ccccc3Cl)c2n1]

a) 2-tert-Butyl-6-(3,3,4,4-tetrafluoro-pyrrolidin-1-yl)-9H-purine

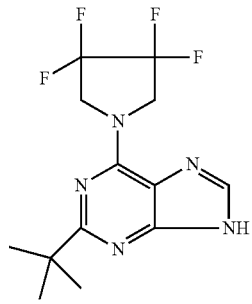 [SMILES: CC(C)(C)c1nc(N2CC(F)(F)C(F)(F)C2)c2nc[nH]c2n1]

In analogy to the procedure described for the synthesis of N—[(S)-1-(2-tert-Butyl-9H-purin-6-yl)-pyrrolidin-3-yl]-acetamide (example 48, a) the title compounds was prepared from 2-tert-butyl-6-chloro-9H-purine and 3, 3, 4, 4-tetrafluoro-pyrrolidine. MS(m/e): 318.0 (M+H).

b) 2-tert-butyl-9-[(2-chlorophenyl)methyl]-6-(3,3,4,4-tetrafluoropyrrolidin-1-yl)purine In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3,4,4-tetrafluoro-pyrrolidin-1-yl)-9H-purine (example 72, step a) and 1-bromomethyl-2-chloro-benzene. MS(m/e): 442.3 (M+H).

Example 73

2-tert-butyl-9-[(3-chlorophenyl)methyl]-6-(3,3,4,4-tetrafluoropyrrolidin-1-yl)purine

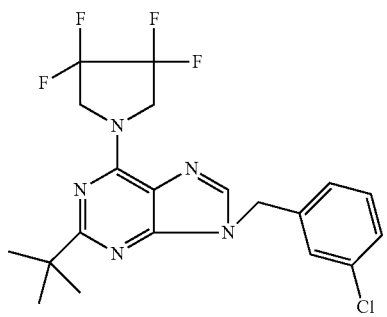 [SMILES: CC(C)(C)c1nc(N2CC(F)(F)C(F)(F)C2)c2ncn(Cc3cccc(Cl)c3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3,4,4-tetrafluoro-pyrrolidin-1-yl)-9H-purine (example 72, step a) and 1-bromomethyl-3-chloro-benzene. MS(m/e): 441.2 (M+H).

Example 74

1-[2-tert-butyl-9-[(2-methylsulfonylphenyl)methyl]purin-6-yl]-3-methylpyrrolidin-3-ol

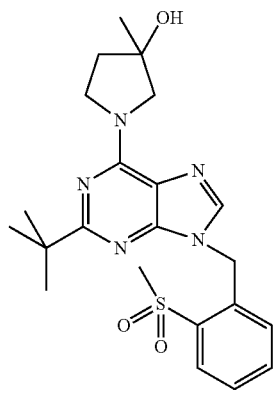 [SMILES: CC1(O)CCN(c2nc(C(C)(C)C)nc3c2ncn3Cc2ccccc2S(C)(=O)=O)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 1-bromomethyl-2-methanesulfonyl-benzene. MS(m/e): 444.2 (M+H).

Example 75

N—[(S)-1-[2-tert-butyl-9-[[3-(trifluoromethyl)-1H-pyrazol-4-yl]methyl]purin-6-yl]pyrrolidin-3-yl]acetamide

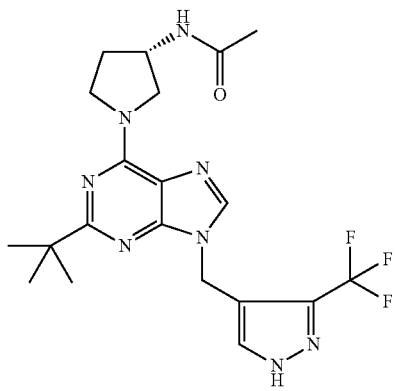 [SMILES: CC(=O)N[C@H]1CCN(c2nc(C(C)(C)C)nc3c2ncn3Cc2c[nH]nc2C(F)(F)F)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from N—[(S)-1-(2-tert-Butyl-9H-purin-6-yl)-pyrrolidin-3-yl]-acetamide (example 48, step a) and 4-bromomethyl-3-trifluoromethyl-1-trityl-1H-pyrazole with subsequent cleavage of the trityl protecting group with TFA. MS(m/e): 451.2 (M+H).

Example 76

7-[2-tert-butyl-9-[[3-(trifluoromethyl)-1H-pyrazol-4-yl]methyl]purin-6-yl]-2-oxa-7-azaspiro[3.4]octane

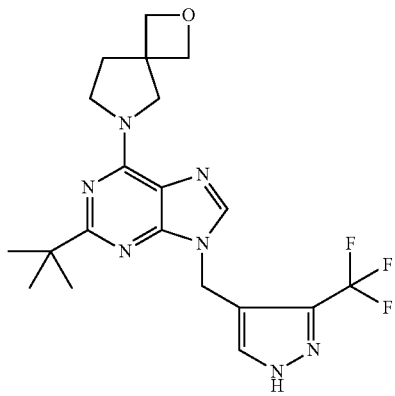 [SMILES: CC(C)(C)c1nc(N2CCC3(COC3)C2)c2ncn(Cc3c[nH]nc3C(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(2-oxa-6-aza-spiro[3.4]oct-6-yl)-9H-purine (example 56 step a) and 4-bromomethyl-3-trifluoromethyl-1-trityl-1H-pyrazole with subsequent cleavage of the trityl protecting group with TFA. MS(m/e): 436.2 (M+H).

Example 77

N—[(S)-1-[2-tert-butyl-9-[[4-(trifluoromethyl)-1H-pyrazol-3-yl]methyl]purin-6-yl]pyrrolidin-3-yl]acetamide

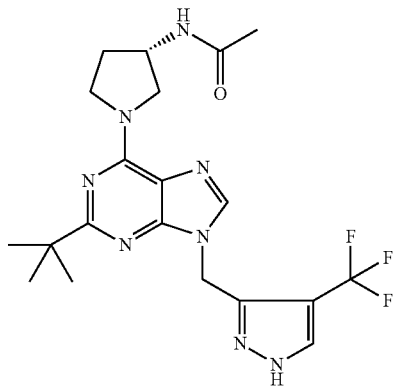 [SMILES: CC(=O)N[C@H]1CCN(c2nc(C(C)(C)C)nc3c2ncn3Cc2n[nH]cc2C(F)(F)F)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from N—[(S)-1-(2-tert-Butyl-9H-purin-6-yl)-pyrrolidin-3-yl]-acetamide (example 48, step a) and 3-bromomethyl-4-trifluoromethyl-1-trityl-1H-pyrazole with subsequent cleavage of the trityl protecting group with TFA. MS(m/e): 451.0 (M+H).

Example 78

7-[2-tert-butyl-9-[[4-(trifluoromethyl)-1H-pyrazol-3-yl]methyl]purin-6-yl]-2-oxa-7-azaspiro[3.4]octane

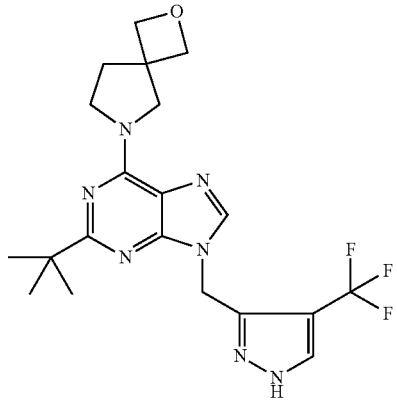 [SMILES: CC(C)(C)c1nc(N2CCC3(COC3)C2)c2ncn(Cc3n[nH]cc3C(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(2-oxa-6-aza-spiro[3.4]oct-6-yl)-9H-purine (example 56 step a) and 4-bromomethyl-3- trifluoromethyl-1-trityl-1H-pyrazole with subsequent cleavage of the trityl protecting group with TFA. MS(m/e): 436.2 (M+H).

Example 79

2-[[2-tert-butyl-6-(3,3,4,4-tetrafluoropyrrolidin-1-yl)purin-9-yl]methyl]-5-methyl-1,3,4-oxadiazole

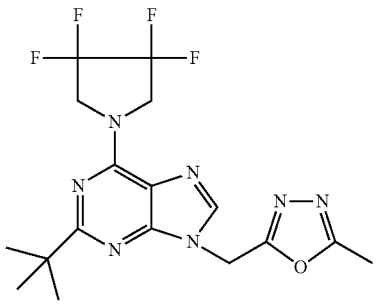 [SMILES: Cc1nnc(Cn2cnc3c(N4CC(F)(F)C(F)(F)C4)nc(C(C)(C)C)nc32)o1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3,4,4-tetrafluoro-pyrrolidin-1-yl)-9H-purine (example 72, step a) and 2-chloromethyl-5-methyl-[1,3,4]oxadiazole. MS(m/e): 413.8 (M+H).

Example 80

5-[[2-tert-butyl-6-(3,3,4,4-tetrafluoropyrrolidin-1-yl)purin-9-yl]methyl]-3-methyl-1,2,4-oxadiazole

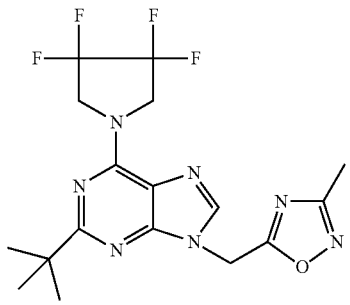 [SMILES: Cc1noc(Cn2cnc3c(N4CC(F)(F)C(F)(F)C4)nc(C(C)(C)C)nc32)n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3,4,4-tetrafluoro-pyrrolidin-1-yl)-9H-purine (example 72, step a) and 5-chloromethyl-3-methyl-[1,2,4]oxadiazole. MS(m/e): 414.0 (M+H).

Example 81

2-tert-butyl-9-[(1-methyltetrazol-5-yl)methyl]-6-(3,3,4,4-tetrafluoropyrrolidin-1-yl)purine

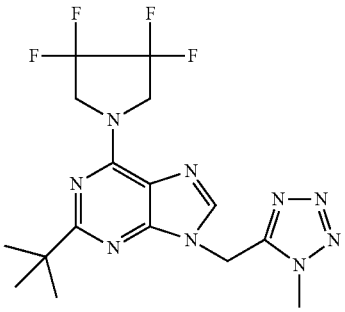 [SMILES: Cn1nnnc1Cn1cnc2c(N3CC(F)(F)C(F)(F)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3,4,4-tetrafluoro-pyrrolidin-1-yl)-9H-purine (example 72, step a) and 5-chloromethyl-1-methyl-1H-tetrazole. MS(m/e): 414.2 (M+H).

Example 82

3-[[2-tert-butyl-6-(3,3,4,4-tetrafluoropyrrolidin-1-yl)purin-9-yl]methyl]-4-methyl-1,2,5-oxadiazole

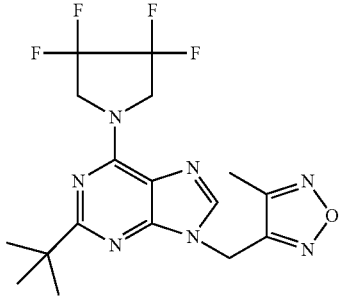 [SMILES: Cc1nonc1Cn1cnc2c(N3CC(F)(F)C(F)(F)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3,4,4-tetrafluoro-pyrrolidin-1-yl)-9H-purine (example 72, step a) and 3-chloromethyl-4-methyl-furazan. MS(m/e): 414.2 (M+H).

Example 83

2-tert-butyl-9-(2-methoxyethyl)-6-(3,3,4,4-tetrafluoropyrrolidin-1-yl)purine

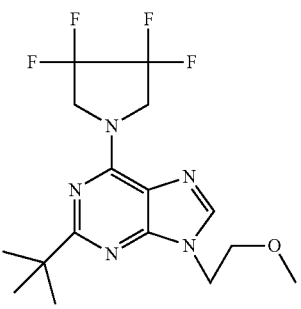 [SMILES: COCCn1cnc2c(N3CC(F)(F)C(F)(F)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3,4,4-tetrafluoro-pyrrolidin-1-yl)-9H-purine (example 72, step a) and 1-bromo-2-methoxy-ethane. MS(m/e): 376.0 (M+H).

Example 84

1-[2-tert-butyl-9-[[3-(trifluoromethyl)-1H-pyrazol-4-yl]methyl]purin-6-yl]-3-methylpyrrolidin-3-ol

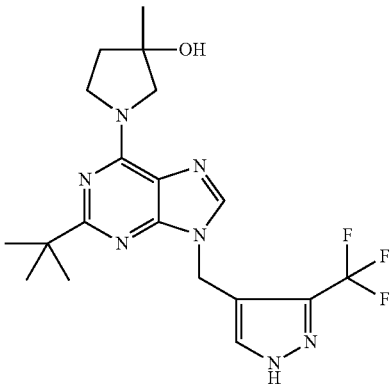 [SMILES: CC1(O)CCN(c2nc(C(C)(C)C)nc3c2ncn3Cc2c[nH]nc2C(F)(F)F)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 4-bromomethyl-3-trifluoromethyl-1-trityl-1H-pyrazole with subsequent cleavage of the trityl protecting group with TFA. MS(m/e): 424.3 (M+H).

Example 85

1-[2-tert-butyl-9-[[4-(trifluoromethyl)-1H-pyrazol-3-yl]methyl]purin-6-yl]-3-methylpyrrolidin-3-ol

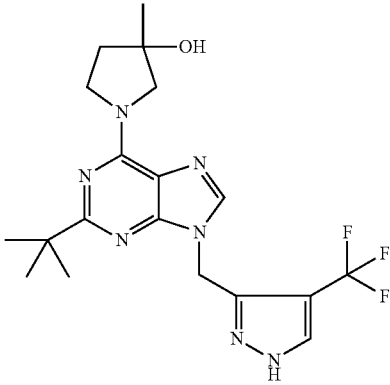

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 3-bromomethyl-4-trifluoromethyl-1-trityl-1H-pyrazole with subsequent cleavage of the trityl protecting group with TFA. MS(m/e): 424.0 (M+H).

Example 86

(3S)-1-[2-tert-butyl-9-[[2-(trifluoromethyl)phenyl]methyl]purin-6-yl]pyrrolidin-3-ol

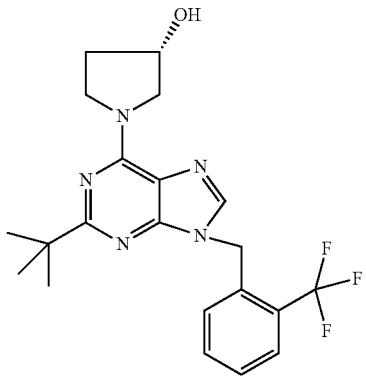 [SMILES: CC(C)(C)c1nc(N2CC[C@H](O)C2)c2ncn(Cc3ccccc3C(F)(F)F)c2n1]

a) Acetic acid (S)-1-(2-tert-butyl-9H-purin-6-yl)-pyrrolidin-3-yl ester

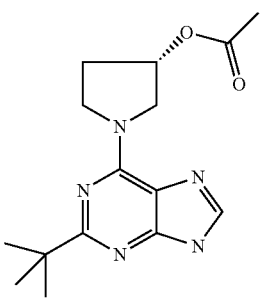 [SMILES: CC(=O)O[C@H]1CCN(c2nc(C(C)(C)C)nc3[nH]cnc23)C1]

In analogy to the procedure described for the synthesis of N—[(S)-1-(2-tert-Butyl-9H-purin-6-yl)-pyrrolidin-3-yl]-acetamide (example 48, a) the title compounds was prepared from 2-tert-butyl-6-chloro-9H-purine and acetic acid (S)-pyrrolidin-3-yl ester. MS(m/e): 303.8 (M+H).

b) (3S)-1-[2-tert-butyl-9-[[2-(trifluoromethyl)phenyl]methyl]purin-6-yl]pyrrolidin-3-ol In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 1-bromomethyl-2-chloro-benzene plus subsequent treatment of the crude mixture/residue with $K_2CO_3$ in MeOH to cleave the ester moiety. MS(m/e): 420.0 (M+H).

Example 87

(3S)-1-[2-tert-butyl-9-[(3-chlorophenyl)methyl]purin-6-yl]pyrrolidin-3-ol

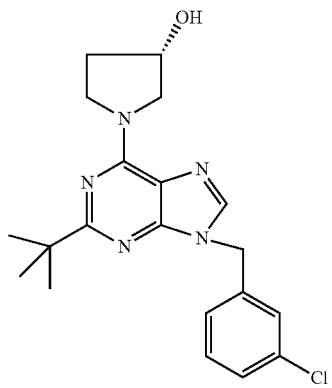 [SMILES: CC(C)(C)c1nc(N2CC[C@H](O)C2)c2ncn(Cc3cccc(Cl)c3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 1-bromomethyl-3-chloro-benzene plus subsequent treatment of the crude mixture/residue with $K_2CO_3$ in MeOH to cleave the ester moiety. MS(m/e): 386.0 (M+H).

Example 88

(3S)-1-[2-tert-butyl-9-[(4-chlorophenyl)methyl]purin-6-yl]pyrrolidin-3-ol

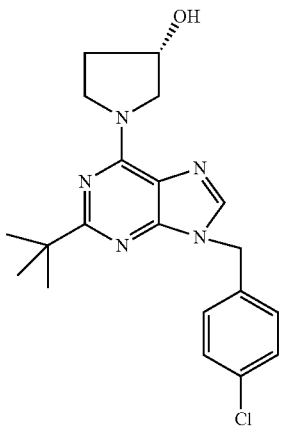 [SMILES: CC(C)(C)c1nc(N2CC[C@H](O)C2)c2ncn(Cc3ccc(Cl)cc3)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 1-bromomethyl-4-chloro-benzene plus subsequent treatment of the crude mixture/residue with $K_2CO_3$ in MeOH to cleave the ester moiety. MS(m/e): 386.0 (M+H).

Example 89

7-[2-tert-butyl-9-(3,3,3-trifluoropropyl)purin-6-yl]-2-oxa-7-azaspiro[3.4]octane

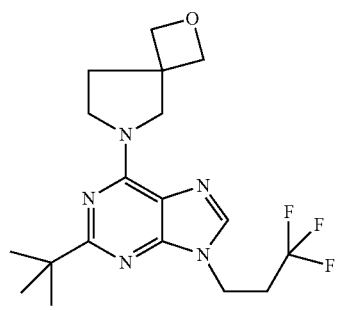 [SMILES: CC(C)(C)c1nc(N2CCC3(COC3)C2)c2ncn(CCC(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from a) 2-tert-Butyl-6-(2-oxa-6-aza-spiro[3.4]oct-6-yl)-9H-purine (example 56, step a) and 1-bromo-2-methoxy-ethane. MS(m/e): 384.0 (M+H).

Example 90

(3S)-1-[2-tert-butyl-9-[(2-methylsulfonylphenyl)methyl]purin-6-yl]pyrrolidin-3-ol

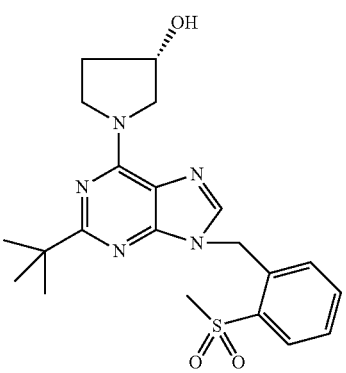 [SMILES: CC(C)(C)c1nc(N2CC[C@H](O)C2)c2ncn(Cc3ccccc3S(C)(=O)=O)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 1-bromomethyl-2-methanesulfonyl-benzene. MS(m/e): 430.2 (M+H).

Example 91

(3S)-1-[2-tert-butyl-9-[(2-chloropyridin-3-yl)methyl]purin-6-yl]pyrrolidin-3-ol

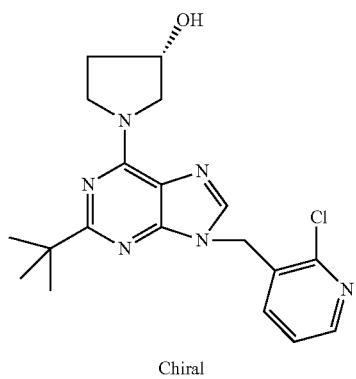 [SMILES: CC(C)(C)c1nc(N2CC[C@H](O)C2)c2ncn(Cc3cccnc3Cl)c2n1]

Chiral

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 1-bromomethyl-2-methanesulfonyl-benzene. MS(m/e): 387.2 (M+H).

Example 92

(3S)-1-[2-tert-butyl-9-[(3-chloropyridin-2-yl)methyl]purin-6-yl]pyrrolidin-3-ol

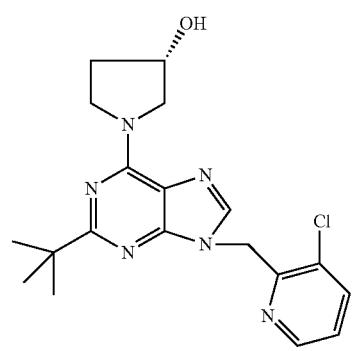 [SMILES: CC(C)(C)c1nc(N2CC[C@H](O)C2)c2ncn(Cc3ncccc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 3-chloro-2-chloromethyl-pyridine. MS(m/e): 387.2 (M+H).

Example 93

2-tert-butyl-6-(3,3,4,4-tetrafluoropyrrolidin-1-yl)-9-(3,3,3-trifluoropropyl)purine

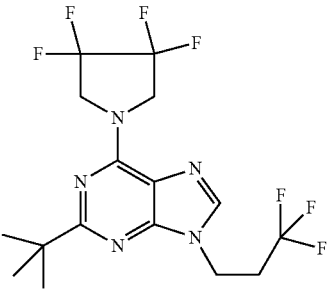 [SMILES: CC(C)(C)c1nc(N2CC(F)(F)C(F)(F)C2)c2ncn(CCC(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3,4,4-tetrafluoro-pyrrolidin-1-yl)-9H-purine (example 72, step a) and 1,1,1-trifluoro-3-iodo-propane. MS(m/e): 414.2 (M+H).

Example 94

(3S)-1-[2-tert-butyl-9-(2-methoxyethyl)purin-6-yl]pyrrolidin-3-ol

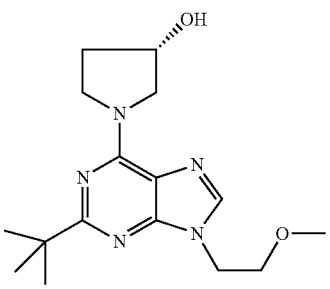 [SMILES: COCCn1cnc2c(N3CC[C@H](O)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 1-bromo-2-methoxy-ethane. MS(m/e): 320.0 (M+H).

Example 95

(3S)-1-[2-tert-butyl-9-[(1-methyltetrazol-5-yl)methyl]purin-6-yl]pyrrolidin-3-ol

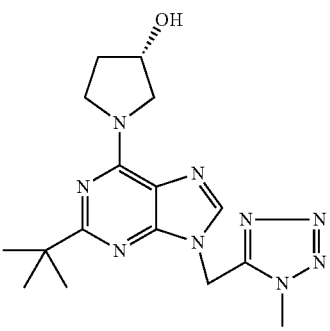 [SMILES: Cn1nnnc1Cn1cnc2c(N3CC[C@H](O)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 5-chloromethyl-1-methyl-1H-tetrazole plus subsequent treatment of the crude mixture/residue with K$_2$CO$_3$ in MeOH to cleave the ester moiety. MS(m/e): 358.2 (M+H).

Example 96

(3S)-1-[2-tert-butyl-9-[(4-methyl-1,2,5-oxadiazol-3-yl)methyl]purin-6-yl]pyrrolidin-3-ol

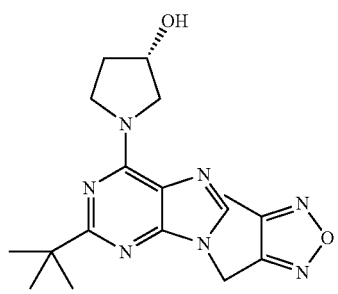 [SMILES: Cc1nonc1Cn1cnc2c(N3CC[C@H](O)C3)nc(C(C)(C)C)nc21]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 3-chloromethyl-4-methyl-furazan plus subsequent treatment of the crude mixture/residue with K$_2$CO$_3$ in MeOH to cleave the ester moiety. MS(m/e): 358.2 (M+H).

Example 97

(3S)-1-[2-tert-butyl-9-[(2-chlorophenyl)methyl]purin-6-yl]pyrrolidin-3-ol

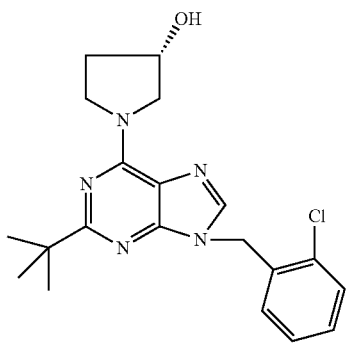 [SMILES: CC(C)(C)c1nc(N2CC[C@H](O)C2)c2ncn(Cc3ccccc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 1-bromomethyl-2-chloro-benzene plus subsequent treatment of the crude mixture/residue with K$_2$CO$_3$ in MeOH to cleave the ester moiety. MS(m/e): 386.4 (M+H).

Example 98

(3S)-1-[2-tert-butyl-9-[[3-(trifluoromethyl)-1H-pyrazol-4-yl]methyl]purin-6-yl]pyrrolidin-3-ol

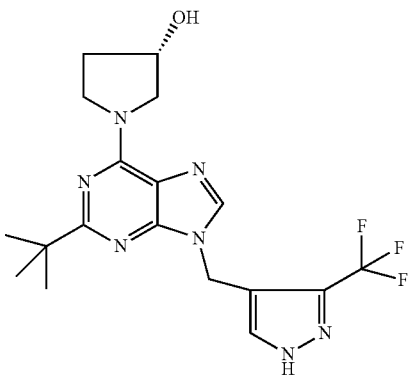 [SMILES: CC(C)(C)c1nc(N2CC[C@H](O)C2)c2ncn(Cc3c[nH]nc3C(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 4-bromomethyl-3-trifluoromethyl-1-trityl-1H-pyrazole plus subsequent treatment of the crude mixture/residue with K$_2$CO$_3$ in MeOH to cleave the ester moiety. The trityl group was subsequently cleaved with TFA. MS(m/e): 410.4 (M+H).

Example 99

(3S)-1-[2-tert-butyl-9-(3,3,3-trifluoropropyl)purin-6-yl]pyrrolidin-3-ol

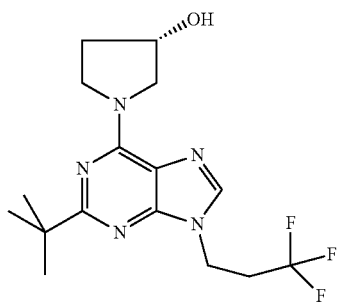 [SMILES: CC(C)(C)c1nc(N2CC[C@H](O)C2)c2ncn(CCC(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 1,1,1-trifluoro-3-iodo-propane. MS(m/e): 358.0 (M+H).

Example 100

(3S)-1-[2-tert-butyl-9-[[4-(trifluoromethyl)-1H-pyrazol-3-yl]methyl]purin-6-yl]pyrrolidin-3-ol

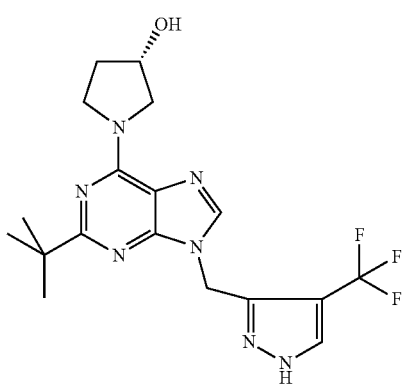 [SMILES: CC(C)(C)c1nc(N2CC[C@H](O)C2)c2ncn(Cc3n[nH]cc3C(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 3-bromomethyl-4-trifluoromethyl-1-trityl-1H-pyrazole plus subsequent treatment of the crude mixture/residue with K$_2$CO$_3$ in MeOH to cleave the ester moiety. The trityl group was subsequently cleaved with TFA. MS(m/e): 410.2 (M+H).

Example 101

(3S)-1-[2-tert-butyl-9-[(3-methyl-1,2,4-oxadiazol-5-yl)methyl]purin-6-yl]pyrrolidin-3-ol

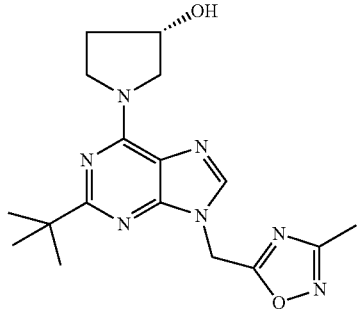 [SMILES: Cc1noc(Cn2cnc3c(N4CC[C@H](O)C4)nc(C(C)(C)C)nc32)n1]

In analogy to the procedure described for the synthesis of 2-tert-butyl-9-[(4-chlorophenyl)methyl]-6-(3,3-difluoropyrrolidin-1-yl)purine (example 1) the title compound was prepared from a) Acetic acid (S)-1-(2-tert-butyl-9H-purin-6-yl)-pyrrolidin-3-yl ester (example 86, step a) and 5-chloromethyl-3-methyl-[1,2,4]oxadiazole plus subsequent treatment of the crude mixture/residue with K$_2$CO$_3$ in MeOH to cleave the ester moiety. MS(m/e): 358.0 (M+H).

Example 102

1-[2-tert-butyl-9-(3,3,3-trifluoropropyl)purin-6-yl]-3-methylpyrrolidin-3-ol

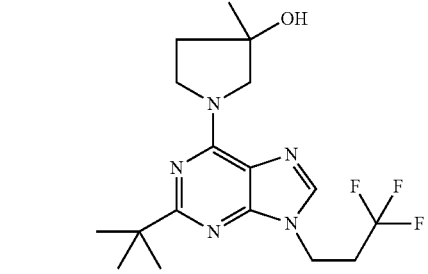 [SMILES: CC1(O)CCN(c2nc(C(C)(C)C)nc3c2ncn3CCC(F)(F)F)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from Acetic acid 1-(2-tert-butyl-9H-purin-6-yl)-3-methyl-pyrrolidin-3-yl ester (example 64, step a) and 1, 1, 1-trifluoro-3-iodo-propane plus subsequent treatment of the crude mixture/residue with K$_2$CO$_3$ in MeOH to cleave the ester moiety. MS(m/e): 372.2 (M+H).

Example 103

N-[(3S)-1-[2-tert-butyl-9-(3,3,3-trifluoropropyl)purin-6-yl]pyrrolidin-3-yl]acetamide

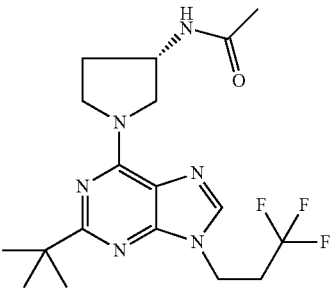 [SMILES: CC(=O)N[C@H]1CCN(c2nc(C(C)(C)C)nc3c2ncn3CCC(F)(F)F)C1]

In analogy to the procedure described for the synthesis of 2-tert-butyl-9-[(4-chlorophenyl)methyl]-6-(3,3-difluoropyrrolidin-1-yl)purine (example 1) the title compound was prepared from N—[(S)-1-(2-tert-Butyl-9H-purin-6-yl)-pyrrolidin-3-yl]-acetamide (example 48, step a) and 1,1,1-trifluoro-3-iodo-propane. MS(m/e): 399.0 (M+H).

Example 104

7-[2-tert-butyl-9-[(3-chloropyridin-2-yl)methyl]purin-6-yl]-2-oxa-7-azaspiro[3.4]octane

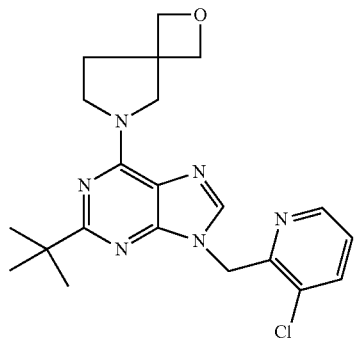 [SMILES: CC(C)(C)c1nc(N2CCC3(COC3)C2)c2ncn(Cc3ncccc3Cl)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from a) 2-tert-Butyl-6-(2-oxa-6-aza-spiro[3.4]oct-6-yl)-9H-purine (example 56, step a) and 3-chloro-2-chloromethyl-pyridine. MS(m/e): 413.0 (M+H).

Example 105

2-tert-butyl-6-(3,3,4,4-tetrafluoropyrrolidin-1-yl)-9-[[2-(trifluoromethyl)phenyl]methyl]purine

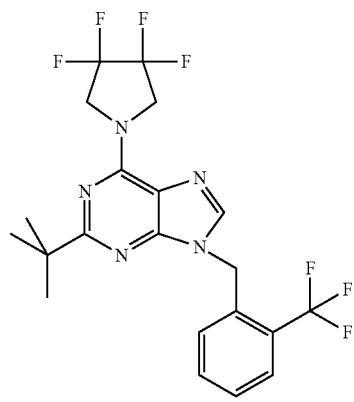 [SMILES: CC(C)(C)c1nc(N2CC(F)(F)C(F)(F)C2)c2ncn(Cc3ccccc3C(F)(F)F)c2n1]

In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3,4,4-tetrafluoro-pyrrolidin-1-yl)-9H-purine (example 72, step a) and 1-bromomethyl-2-trifluoromethyl-benzene. MS(m/e): 476.0 (M+H).

Example 106

2-tert-butyl-9-[(2-methylsulfonylphenyl)methyl]-6-(3,3,4,4-tetrafluoropyrrolidin-1-yl)purine In analogy to the procedure described for the synthesis of 2-tert-butyl-9-[(4-chlorophenyl)methyl]-6-(3,3-difluoropyrrolidin-1-yl)purine (example 1) the title compound was prepared from 2-tert-Butyl-6-(3,3,4,4-tetrafluoro-pyrrolidin-1-yl)-9H-purine (example 72, step a) and 1-bromomethyl-2-methanesulfonyl-benzene. MS(m/e): 485.8 (M+H).

Example 107

N-tert-butyl-9-[(2-chlorophenyl)methyl]-6-(3,3-difluoropyrrolidin-1-yl)purin-2-amine

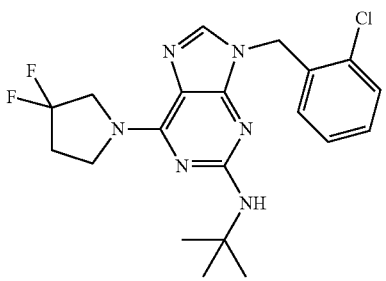 [SMILES: CC(C)(C)Nc1nc(N2CCC(F)(F)C2)c2ncn(Cc3ccccc3Cl)c2n1]

a) 6-(3,3-Difluoro-pyrrolidin-1-yl)-2-fluoro-9H-purine

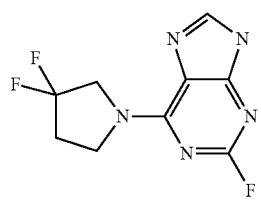 [SMILES: Fc1nc(N2CCC(F)(F)C2)c2nc[nH]c2n1]

To a solution of 6-chloro-2-fluoro-9H-purine (500 mg 2.89 mmol) in tBuOH (10 mL) was added DIPEA (0.68 mL, 3.76 mmol) followed by 3, 3-difluoro-pyrrolidine hydrochloride (415.5 mg 2.89 mmol) and the reaction mixture was heated in a sealed tube at 80° C. for 22 h. The solvent was removed under reduced pressure and the residue was purified by Combi-Flash column chromatography (40 g, hexane/EtOAc 1/6) to yield the title compound (500 mg; 71%) as brown solid MS(m/e): 244.2 (M+H).

b) tert-Butyl-[6-(3,3-difluoro-pyrrolidin-1-yl)-9H-purin-2-yl]-amine

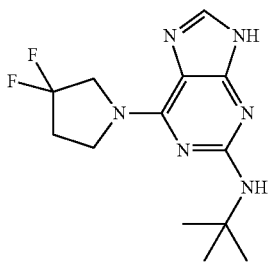 [SMILES: CC(C)(C)Nc1nc(N2CCC(F)(F)C2)c2nc[nH]c2n1]

In a sealed tube a solution of 6-(3,3-difluoro-pyrrolidin-1-yl)-2-fluoro-9H-purine (500 mg, 2.058 mmol) in t-BuOH (10 mL) and tert-butyl amine (1.5 g, 20.57 mmol) was heated at 160° C. for 24 h. The reaction mixture was cooled to 25° C. and solvent was evaporated under reduced pressure. The residue was purified by Combi-Flash column chromatography (40 g, hexane/EtOAc 1/7) to yield the title compound (214 mg; 35%) as a white solid. MS(m/e): 297.2 (M+H).

c) N-tert-butyl-9-[(2-chlorophenyl)methyl]-6-(3,3-difluoropyrrolidin-1-yl)purin-2-amine To a stirred solution of 2-tert-butyl-4-(2-oxa-6-aza-spiro[3.3]hept-6-yl)-7H-pyrrolo[2,3-d]pyrimidine (30 mg, 0.11 mmol) in DMF (5 mL) was added NaH (10 mg, 0.132 mmol) at 0° C. and stirred at 25° C. for 1 h. To this 1-bromomethyl-2-chloro-benzene (30 mg, 0.143 mmol) was added in one portion and the mixture was stirred at 25° C. for 12 h. The reaction mixture was quenched with NH$_4$Cl, the solvent was removed under reduced pressure, the residue was dissolved in H$_2$O (10 mL), extracted with EtOAc washed with brine and concentrated in vacuo. The residue was purified by preparative HPLC to yield the title compound (25 mg, 59%) as off white solid. MS(m/e): 421 (M+H).

Example 108

N-tert-butyl-6-(3,3-difluoropyrrolidin-1-yl)-9-[[2-(trifluoromethyl)phenyl]methyl]purin-2-amine

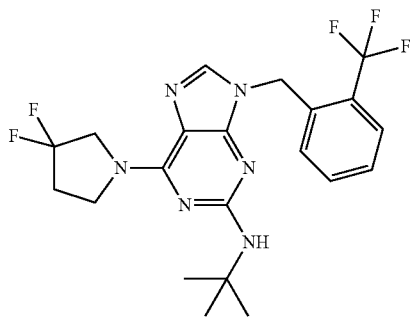 [SMILES: CC(C)(C)Nc1nc(N2CCC(F)(F)C2)c2ncn(Cc3ccccc3C(F)(F)F)c2n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(3,3-difluoro-pyrrolidin-1-yl)-9H-purin-2-yl]-amine (example 107, step b). MS(m/e): 455 (M+H).

Example 109

N-tert-butyl-6-(3,3-difluoropyrrolidin-1-yl)-9-[(5-methyl-1,3,4-oxadiazol-2-yl)methyl]purin-2-amine

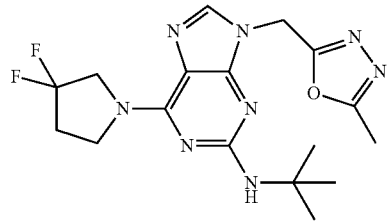 [SMILES: Cc1nnc(Cn2cnc3c(N4CCC(F)(F)C4)nc(NC(C)(C)C)nc32)o1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(3,3-difluoro-pyrrolidin-1-yl)-9H-purin-2-yl]-amine (example 107, step b). MS(m/e): 393 (M+H).

Example 110

N-tert-butyl-6-(3,3-difluoropyrrolidin-1-yl)-9-(3,3,3-trifluoropropyl)purin-2-amine

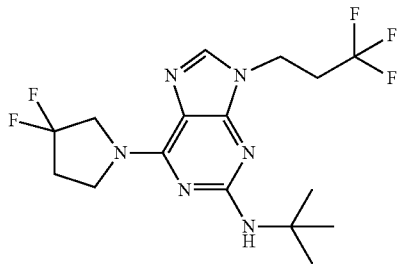 [SMILES: CC(C)(C)Nc1nc(N2CCC(F)(F)C2)c2ncn(CCC(F)(F)F)c2n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(3,3-difluoro-pyrrolidin-1-yl)-9H-purin-2-yl]-amine (example 107, step b). MS(m/e): 393 (M+H).

Example 111

N-tert-butyl-6-(3,3-difluoropyrrolidin-1-yl)-9-[(4-methyl-1,2,5-oxadiazol-3-yl)methyl]purin-2-amine

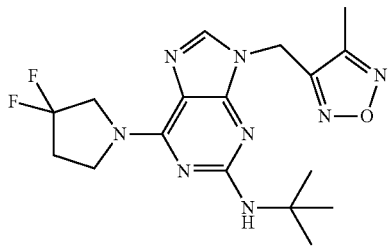 [SMILES: Cc1nonc1Cn1cnc2c(N3CCC(F)(F)C3)nc(NC(C)(C)C)nc21]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(3,3-difluoro-pyrrolidin-1-yl)-9H-purin-2-yl]-amine (example 107, step b). MS(m/e): 393 (M+H).

Example 112

N-tert-butyl-9-[(3-chloropyridin-2-yl)methyl]-6-(3,3-difluoropyrrolidin-1-yl)purin-2-amine

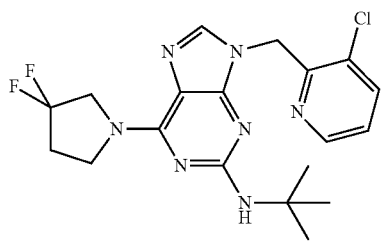 [SMILES: CC(C)(C)Nc1nc(N2CCC(F)(F)C2)c2ncn(Cc3ncccc3Cl)c2n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(3,3-difluoro-pyrrolidin-1-yl)-9H-purin-2-yl]-amine (example 107, step b). MS(m/e): 422 (M+H).

Example 113

N-tert-butyl-6-(3,3-difluoropyrrolidin-1-yl)-9-[(1-methyltetrazol-5-yl)methyl]purin-2-amine

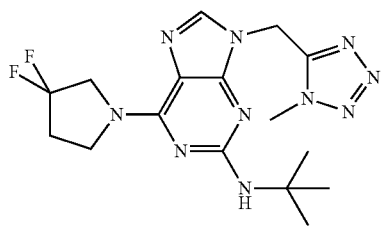 [SMILES: Cn1nnnc1Cn1cnc2c(N3CCC(F)(F)C3)nc(NC(C)(C)C)nc21]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(3,3-difluoro-pyrrolidin-1-yl)-9H-purin-2-yl]-amine (example 107, step b). MS(m/e): 393 (M+H).

Example 114

N-tert-butyl-6-(3,3-difluoropyrrolidin-1-yl)-9-[(2-methylsulfonylphenyl)methyl]purin-2-amine

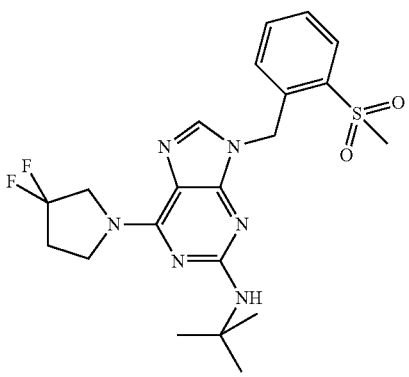 [SMILES: CC(C)(C)Nc1nc(N2CCC(F)(F)C2)c2ncn(Cc3ccccc3S(C)(=O)=O)c2n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(3,3-difluoro-pyrrolidin-1-yl)-9H-purin-2-yl]-amine (example 107, step b). MS(m/e): 465 (M+H).

Example 115

N-tert-butyl-6-(3,3-difluoropyrrolidin-1-yl)-9-[(3-methyl-1,2,4-oxadiazol-5-yl)methyl]purin-2-amine

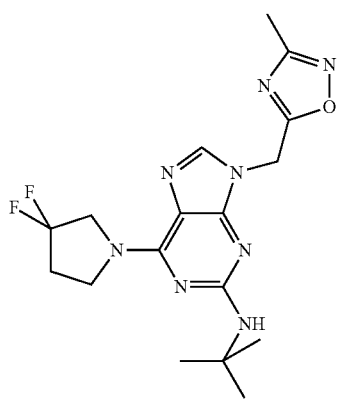 [SMILES: Cc1noc(Cn2cnc3c(N4CCC(F)(F)C4)nc(NC(C)(C)C)nc32)n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(3,3-difluoro-pyrrolidin-1-yl)-9H-purin-2-yl]-amine (example 107, step b). MS(m/e): 393 (M+H).

Example 116

(3S)-1-[2-(tert-butylamino)-9-[(2-chlorophenyl)methyl]purin-6-yl]pyrrolidin-3-ol

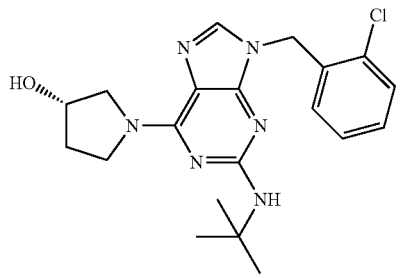 [SMILES: CC(C)(C)Nc1nc(N2CC[C@H](O)C2)c2ncn(Cc3ccccc3Cl)c2n1]

a) Acetic acid (S)-1-(2-fluoro-9H-purin-6-yl)-pyrrolidin-3-yl ester

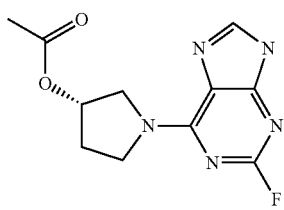 [SMILES: CC(=O)O[C@H]1CCN(c2nc(F)nc3[nH]cnc23)C1]

In analogy to the procedure described for the synthesis of 6-(3,3-Difluoro-pyrrolidin-1-yl)-2-fluoro-9H-purine (example 107, step a) the title compound was prepared from 6-chloro-2-fluoro-9H-purine and Acetic acid (S)-pyrrolidin-3-yl ester. MS(m/e): 266.1 (M+H).

b) Acetic acid (S)-1-(2-tert-butylamino-9H-purin-6-yl)-pyrrolidin-3-yl ester

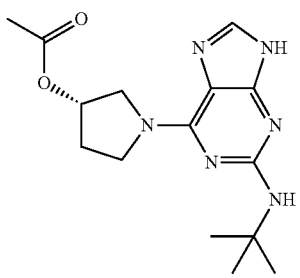 [SMILES: CC(=O)O[C@H]1CCN(c2nc(NC(C)(C)C)nc3[nH]cnc23)C1]

In analogy to the procedure described for the synthesis of tert-Butyl-[6-(3,3-difluoro-pyrrolidin-1-yl)-9H-purin-2-yl]-amine (example 107, step b) the title compound was prepared from Acetic acid (S)-1-(2-fluoro-9H-purin-6-yl)-pyrrolidin-3-yl ester and tert.-butyl-amine. MS(m/e): 318.8 (M+H).

c) (3S)-1-[2-(tert-butylamino)-9-[(2-chlorophenyl)methyl]purin-6-yl]pyrrolidin-3-ol In analogy to the procedure described for the synthesis of N-tert-butyl-9-[(2-chlorophenyl)methyl]-6-(3,3-difluoropyrrolidin-1-yl)purin-2-amine (example 107) the title compound was prepared from acetic acid (S)-1-(2-tert-butylamino-9H-purin-6-yl)-pyrrolidin-3-yl ester (example 108, step b) and 1-bromomethyl-2-chloro-benzene. MS(m/e): 401.3 (M+H).

Example 117

(3S)-1-[2-(tert-butylamino)-9-[[2-(trifluoromethyl)phenyl]methyl]purin-6-yl]pyrrolidin-3-ol

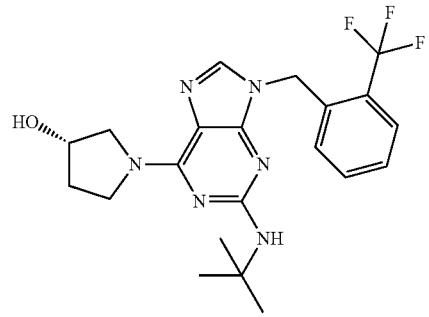 [SMILES: CC(C)(C)Nc1nc(N2CC[C@H](O)C2)c2ncn(Cc3ccccc3C(F)(F)F)c2n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from acetic acid (S)-1-(2-tert-butylamino-9H-purin-6-yl)-pyrrolidin-3-yl ester (example 116, step b). MS(m/e): 435.2 (M+H).

Example 118

(3S)-1-[2-(tert-butylamino)-9-[(3-chloropyridin-2-yl)methyl]purin-6-yl]pyrrolidin-3-ol

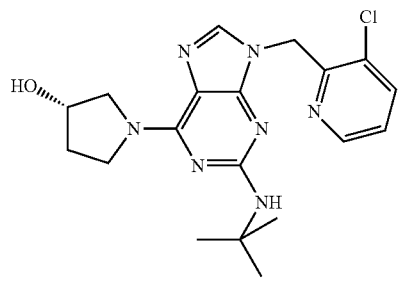 [SMILES: CC(C)(C)Nc1nc(N2CC[C@H](O)C2)c2ncn(Cc3ncccc3Cl)c2n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from acetic acid (S)-1-(2-tert-butylamino-9H-purin-6-yl)-pyrrolidin-3-yl ester (example 116, step b). MS(m/e): 401.8 (M+H).

Example 119

(3S)-1-[2-(tert-butylamino)-9-[(4-methyl-1,2,5-oxadiazol-3-yl)methyl]purin-6-yl]pyrrolidin-3-ol

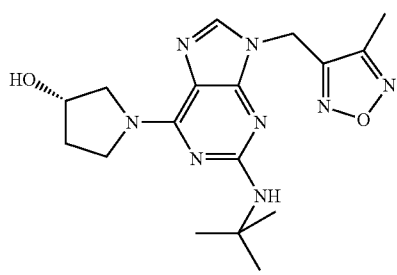 [SMILES: Cc1nonc1Cn1cnc2c(N3CC[C@H](O)C3)nc(NC(C)(C)C)nc21]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from acetic acid (S)-1-(2-tert-butylamino-9H-purin-6-yl)-pyrrolidin-3-yl ester (example 116, step b). MS(m/e): 373.4 (M+H).

Example 120

1-[2-(tert-butylamino)-9-[(2-chlorophenyl)methyl]purin-6-yl]-3-methylpyrrolidin-3-ol

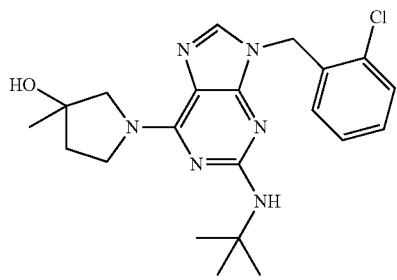 [SMILES: CC1(O)CCN(c2nc(NC(C)(C)C)nc3c2ncn3Cc2ccccc2Cl)C1]

a) Acetic acid 1-(2-fluoro-9H-purin-6-yl)-3-methyl-pyrrolidin-3-yl ester

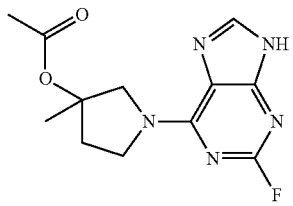 [SMILES: CC(=O)OC1(C)CCN(c2nc(F)nc3[nH]cnc23)C1]

In analogy to the procedure described for the synthesis of 6-(3,3-Difluoro-pyrrolidin-1-yl)-2-fluoro-9H-purine (example 107, step a) the title compound was prepared from 6-chloro-2-fluoro-9H-purine and Acetic acid 3-methyl-pyrrolidin-3-yl ester. MS(m/e): 280.1 (M+H).

b) Acetic acid 1-(2-tert-butylamino-9H-purin-6-yl)-3-methyl-pyrrolidin-3-yl ester

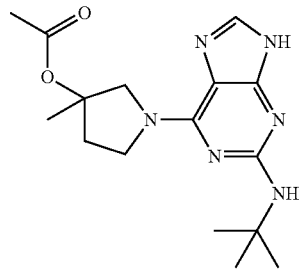 [SMILES: CC(=O)OC1(C)CCN(c2nc(NC(C)(C)C)nc3[nH]cnc23)C1]

In analogy to the procedure described for the synthesis of tert-Butyl-[6-(3,3-difluoro-pyrrolidin-1-yl)-9H-purin-2-yl]-amine (example 107, step b) the title compound was prepared from Acetic acid 1-(2-fluoro-9H-purin-6-yl)-3-methyl-pyrrolidin-3-yl ester and tert.-butyl-amine. MS(m/e): 333.2 (M+H).

c) 1-[2-(tert-butylamino)-9-[(2-chlorophenyl)methyl]purin-6-yl]-3-methylpyrrolidin-3-ol In analogy to the procedure described for the synthesis of N-tert-butyl-9-[(2-chlorophenyl)methyl]-6-(3,3-difluoropyrrolidin-1-yl)purin-2-amine (example 107) the title compound was prepared from acetic acid 1-(2-tert-butylamino-9H-purin-6-yl)-3-methyl-pyrrolidin-3-yl ester (example 120, step b) and 1-bromomethyl-2-chloro-benzene. MS(m/e): 415.2 (M+H).

Example 121

1-[2-(tert-butylamino)-9-[[2-(trifluoromethyl)phenyl]methyl]purin-6-yl]-3-methylpyrrolidin-3-ol

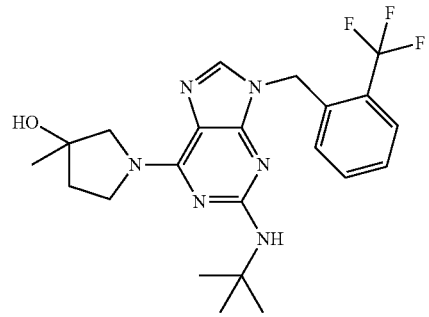 [SMILES: CC1(O)CCN(c2nc(NC(C)(C)C)nc3c2ncn3Cc2ccccc2C(F)(F)F)C1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from Acetic acid 1-(2-tert-butylamino-9H-purin-6-yl)-3-methyl-pyrrolidin-3-yl ester (example 120, step b). MS(m/e): 449.2 (M+H).

Example 122

(3S)-1-[2-(tert-butylamino)-9-[[3-(trifluoromethyl)-1H-pyrazol-4-yl]methyl]purin-6-yl]pyrrolidin-3-ol

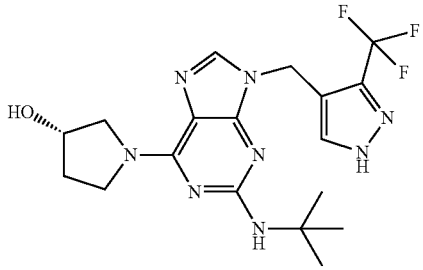 [SMILES: CC(C)(C)Nc1nc(N2CC[C@H](O)C2)c2ncn(Cc3c[nH]nc3C(F)(F)F)c2n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from acetic acid (S)-1-(2-tert-butylamino-9H-purin-6-yl)-pyrrolidin-3-yl ester (example 116, step b) plus deprotection of the trityl group with TFA. MS(m/e): 425 (M+H).

Example 123

1-[2-(tert-butylamino)-9-[(4-methyl-1,2,5-oxadiazol-3-yl)methyl]purin-6-yl]-3-methylpyrrolidin-3-ol

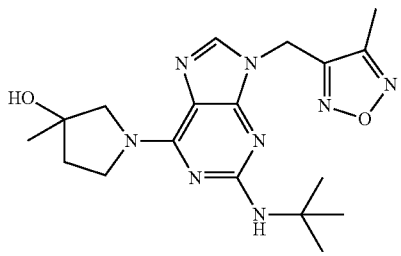 [SMILES: Cc1nonc1Cn1cnc2c(N3CCC(C)(O)C3)nc(NC(C)(C)C)nc21]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from Acetic acid 1-(2-tert-butylamino-9H-purin-6-yl)-3-methyl-pyrrolidin-3-yl ester (example 120, step b). MS(m/e): 387.3 (M+H).

Example 124

9-[(2-chlorophenyl)methyl]-6-(3,3-difluoropyrrolidin-1-yl)-2-(2,2-dimethylpropoxy) purine

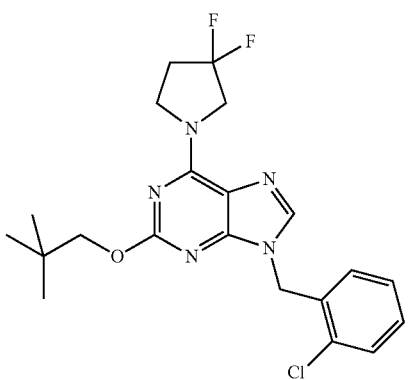 [SMILES: CC(C)(C)COc1nc(N2CCC(F)(F)C2)c2ncn(Cc3ccccc3Cl)c2n1]

a) 6-(3,3-Difluoro-pyrrolidin-1-yl)-2-(2,2-dimethylpropoxy)-9H-purine

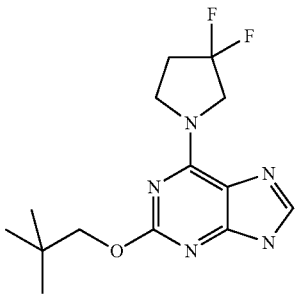 [SMILES: CC(C)(C)COc1nc(N2CCC(F)(F)C2)c2nc[nH]c2n1]

To a solution of 2-chloro-6-(3,3-difluoro-pyrrolidin-1-yl)-9H-purine (1 g, 4.12 mmol) in EtOAc (5 mL) were added dihydropyran (0.75 ml, 8.23 mmol) and pTSA (39 mg; 0.21 mmol) at 25° C. and the reaction mixture was heated at 50° C. for 5 h. The reaction mixture was diluted with EtOAc at 25° C., washed with water, washed with saturated NaHCO₃, washed with brine, dried over anhydrous Na₂SO₄ and evaporated under reduced pressure. The residue was purified by Combi-Flash column chromatography (40 g; hexane/EtOAc 20/80) to yield 2-chloro-6-(3,3-difluoro-pyrrolidin-1-yl)-9-(tetrahydro-pyran-2-yl)-9H-purine (1.0 g; 74%) as white solid. LC-MS: 344 (M+H).

A mixture of 2,2-dimethyl-propan-1-ol (1.9 g, 21.81 mmol) and NaH (60% in oil; 116 mg 2.90 mmol) was heated at 50° C. and 2-chloro-6-(3,3-difluoro-pyrrolidin-1-yl)-9-(tetrahydro-pyran-2-yl)-9H-purine (500 mg 1.45 mmol) was added. The reaction mixture was heated at 80° C. for 12 h. The mixture was quenched with water, extracted with DCM, washed with brine, dried over anhydrous Na₂SO₄ and evaporated under reduced pressure. The residue was purified by Combi-Flash column chromatography (40 g; hexane/EtOAc 30/70) to yield 6-(3,3-difluoro-pyrrolidin-1-yl)-2-(2,2-dimethyl-propoxy)-9-(tetrahydro-pyran-2-yl)-9H-purine (250 mg; 35%) as off white solid. LC-MS: 396 (M+H).

To a solution of 6-(3,3-difluoro-pyrrolidin-1-yl)-2-(2,2-dimethyl-propoxy)-9-(tetrahydro-pyran-2-yl)-9H-purine (500 mg, 1.26 mmol) in EtOH (5 mL) was added pTSA (12 mg; 0.064 mmol) and the reaction mixture was heated at 80° C. for 4 h. The mixture was evaporated at 25° C. The residue was dissolved in EtOAc, washed with water, saturated NaHCO₃, brine, dried over anhydrous Na₂SO₄ and evaporated under reduced pressure. The residue was purified by Combi-Flash column chromatography (40 g; hexane/EtOAc 20/80) to yield the title compound (350 mg; 89%) as white solid. LC-MS: 312 (M+H).

b) 9-[(2-chlorophenyl)methyl]-6-(3,3-difluoropyrrolidin-1-yl)-2-(2,2-dimethylpropoxy)purine In analogy to the procedure described for the synthesis of N-tert-butyl-9-[(2-chlorophenyl)methyl]-6-(3,3-difluoropyrrolidin-1-yl)purin-2-amine (example 107) the title compound was prepared from 6-(3,3-Difluoro-pyrrolidin-1-yl)-2-(2,2-dimethyl-propoxy)-9H-purine (example 124, step a) and 1-bromomethyl-2-chloro-benzene. MS(m/e): 436 (M+H).

Example 125

6-(3,3-difluoropyrrolidin-1-yl)-2-(2,2-dimethyl-propoxy)-9-[[2-(trifluoromethyl)phenyl]methyl]purine

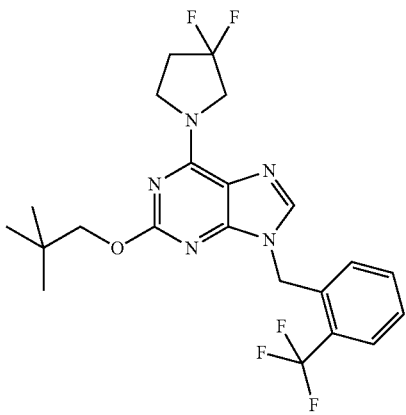 [SMILES: CC(C)(C)COc1nc(N2CCC(F)(F)C2)c2ncn(Cc3ccccc3C(F)(F)F)c2n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from 6-(3,3-Difluoro-pyrrolidin-1-yl)-2-(2,2-dimethyl-propoxy)-9H-purine (example 124, step a). MS(m/e): 470 (M+H).

Example 126

6-(3,3-difluoropyrrolidin-1-yl)-2-(2,2-dimethyl-propoxy)-9-[(2-methylsulfonylphenyl)methyl]purine

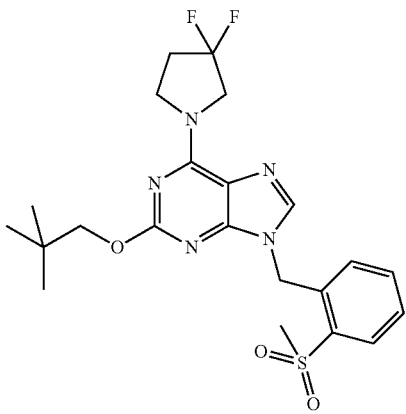 [SMILES: CC(C)(C)COc1nc(N2CCC(F)(F)C2)c2ncn(Cc3ccccc3S(C)(=O)=O)c2n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from 6-(3,3-Difluoro-pyrrolidin-1-yl)-2-(2,2-dimethyl-propoxy)-9H-purine (example 124, step a). MS(m/e): 479.8 (M+H).

Example 127

2-[[6-(3,3-difluoropyrrolidin-1-yl)-2-(2,2-dimethyl-propoxy)purin-9-yl]methyl]-5-methyl-1,3,4-oxadiazole

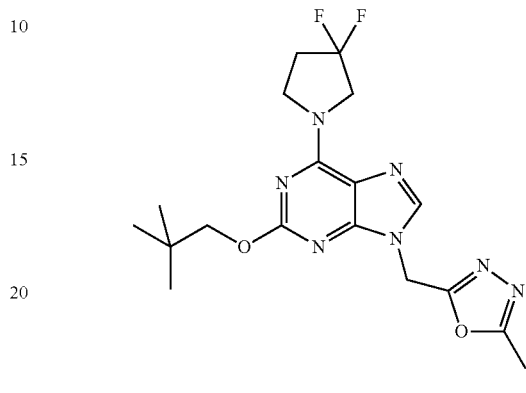

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from 6-(3,3-Difluoro-pyrrolidin-1-yl)-2-(2,2-dimethyl-propoxy)-9H-purine (example 124, step a). MS(m/e): 408 (M+H).

Example 128

5-[[6-(3,3-difluoropyrrolidin-1-yl)-2-(2,2-dimethyl-propoxy)purin-9-yl]methyl]-3-methyl-1,2,4-oxadiazole

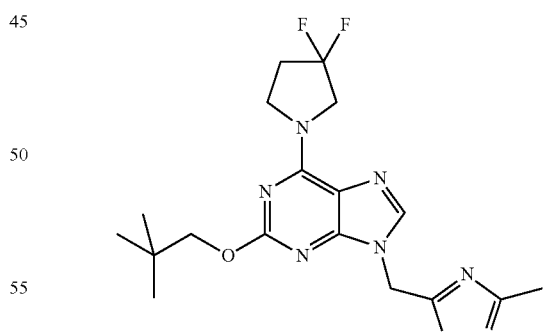

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from 6-(3,3-Difluoro-pyrrolidin-1-yl)-2-(2,2-dimethyl-propoxy)-9H-purine (example 124, step a). MS(m/e): 408 (M+H).

Example 129

6-(3,3-difluoropyrrolidin-1-yl)-2-(2,2-dimethyl-propoxy)-9-[(1-methyltetrazol-5-yl)methyl]purine

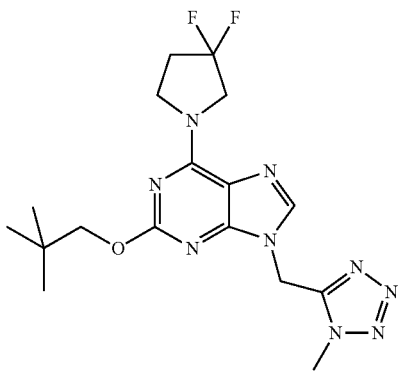 [SMILES: Cn1nnnc1Cn1cnc2c(N3CCC(F)(F)C3)nc(OCC(C)(C)C)nc21]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from 6-(3,3-Difluoro-pyrrolidin-1-yl)-2-(2,2-dimethyl-propoxy)-9H-purine (example 124, step a). MS(m/e): 408 (M+H).

Example 130

(3S)-1-[2-(tert-butylamino)-9-(3,3,3-trifluoropropyl)purin-6-yl]pyrrolidin-3-ol

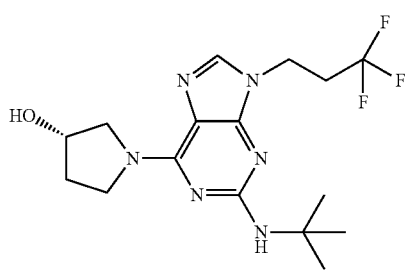 [SMILES: CC(C)(C)Nc1nc(N2CC[C@H](O)C2)c2ncn(CCC(F)(F)F)c2n1]

a) Acetic acid (S)-1-(2-fluoro-9H-purin-6-yl)-pyrrolidin-3-yl ester

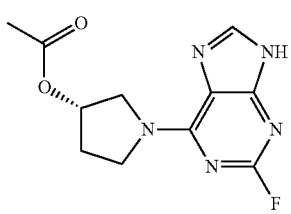 [SMILES: CC(=O)O[C@H]1CCN(c2nc(F)nc3[nH]cnc23)C1]

In analogy to the procedure described for the synthesis of 6-(3,3-Difluoro-pyrrolidin-1-yl)-2-fluoro-9H-purine (example 107, step a) the title compound was prepared from 6-chloro-2-fluoro-9H-purine and Acetic acid (S)-pyrrolidin-3-yl ester. MS(m/e): 266.1 (M+H).

b) Acetic acid (S)-1-(2-tert-butylamino-9H-purin-6-yl)-pyrrolidin-3-yl ester

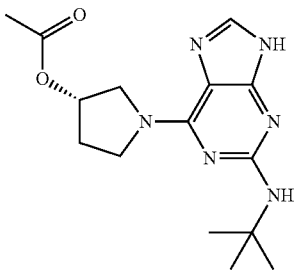

In analogy to the procedure described for the synthesis of tert-Butyl-[6-(3,3-difluoro-pyrrolidin-1-yl)-9H-purin-2-yl]-amine (example 107, step b) the title compound was prepared from Acetic acid (S)-1-(2-fluoro-9H-purin-6-yl)-pyrrolidin-3-yl ester and tert-butyl-amine. MS(m/e): 277 (M+H).

c) (3S)-1-[2-(tert-butylamino)-9-(3,3,3-trifluoropropyl)purin-6-yl]pyrrolidin-3-ol In analogy to the procedure described for the synthesis of N-tert-butyl-9-[(2-chlorophenyl)methyl]-6-(3,3-difluoropyrrolidin-1-yl)purin-2-amine (example 107) the title compound was prepared from Acetic acid (S)-1-(2-tert-butylamino-9H-purin-6-yl)-pyrrolidin-3-yl ester (example 130, step b). MS(m/e): 373.3 (M+H).

Example 131

1-[9-[(2-chlorophenyl)methyl]-2-(2,2-dimethyl-propoxy)purin-6-yl]-3-methyl pyrrolidin-3-ol

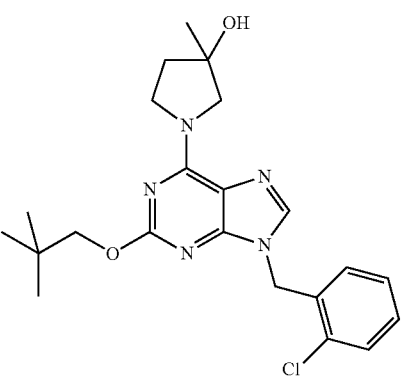 [SMILES: CC(C)(C)COc1nc(N2CCC(C)(O)C2)c2ncn(Cc3ccccc3Cl)c2n1]

In analogy to the procedure described for the synthesis of 9-[(2-chlorophenyl)methyl]-6-(3,3-difluoropyrrolidin-1-yl)-2-(2,2-dimethylpropoxy)purine (example 124) the intermediate 1-[2-(2,2-Dimethyl-propoxy)-9H-purin-6-yl]-3-methyl-pyrrolidin-3-ol was prepared from acetic acid 1-(2-fluoro-9H-purin-6-yl)-3-methyl-pyrrolidin-3-yl ester by protection of N1 with THP and subsequent nucleophilic substitution at C7 with 2,2-dimethyl-propan-1-ol and finally deprotection at N1 with p-TSA. LC-MS: 306.4 (M+H).

The free alcohol moiety was protected with TBDMS by reaction of 1-[2-(2,2-dimethyl-propoxy)-9H-purin-6-yl]-3-methyl-pyrrolidin-3-ol with tert-butyldimethylsilyl chloride and imidazole in DMF.

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from TBDMS protected 1-[2-(2,2-Dimethyl-propoxy)-9H-purin-6-yl]-3-methyl-pyrrolidin-3-ol and 1-bromomethyl-2-chloro-benzene. Deprotection of the silyl protecting group with TBAF yielded the title compound. MS(m/e): 430 (M+H).

Example 132

1-[2-(2,2-dimethylpropoxy)-9-[[2-(trifluoromethyl)phenyl]methyl]purin-6-yl]-3-methylpyrrolidin-3-ol

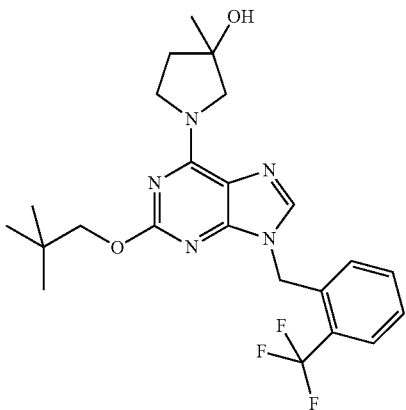 [SMILES: CC(C)(C)COc1nc(N2CCC(C)(O)C2)c2ncn(Cc3ccccc3C(F)(F)F)c2n1]

In analogy to the procedure described for the synthesis of 1-[9-[(2-chlorophenyl)methyl]-2-(2,2-dimethylpropoxy)purin-6-yl]-3-methylpyrrolidin-3-ol (example 131) the title compound was prepared from the TBDMS-protected 1-[2-(2,2-Dimethyl-propoxy)-9H-purin-6-yl]-3-methyl-pyrrolidin-3-ol and 1-Bromomethyl-2-trifluoromethyl-benzene plus cleavage of the TBDMS group with TBAF. MS(m/e): 463.8 (M+H).

Example 133

1-[2-(2,2-dimethylpropoxy)-9-[(2-methylsulfonylphenyl)methyl]purin-6-yl]-3-methylpyrrolidin-3-ol

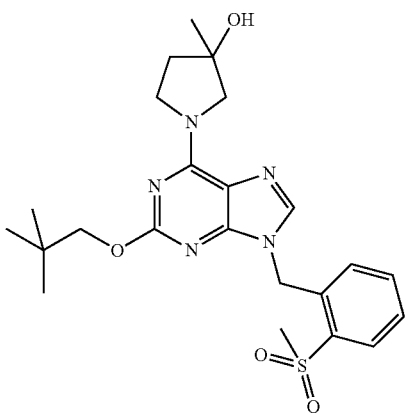 [SMILES: CC(C)(C)COc1nc(N2CCC(C)(O)C2)c2ncn(Cc3ccccc3S(C)(=O)=O)c2n1]

In analogy to the procedure described for the synthesis of 1-[9-[(2-chlorophenyl)methyl]-2-(2,2-dimethylpropoxy)purin-6-yl]-3-methylpyrrolidin-3-ol (example 131) the title compound was prepared from the TBDMS-protected 1-[2-(2,2-Dimethyl-propoxy)-9H-purin-6-yl]-3-methyl-pyrrolidin-3-ol and 1-Bromomethyl-2-methanesulfonyl-benzene plus cleavage of the TBDMS group with TBAF. MS(m/e): 474.0 (M+H).

Example 134

1-[9-[(3-chloropyridin-2-yl)methyl]-2-(2,2-dimethylpropoxy)purin-6-yl]-3-methylpyrrolidin-3-ol

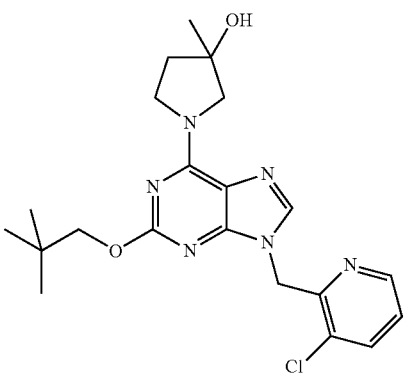 [SMILES: CC(C)(C)COc1nc(N2CCC(C)(O)C2)c2ncn(Cc3ncccc3Cl)c2n1]

In analogy to the procedure described for the synthesis of 1-[9-[(2-chlorophenyl)methyl]-2-(2,2-dimethylpropoxy)purin-6-yl]-3-methylpyrrolidin-3-ol (example 131) the title compound was prepared from the TBDMS-protected 1-[2-(2,2-Dimethyl-propoxy)-9H-purin-6-yl]-3-methyl-pyrrolidin-3-ol and 2-Bromomethyl-3-chloro-pyridine plus cleavage of the TBDMS group with TBAF. MS(m/e): 430.8 (M+H).

Example 135

1-[2-(2,2-dimethylpropoxy)-9-[(4-methyl-1,2,5-oxadiazol-3-yl)methyl]purin-6-yl]-3-methylpyrrolidin-3-ol

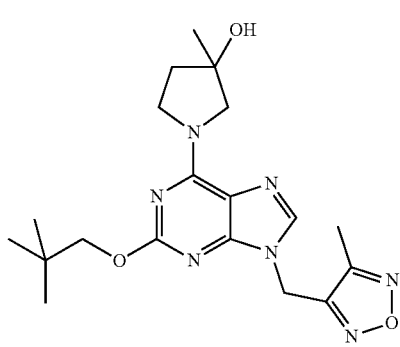 [SMILES: Cc1nonc1Cn1cnc2c(N3CCC(C)(O)C3)nc(OCC(C)(C)C)nc21]

In analogy to the procedure described for the synthesis of 1[9-[2-chlorophenyl)methyl]-2-(2,2-dimethylpropoxy)purin-6-yl]-3-methylpyrrolidin-3-ol (example 131) the title compound was prepared from the TBDMS-protected 1-[2-(2,2-Dimethyl-propoxy)-9H-purin-6-yl]-3-methyl-pyrrolidin-3-ol and 3-Chloromethyl-4-methyl-furazan plus cleavage of the TBDMS group with TBAF. MS(m/e): 401.8 (M+H).

Example 136

1-[2-(tert-butylamino)-9-[[3-(trifluoromethyl)-1H-pyrazol-4-yl]methyl]purin-6-yl]-3-methylpyrrolidin-3-ol

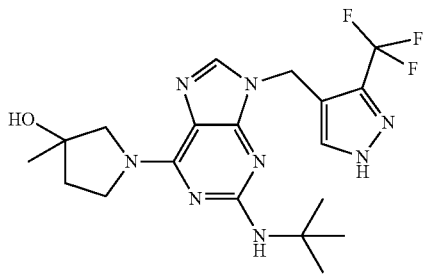 [SMILES: CC1(O)CCN(c2nc(NC(C)(C)C)nc3c2ncn3Cc2c[nH]nc2C(F)(F)F)C1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from Acetic acid 1-(2-tert-butylamino-9H-purin-6-yl)-3-methyl-pyrrolidin-3-yl ester (example 120, step b) plus cleavage of the trityl group with TFA. MS(m/e): 439.3 (M+H).

Example 137

N-tert-butyl-6-(2-oxa-6-azaspiro[3.3]heptan-6-yl)-9-[[2-(trifluoromethyl)phenyl]methyl]purin-2-amine

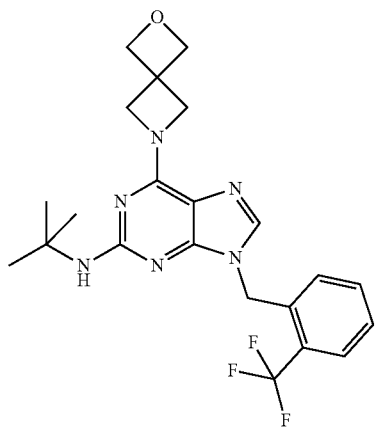 [SMILES: CC(C)(C)Nc1nc(N2CC3(COC3)C2)c2ncn(Cc3ccccc3C(F)(F)F)c2n1]

a) 2-Fluoro-6-(2-oxa-6-aza-spiro[3.3]hept-6-yl)-9-(tetrahydro-pyran-2-yl)-9H-purine

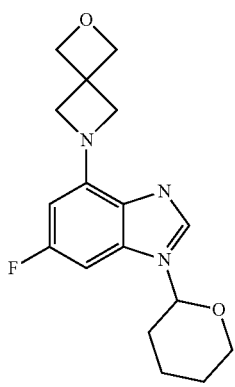

The title compound was prepared from 6-chloro-2-fluoro-9-(tetrahydro-pyran-2-yl)-9H-purine and protection with THP. LC-MS: 320.3 (M+H).

b) tert-Butyl-[6-(2-oxa-6-aza-spiro[3.3]hept-6-yl)-9H-purin-2-yl]-amine

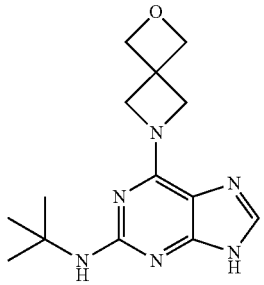 [SMILES: CC(C)(C)Nc1nc(N2CC3(COC3)C2)c2nc[nH]c2n1]

The title compound was prepared from 2-Fluoro-6-(2-oxa-6-aza-spiro[3.3]hept-6-yl)-9-(tetrahydro-pyran-2-yl)-9H-purine through nucleophilic substitution with tert-butylamine and subsequent cleavage of the THP group with PTSA.

c) N-tert-butyl-6-(2-oxa-6-azaspiro[3.3]heptan-6-yl)-9-[[2-(trifluoromethyl)phenyl]methyl]purin-2-amine In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(2-oxa-6-aza-spiro[3.3]hept-6-yl)-9H-purin-2-yl]-amine (example 137, step b). MS(m/e): 446.8 (M+H).

Example 138

N-tert-butyl-9-[(2-chlorophenyl)methyl]-6-(2-oxa-6-azaspiro[3.3]heptan-6-yl)purin-2-amine

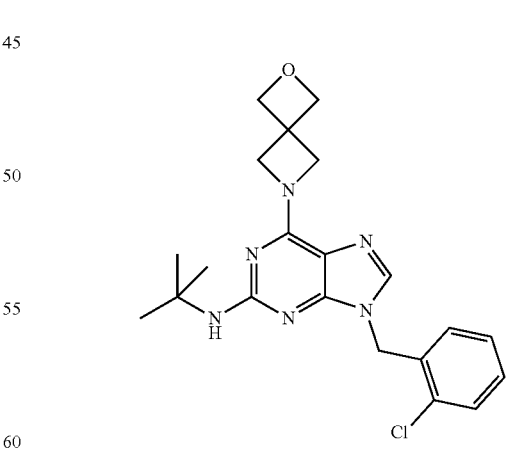

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(2-oxa-6-aza-spiro[3.3]hept-6-yl)-9H-purin-2-yl]-amine (example 137, step b). MS(m/e): 413 (M+H).

Example 139

(3S)-1-[2-tert-butyl-9-[(1-cyclopropyltetrazol-5-yl)methyl]purin-6-yl]pyrrolidin-3-ol

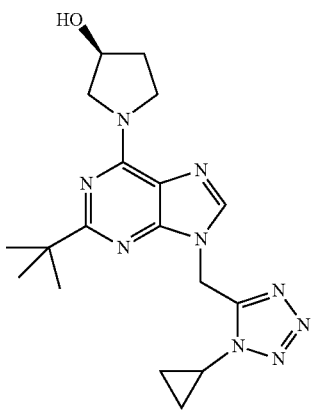 [SMILES: CC(C)(C)c1nc(N2CC[C@H](O)C2)c2ncn(Cc3nnnn3C3CC3)c2n1]

a) 2-tert-Butyl-6-chloro-9-(1-cyclopropyl-1H-tetrazol-5-ylmethyl)-9H-purine

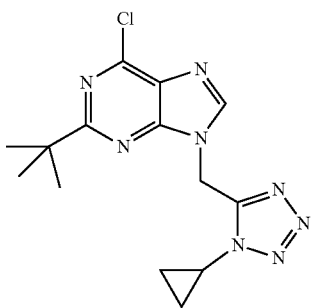 [SMILES: CC(C)(C)c1nc(Cl)c2ncn(Cc3nnnn3C3CC3)c2n1]

A mixture of 2-tert-butyl-6-chloro-9H-purine (200 mg, 949 μmol), NaH 60% (49.4 mg, 1.23 mmol) in DMF (8 mL) was treated with 5-(chloromethyl)-1-cyclopropyl-1H-tetrazole (226 mg, 1.42 mmol) and stirred at 60° C. The mixture was quenched with water (20 mL) and extracted with EtOAc (3×20 mL). The organic layers were combined, dried over Na₂SO₄, filtered and concentrated in vacuo. The residue was purified by HPLC to yield the title compound (203 mg, 64%) as off-white solid.

b) (3S)-1-[2-tert-butyl-9-[(1-cyclopropyltetrazol-5-yl)methyl]purin-6-yl]pyrrolidin-3-ol 2-tert-butyl-6-chloro-9-((1-cyclopropyl-1H-tetrazol-5-yl)methyl)-9H-purine (50 mg, 150 μmmol) in acetonitrile (683 μL) was treated with DIPEA (29.1 mg, 225 μmol) and (S)-pyrrolidin-3-ol (14.4 mg, 165 μmol). The reaction mixture was stirred for 3 h at rt. 1 mL toluene was added to the reaction mixture and the solution concentrated. The residue was transferred to a separating funnel, treated with citric acid 10% and extracted. The aqueous phase was extracted a second time with toluene. The combined organic phases were washed with NaHCO₃ followed by NaCl. The organic extracts were combined and dried over Na₂SO₄. Under stirring heptane was added. After 5 min product started to crystallize and the suspension was stirred overnight. The suspension was filtered, the crystals washed with heptane and dried to yield the title compound (16 mg, 28%) as a white solid. MS(m/e): 384.5 (M+H).

Example 140

3-[[6-(3,3-difluoropyrrolidin-1-yl)-2-(2,2-dimethyl-propoxy)purin-9-yl]methyl]-4-methyl-1,2,5-oxadiazole

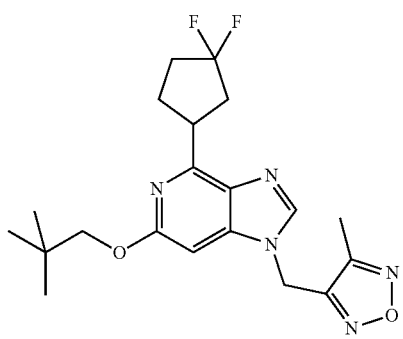 [SMILES: Cc1nonc1Cn1cnc2c(C3CCC(F)(F)C3)nc(OCC(C)(C)C)cc21]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from 6-(3,3-Difluoro-pyrrolidin-1-yl)-2-(2,2-dimethyl-propoxy)-9H-purine (example 124, step a). MS(m/e): 408 (M+H).

Example 141

N-tert-butyl-9-[(3-methyl-1,2,4-oxadiazol-5-yl)methyl]-6-(2-oxa-6-azaspiro[3.3]heptan-6-yl)purin-2-amine

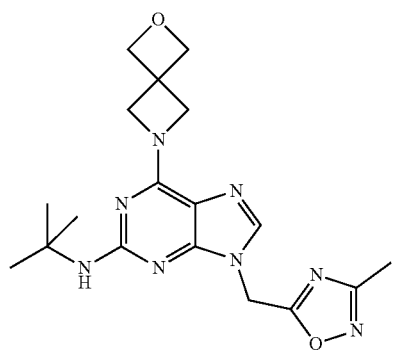 [SMILES: Cc1noc(Cn2cnc3c(N4CC5(COC5)C4)nc(NC(C)(C)C)nc32)n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(2-oxa-6-aza-spiro[3.3]hept-6-yl)-9H-purin-2-yl]-amine (example 137, step b). MS(m/e): 385.3 (M+H).

Example 142

N-tert-butyl-6-(2-oxa-6-azaspiro[3.3]heptan-6-yl)-9-(3,3,3-trifluoropropyl)purin-2-amine

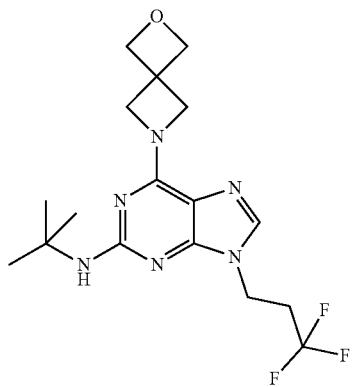 [SMILES: CC(C)(C)Nc1nc(N2CC3(COC3)C2)c2ncn(CCC(F)(F)F)c2n1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from tert-Butyl-[6-(2-oxa-6-aza-spiro[3.3]hept-6-yl)-9H-purin-2-yl]-amine (example 137, step b). MS(m/e): 385.2 (M+H).

Example 143

6-[9-[(2-chlorophenyl)methyl]-2-(2,2-dimethyl-propoxy)purin-6-yl]-2-oxa-6-azaspiro[3.3]heptane

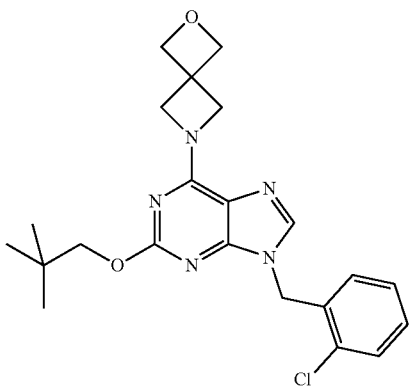 [SMILES: CC(C)(C)COc1nc(N2CC3(COC3)C2)c2ncn(Cc3ccccc3Cl)c2n1]

a) 2-(2,2-Dimethyl-propoxy)-6-(2-oxa-6-aza-spiro[3.3]hept-6-yl)-9H-purine

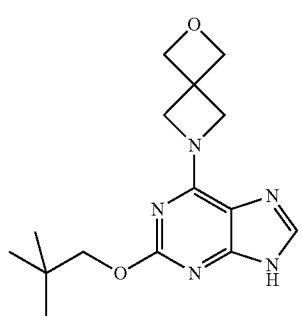 [SMILES: CC(C)(C)COc1nc(N2CC3(COC3)C2)c2nc[nH]c2n1]

2,6-Dichloro-9H-purine was N1 protected with THP in the presence of PTSA. Subsequent nucleophilic substitution first with 2-Oxa-6-aza-spiro[3.3]heptane at C5 and second with 2,2-Dimethyl-propan-1-ol at C7 yielded the intermediate which was deprotected at N1 with PTSA to yield the title compound.

b) 6-[9-[(2-chlorophenyl)methyl]-2-(2,2-dimethyl-propoxy)purin-6-yl]-2-oxa-6-azaspiro[3.3]heptane In analogy to the procedure described for the synthesis of N-tert-butyl-9-[(2-chlorophenyl)methyl]-6-(3,3-difluoropyrrolidin-1-yl)purin-2-amine (example 107) the title compound was prepared from 2-(2,2-Dimethyl-propoxy)-6-(2-oxa-6-aza-spiro[3.3]hept-6-yl)-9H-purine (example 143, step a). MS(m/e): 428 (M+H).

Example 144

3-[[2-tert-butyl-6-(4-methylpiperazin-1-yl)purin-9-yl]methyl]-4-methyl-1,2,5-oxadiazole

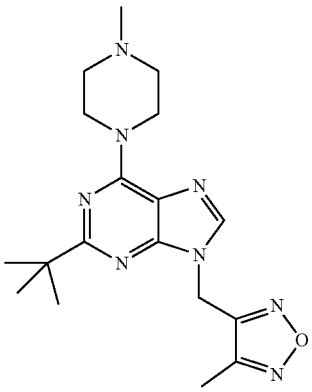 [SMILES: Cc1nonc1Cn1cnc2c(N3CCN(C)CC3)nc(C(C)(C)C)nc21]

In analogy to the procedure described for the synthesis of (3S)-1-[2-tert-butyl-9-[(1-cyclopropyltetrazol-5-yl)methyl]purin-6-yl]pyrrolidin-3-ol (example 139) the title compound was prepared from 2-tert-butyl-6-chloro-9H-purine, 3-(chloromethyl)-4-methyl-1,2,5-oxadiazole and 1-methylpiperazine. MS(m/e): 371.7 (M+H).

Example 145

[(2R)-1-[2-tert-butyl-9-[(4-methyl-1,2,5-oxadiazol-3-yl)methyl]purin-6-yl]pyrrolidin-2-yl]methanol

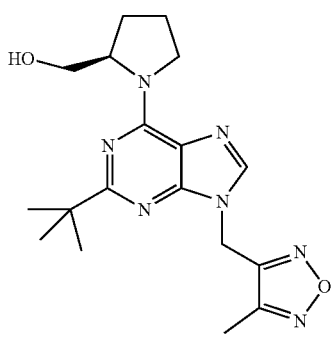 [SMILES: Cc1nonc1Cn1cnc2c(N3CCC[C@@H]3CO)nc(C(C)(C)C)nc21]

In analogy to the procedure described for the synthesis of (3S)-1-[2-tert-butyl-9-[(1-cyclopropyltetrazol-5-yl)methyl]purin-6-yl]pyrrolidin-3-ol (example 139) the title compound was prepared from 2-tert-butyl-6-chloro-9H-purine, 3-(chloromethyl)-4-methyl-1,2,5-oxadiazole and (R)-pyrrolidin-2-ylmethanol. MS(m/e): 372.7 (M+H).

Example 146

[(2R)-1-[2-tert-butyl-9-[(1-cyclopropyltetrazol-5-yl)methyl]purin-6-yl]pyrrolidin-2-yl]methanol

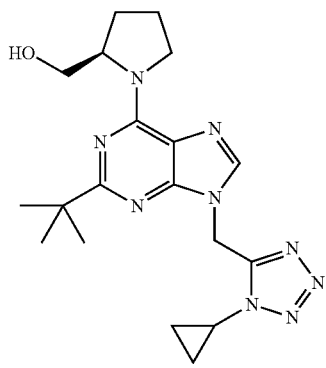 [SMILES: CC(C)(C)c1nc(N2CCC[C@@H]2CO)c2ncn(Cc3nnnn3C3CC3)c2n1]

In analogy to the procedure described for the synthesis of (3S)-1-[2-tert-butyl-9-[(1-cyclopropyltetrazol-5-yl)methyl]purin-6-yl]pyrrolidin-3-ol (example 139) the title compound was prepared from 2-tert-butyl-6-chloro-9H-purine, 5-(chloromethyl)-1-cyclopropyl-1H-tetrazole and (R)-pyrrolidin-2-ylmethanol. MS(m/e): 398.5 (M+H).

Example 147

(2R)-1-[2-tert-butyl-9-[(1-cyclopropyltetrazol-5-yl)methyl]purin-6-yl]pyrrolidine-2-carbonitrile

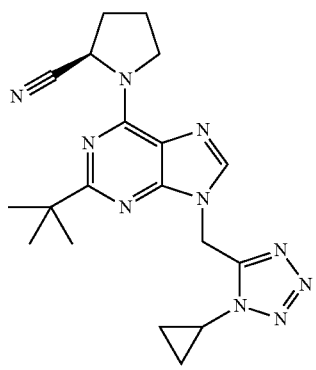 [SMILES: CC(C)(C)c1nc(N2CCC[C@@H]2C#N)c2ncn(Cc3nnnn3C3CC3)c2n1]

In analogy to the procedure described for the synthesis of (3S)-1-[2-tert-butyl-9-[(1-cyclopropyltetrazol-5-yl)methyl]purin-6-yl]pyrrolidin-3-ol (example 139) the title compound was prepared from 2-tert-butyl-6-chloro-9H-purine, 5-(chloromethyl)-1-cyclopropyl-1H-tetrazole and (R)-pyrrolidine-2-carbonitrile hydrochloride. MS(m/e): 393.6 (M+H).

Example 148

(2R)-1-[2-tert-butyl-9-[(4-methyl-1,2,5-oxadiazol-3-yl)methyl]purin-6-yl]pyrrolidine-2-carbonitrile

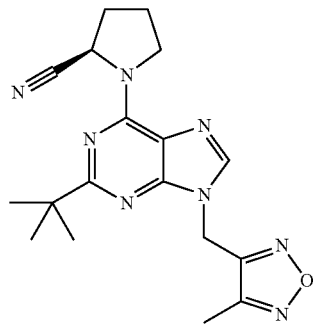 [SMILES: Cc1nonc1Cn1cnc2c(N3CCC[C@@H]3C#N)nc(C(C)(C)C)nc21]

In analogy to the procedure described for the synthesis of (3S)-1-[2-tert-butyl-9-[(1-cyclopropyltetrazol-5-yl)methyl]purin-6-yl]pyrrolidin-3-ol (example 139) the title compound was prepared from 2-tert-butyl-6-chloro-9H-purine, 3-(chloromethyl)-4-methyl-1,2,5-oxadiazole and (R)-pyrrolidine-2-carbonitrile hydrochloride. MS(m/e): 367.5 (M+H).

Example 149

6-[2-tert-butyl-9-[(4-methyl-1,2,5-oxadiazol-3-yl)methyl]purin-6-yl]-2-oxa-6-azaspiro[3.3]heptane

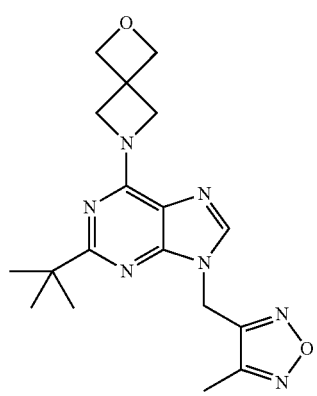 [SMILES: Cc1nonc1Cn1cnc2c(N3CC4(COC4)C3)nc(C(C)(C)C)nc21]

In analogy to the procedure described for the synthesis of (3S)-1-[2-tert-butyl-9-[(1-cyclopropyltetrazol-5-yl)methyl]purin-6-yl]pyrrolidin-3-ol (example 139) the title compound was prepared from 2-tert-butyl-6-chloro-9H-purine, 3-(chloromethyl)-4-methyl-1,2,5-oxadiazole and 2-oxa-6-azaspiro[3.3]heptane oxalate. MS(m/e): 370.5 (M+H).

Example 150

3-[[2-tert-butyl-6-(1,3-thiazolidin-3-yl)purin-9-yl]methyl]-4-methyl-1,2,5-oxadiazole

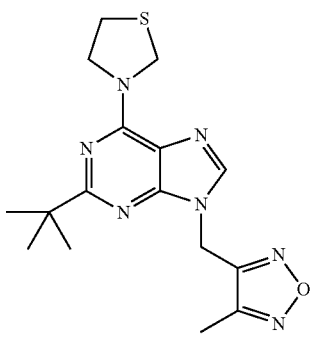 [SMILES: Cc1nonc1Cn1cnc2c(N3CCSC3)nc(C(C)(C)C)nc21]

In analogy to the procedure described for the synthesis of (3S)-1-[2-tert-butyl-9-[(1-cyclopropyltetrazol-5-yl)methyl]purin-6-yl]pyrrolidin-3-ol (example 139) the title compound was prepared from 2-tert-butyl-6-chloro-9H-purine, 3-(chloromethyl)-4-methyl-1,2,5-oxadiazole and thiazolidine. MS(m/e): 360.5 (M+H).

Example 151

6-(3,3-difluoropyrrolidin-1-yl)-2-(2,2-dimethyl-propoxy)-9H-purine

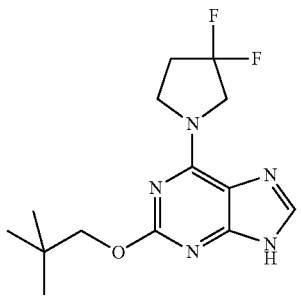 [SMILES: CC(C)(C)COc1nc(N2CCC(F)(F)C2)c2nc[nH]c2n1]

To a solution of 2-chloro-6-(3,3-difluoro-pyrrolidin-1-yl)-9H-purine (1 g, 4.12 mmol) in EtOAc (5 mL) were added dihydropyran (0.75 ml, 8.23 mmol) and pTSA (39 mg; 0.21 mmol) at 25° C. and the reaction mixture was heated at 50° C. for 5 h. The reaction mixture was diluted with EtOAc at 25° C., washed with water, washed with saturated NaHCO₃, washed with brine, dried over anhydrous Na₂SO₄ and evaporated under reduced pressure. The residue was purified by Combi-Flash column chromatography (40 g; hexane/EtOAc 20/80) to yield 2-chloro-6-(3,3-difluoro-pyrrolidin-1-yl)-9-(tetrahydro-pyran-2-yl)-9H-purine (1.0 g; 74%) as white solid. LC-MS: 344 (M+H).

A mixture of 2,2-dimethyl-propan-1-ol (1.9 g, 21.81 mmol) and NaH (60% in oil; 116 mg 2.90 mmol) was heated at 50° C. and 2-chloro-6-(3,3-difluoro-pyrrolidin-1-yl)-9-(tetrahydro-pyran-2-yl)-9H-purine (500 mg 1.45 mmol) was added. The reaction mixture was heated at 80° C. for 12 h. The mixture was quenched with water, extracted with DCM, washed with brine, dried over anhydrous Na₂SO₄ and evaporated under reduced pressure. The residue was purified by Combi-Flash column chromatography (40 g; hexane/EtOAc 30/70) to yield 6-(3,3-difluoro-pyrrolidin-1-yl)-2-(2,2-dimethyl-propoxy)-9-(tetrahydro-pyran-2-yl)-9H-purine (250 mg; 35%) as off white solid. LC-MS: 396 (M+H).

To a solution of 6-(3,3-difluoro-pyrrolidin-1-yl)-2-(2,2-dimethyl-propoxy)-9-(tetrahydro-pyran-2-yl)-9H-purine (500 mg, 1.26 mmol) in EtOH (5 mL) was added pTSA (12 mg; 0.064 mmol) and the reaction mixture was heated at 80° C. for 4 h. The mixture was evaporated at 25° C. The residue was dissolved in EtOAc, washed with water, saturated NaHCO₃, brine, dried over anhydrous Na₂SO₄ and evaporated under reduced pressure. The residue was purified by Combi-Flash column chromatography (40 g; hexane/EtOAc 20/80) to yield the title compound (350 mg; 89%) as white solid. LC-MS: 312 (M+H).

Example 152

[(3S)-1-[2-(tert-butylamino)-9-[(4-methyl-1,2,5-oxadiazol-3-yl)methyl]purin-6-yl]pyrrolidin-3-yl] acetate

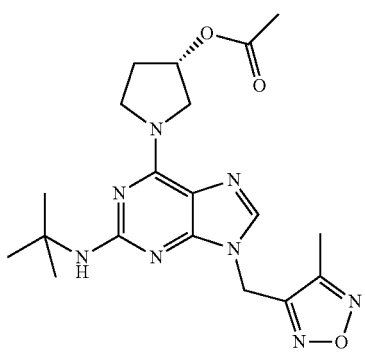 [SMILES: CC(=O)O[C@H]1CCN(c2nc(NC(C)(C)C)nc3c2ncn3Cc2nonc2C)C1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from acetic acid (S)-1-(2-tert-butylamino-9H-purin-6-yl)-pyrrolidin-3-yl ester (example 108, step b) and 3-chloromethyl-4-methyl-furazan. MS(m/e): 415 (M+H).

Example 153

[1-[2-(tert-butylamino)-9-[(4-methyl-1,2,5-oxadiazol-3-yl)methyl]purin-6-yl]-3-methylpyrrolidin-3-yl]acetate

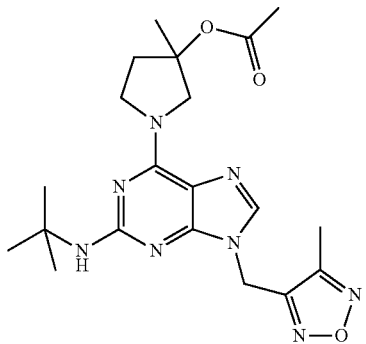 [SMILES: CC(=O)OC1(C)CCN(c2nc(NC(C)(C)C)nc3c2ncn3Cc2nonc2C)C1]

In analogy to the procedure described for the synthesis of N-tert-butyl-9-[(2-chlorophenyl)methyl]-6-(3,3-difluoropyrrolidin-1-yl)purin-2-amine (example 107) the title compound was prepared from Acetic acid 1-(2-tert-butylamino-9H-purin-6-yl)-3-methyl-pyrrolidin-3-yl ester (example 120, step b) and 3-chloromethyl-4-methyl-furazan. MS(m/e): 428.8 (M+H).

Example 154

9-benzyl-2-chloro-6-(3,3-difluoropyrrolidin-1-yl)purine

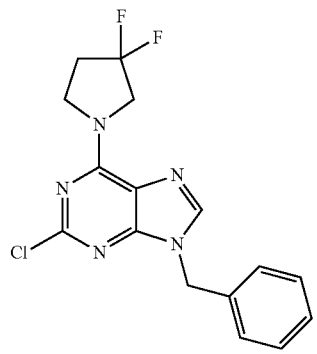 [SMILES: FC1(F)CCN(c2nc(Cl)nc3c2ncn3Cc2ccccc2)C1]

To a solution of 2,6-dichloro-9H-purine (commercially available) (1 g; 5.29 mmol) in DMF (10 mL) was added Et$_3$N (0.8 mL; 5.82 mmol) followed by (3,3-difluoropyrrolidine hydrochloride (0.8 g; 5.56 mmol) at 25° C. and the reaction mixture was heated at 80° C. for 12 h. The reaction mixture was quenched with ice-cold water and stirred it for 30 min at 0° C. The solid was filtered; washed with cold water, and finally dried under high vacuum at 50° C. to give 2-chloro-6-(3,3-difluoropyrrolidin-1-yl)-9H-purine (1 g; 73%) as light yellow solid; which was directly used for next step without further purification. LC-MS: 260.2 (M+H). To a solution of crude 2-chloro-6-(3,3-difluoro-pyrrolidin-1-yl)-9H-purine (200 mg, 0.7 mmol) in DMF (10 mL) was added NaH (70 mg, 1.7 mmol) at 0° C. and stirred the reaction mixture at 25° C. for 1 h. To this benzyl bromide (160 mg, 0.92 mmol) was added in one portion, and the mixture was stirred at 25° C. for 12 h. The reaction mixture was quenched with NH$_4$Cl, the solvent was removed under reduced pressure, and the residue was dissolved in H$_2$O (10 mL), extracted with EtOAc; washed with brine, concentrated in vacuo. The crude was purified by column chromatography (SiO$_2$; 100-200 mesh; 20% EtOAc/Hexanes) to give 9-benzyl-2-chloro-6-(3, 3-difluoropyrrolidin-1-yl)-9H-purine (100 mg, 59%) as off white solid. LC-MS: 349.8 (M+H).

Example 155

(3S)-1-[2-tert-butyl-9-[(1-propan-2-yltetrazol-5-yl)methyl]purin-6-yl]pyrrolidin-3-ol

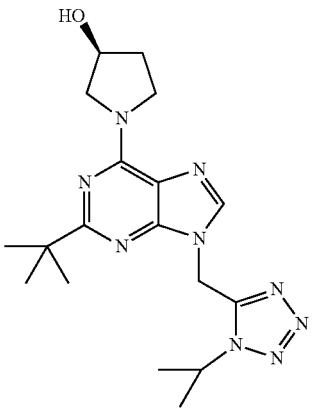 [SMILES: CC(C)n1nnnc1Cn1cnc2c(N3CC[C@H](O)C3)nc(C(C)(C)C)nc21]

a) 2-tert-butyl-6-chloro-9-((1-isopropyl-1H-tetrazol-5-yl)methyl)-9H-purine

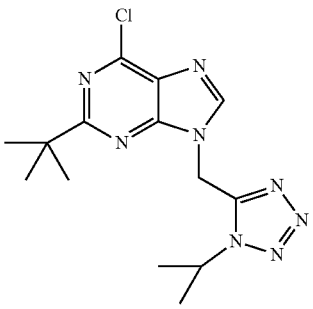 [SMILES: CC(C)n1nnnc1Cn1cnc2c(Cl)nc(C(C)(C)C)nc21]

NaH (60%, 49.4 mg, 1.23 mmol) was added to an ice cold solution of 2-tert-butyl-6-chloro-9H-purine (CAN 733736-31-7, 200 mg, 949 µmol) in DMF (4 mL). The reaction mixture was stirred at ambient temperature for 45 min. 5-(Chloromethyl)-1-isopropyl-1H-tetrazole (CAN 187739-97-5, 229 mg, 1.42 mmol) was added to the reaction mixture at 0 C and the reaction mixture was stirred at 60° C. for 12 h. Water (20 mL) was added and the mixture was extracted with EtOAc (3×20 mL). The organic layers were combined, dried over Na$_2$SO$_4$, filtered and concentrated in vacuo to give 446 mg of a brown solid which was purified by HPLC to give the title compound (218 mg, 69%) as white solid. MS(m/e): 335.2 (M+H).

b) (3S)-1-[2-tert-butyl-9-[(1-propan-2-yltetrazol-5-yl)methyl]purin-6-yl]pyrrolidin-3-ol DIPEA (CAN 7087-68-5, 29.0 mg, 38.3 µL, 224 µmol) and (S)-pyrrolidin-3-ol (CAN 100243-39-8, 14.3 mg, 13.7 µL, 164 µmol) were added to a solution of 2-tert-butyl-6-chloro-9-((1-isopropyl-1H-tetrazol-5-yl)methyl)-9H-purine (50 mg, 149 µmol) in acetonitrile (679 µL). The reaction mixture was stirred overnight at ambient temperature. 10% Aqueous citric acid was added and the mixture was

Example 156

2-tert-butyl-9-[(1-cyclopropyltetrazol-5-yl)methyl]-6-(3,3-difluoropyrrolidin-1-yl)purine

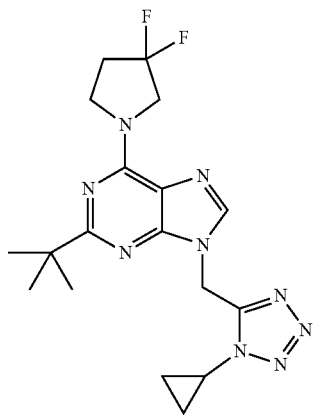 [SMILES: CC(C)(C)c1nc(N2CCC(F)(F)C2)c2ncn(Cc3nnnn3C3CC3)c2n1]

a) 2-tert-butyl-6-chloro-9-((1-cyclopropyl-1H-tetrazol-5-yl)methyl)-9H-purine

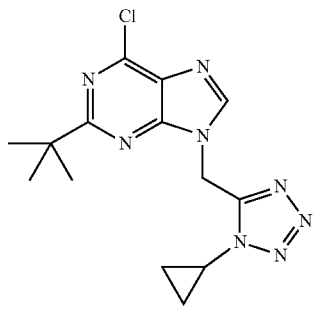 [SMILES: CC(C)(C)c1nc(Cl)c2ncn(Cc3nnnn3C3CC3)c2n1]

In analogy to the procedure described in example 155 a), 2-tert-butyl-6-chloro-9H-purine (CAN 733736-31-7, 400 mg, 1.9 mmol) was reacted with 5-(chloromethyl)-1-cyclopropyl-1H-tetrazole (CAN 949980-56-7, 452 mg, 2.85 mmol) to give the title compound (348 mg, 55%) as off-white solid. MS(m/e): 333.2 (M+H).

b) 2-tert-butyl-9-[(1-cyclopropyltetrazol-5-yl)methyl]-6-(3,3-difluoropyrrolidin-1-yl)purine In analogy to the procedure described in example 155 b), 2-tert-butyl-6-chloro-9-((1-cyclopropyl-1H-tetrazol-5-yl)methyl)-9H-purine (50 mg, 150 µmol) was reacted with 3,3-difluoropyrrolidine hydrochloride (CAN 163457-23-6, 23.7 mg, 165 µmol) to give the title compound (28 mg, 46%) as white solid. MS(m/e): 404.3 (M+H).

Example 157

[(2R)-1-[2-tert-Butyl-9-[(3-chloropyridin-2-yl)methyl]purin-6-yl]pyrrolidin-2-yl]methanol

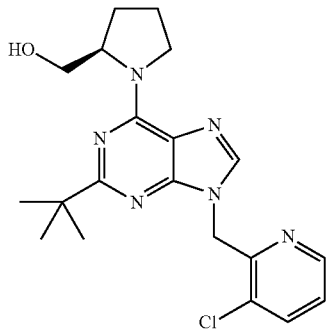 [SMILES: CC(C)(C)c1nc(N2CCC[C@@H]2CO)c2ncn(Cc3ncccc3Cl)c2n1]

a) 2-tert-butyl-6-chloro-9-((3-chloropyridin-2-yl)methyl)-9H-purine

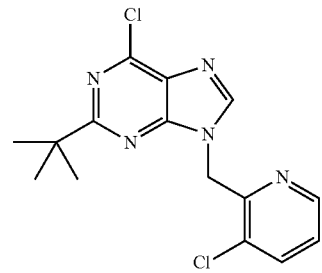 [SMILES: CC(C)(C)c1nc(Cl)c2ncn(Cc3ncccc3Cl)c2n1]

In analogy to the procedure described in example 155 a), 2-tert-butyl-6-chloro-9H-purine (CAN 733736-31-7, 500 mg, 2.37 mmol) was reacted with 3-chloro-2-(chloromethyl)pyridine hydrochloride (CAN 124425-87-2, 707 mg, 3.56 mmol) to give the title compound (208 mg, 26%) as off-white solid. MS(m/e): 336.4 (M+H).

b) [(2R)-1-[2-tert-Butyl-9-[(3-chloropyridin-2-yl)methyl]purin-6-yl]pyrrolidin-2-yl]methanol In analogy to the procedure described in example 155 b), 2-tert-butyl-6-chloro-9-((3-chloropyridin-2-yl)methyl)-9H-purine (40 mg, 119 µmol) was reacted with (R)-pyrrolidin-2-ylmethanol (CAN 68832-13-3, 13.2 mg, 12.9 µL, 131 µmol) to give the title compound (16 mg, 34%) as colorless solid. MS(m/e): 401.2 (M+H).

Example 158

(3S)-1-[2-tert-butyl-9-[(1-propyltetrazol-5-yl)methyl]purin-6-yl]pyrrolidin-3-ol

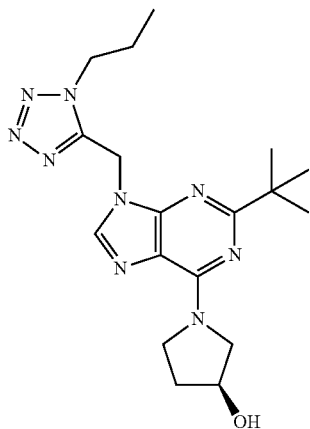 [SMILES: CCCn1nnnc1Cn1cnc2c(N3CC[C@H](O)C3)nc(C(C)(C)C)nc21]

a) (S)-1-(2-tert-butyl-9H-purin-6-yl)pyrrolidin-3-ol

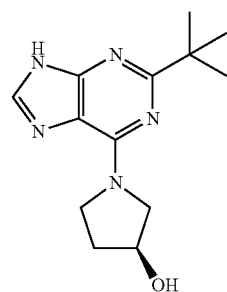 [SMILES: CC(C)(C)c1nc(N2CC[C@H](O)C2)c2nc[nH]c2n1]

DIPEA (CAN 7087-68-5, 123 mg, 166 µL, 949 µmol) was added to a solution of 2-tert-butyl-6-chloro-9H-purine (CAN 733736-31-7, 100 mg, 475 µmol) and (S)-pyrrolidin-3-ol (CAN 100243-39-8, 74.4 mg, 71.0 µL, 854 µmol) in MeCN (2.5 mL). The reaction was stirred for 24 h at ambient temperature. 10% Citric acid was added and the mixture was washed with DCM (2×20 mL). The aqueous layer was basified with NaHCO₃ and extracted with DCM (2×20 mL). The combined extracts were washed with brine, dried over Na₂SO₄ and concentrated in vacuo to give the title compound (50 mg, 80%) as white solid. MS(m/e): 262.5 (M+H).

b) (3S)-1-[2-tert-butyl-9-[(1-propyltetrazol-5-yl)methyl]purin-6-yl]pyrrolidin-3-ol DBU (CAN 6674-22-2, 93.8 mg, 92.9 µL, 616 µmol) was added to a solution of (S)-1-(2-tert-butyl-9H-purin-6-yl)pyrrolidin-3-ol (46 mg, 176 µmol) and 5-(chloromethyl)-1-propyl-1H-tetrazole (CAN 848178-47-2, 84.8 mg, 528 µmol) in DMF (1 mL). The reaction was stirred for 16 h at ambient temperature. Water/1N HCl (1:1), 20 mL) was added and the mixture was extracted with EtOAc (2×20 mL). The combined organic phases were washed sequentially with water and brine. The organic phase was dried over Na₂SO₄ and concentrated in vacuo to give the title compound (62 mg, 91%) as off-white foam. MS(m/e): 386.6 (M+H).

Example 159

(2R,3S)-1-[2-tert-butyl-9-[(3-chloropyridin-2-yl)methyl]purin-6-yl]-2-(hydroxymethyl)pyrrolidin-3-ol

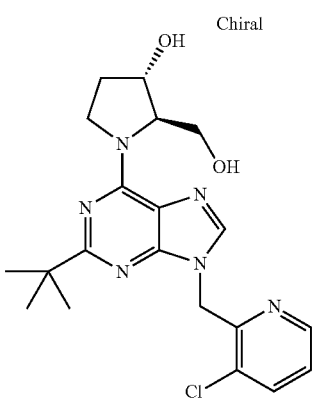 [SMILES: CC(C)(C)c1nc(N2CC[C@H](O)[C@H]2CO)c2ncn(Cc3ncccc3Cl)c2n1]

In analogy to the procedure described in example 155 b), 2-tert-butyl-6-chloro-9-((3-chloropyridin-2-yl)methyl)-9H-purine (Example 157 a, 40 mg, 119 µmol) was reacted with (2R,3S)-2-(hydroxymethyl)pyrrolidin-3-ol (CAN 105017-31-0, 13.9 mg, 119 µmol) to give the title compound (3 mg, 6%) as colorless solid. MS(m/e): 417.6 (M+H).

Example 160

2-tert-butyl-9-[(3-chloropyridin-2-yl)methyl]-6-(3,3-difluoroazetidin-1-yl)purine

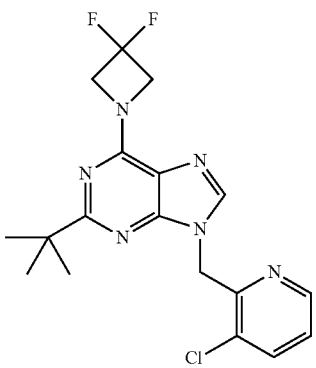 [SMILES: CC(C)(C)c1nc(N2CC(F)(F)C2)c2ncn(Cc3ncccc3Cl)c2n1]

In analogy to the procedure described in example 155 b), 2-tert-butyl-6-chloro-9-((3-chloropyridin-2-yl)methyl)-9H-purine (Example 157 a, 40 mg, 119 µmol) was reacted with 3,3-difluoroazetidine hydrochloride (CAN 288315-03-7, 30.8 mg, 238 µmol) to give the title compound (13 mg, 28%) as white solid. MS(m/e): 393.50 (M+H).

Example 161

3-[2-tert-butyl-9-[(3-chloropyridin-2-yl)methyl]purin-6-yl]-1,3-thiazolidine

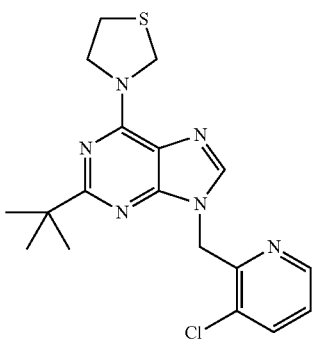 [SMILES: CC(C)(C)c1nc(N2CCSC2)c2ncn(Cc3ncccc3Cl)c2n1]

DIPEA (CAN 7087-68-5, 123 mg, 166 µL, 949 µmol) was added to a solution of 2-tert-butyl-6-chloro-9-((3-chloropyridin-2-yl)methyl)-9H-purine (Example 157 a, 37 mg, 110 µmol) and thiazolidine (CAN 504-78-9, 31.0 mg, 27.4 µL, 330 µmol) in dioxane (1 mL) and N,N-dimethylacetamide (122 µL). The reaction was stirred for 2.5 h at 120° C. Water was added and the reaction mixture was extracted with EtOAc (2×20 mL). The organic layers were combined, washed with brine, dried over Na$_2$SO$_4$ and concentrated in vacuo to give 39 mg of a yellow solid which was purified by flash chromatography (silica gel, 5 g, 0% to 35% EtOAc in heptane) and preparative HPLC to give the title compound (13 mg, 30%) as off-white solid. MS(m/e): 389.2 (M+H).

Example 162

6-[2-tert-butyl-9-[(3-chloropyridin-2-yl)methyl]purin-6-yl]-2λ6-thia-6-azaspiro[3.3]heptane 2,2-dioxide

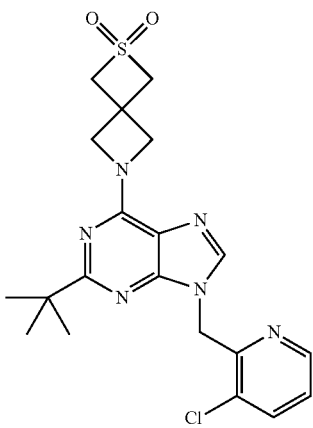 [SMILES: CC(C)(C)c1nc(N2CC3(C2)CS(=O)(=O)C3)c2ncn(Cc3ncccc3Cl)c2n1]

DIPEA (CAN 7087-68-5, 76.9 mg, 102 µL, 595 µmol) was added to a solution of 2-tert-butyl-6-chloro-9-((3-chloropyridin-2-yl)methyl)-9H-purine (Example 157 a, 40 mg, 119 µmol) and 2-thia-6-azaspiro[3.3]heptane, 2,2-dioxide (trifluoroacetic acid salt of CAN 1263182-09-7, 62.2 mg, 238 µmol) in dioxane (1.1 mL) and N,N-dimethylacetamide (131 µL). The reaction mixture was stirred for 16 h at 120° C. Water was added and the reaction mixture was extracted with EtOAc (2×20 mL). The organic layers were combined, washed with brine, dried over Na$_2$SO$_4$ and concentrated in vacuo to give 55 mg of a light brown solid which was purified by preparative TLC (silica gel, 1.0 mm, EtOAc) to give the title compound (27 mg, 51%) as white solid. MS(m/e): 447.2 (M+H).

Example 163

(2R)-1-[2-tert-Butyl-9-[(3-chloropyridin-2-yl)methyl]purin-6-yl]pyrrolidine-2-carbonitrile

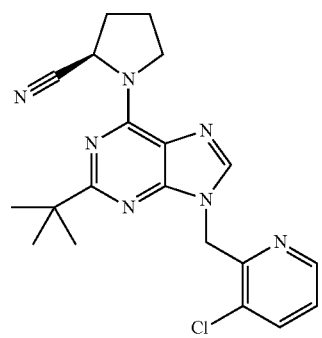 [SMILES: CC(C)(C)c1nc(N2CCC[C@@H]2C#N)c2ncn(Cc3ncccc3Cl)c2n1]

DIPEA (CAN 7087-68-5, 76.9 mg, 102 µL, 595 µmol) was added to a solution of 2-tert-butyl-6-chloro-9-((3-chloropyridin-2-yl)methyl)-9H-purine (Example 157 a, 40 mg, 119 µmol) and (R)-pyrrolidine-2-carbonitrile hydrochloride (CAN 675602-84-3, 47.3 mg, 357 µmol) in dioxane (623 µL). The reaction mixture was heated in the microwave oven for 30 min at 120° C. Water was added and the mixture was extracted with EtOAc (2×20 mL). The organic layers were combined, dried over Na$_2$SO$_4$ and concentrated in vacuo to give 38 mg of crude product which was purified by preparative TLC (silica gel, 1.0 mm, 1:1, Heptanes/EtOAc) to give the title compound (3 mg, 6%) as white solid. MS(m/e): 396.2 (M+H).

Example 164

(3S)-1-[2-tert-butyl-9-[[1-(cyclopropylmethyl)tetrazol-5-yl]methyl]purin-6-yl]pyrrolidin-3-ol

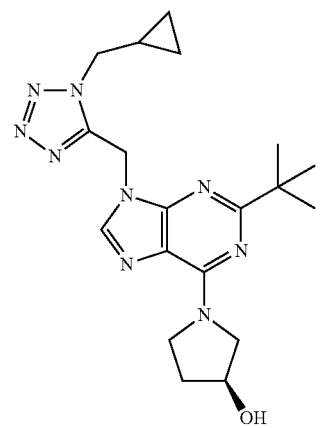 [SMILES: CC(C)(C)c1nc(N2CC[C@H](O)C2)c2ncn(Cc3nnnn3CC3CC3)c2n1]

In analogy to the procedure described in example 158 b), (S)-1-(2-tert-butyl-9H-purin-6-yl)pyrrolidin-3-ol (Example 158 a, 40 mg, 153 µmol) was reacted with 5-(chloromethyl)-1-(cyclopropylmethyl)-1H-tetrazole (CAN 1341701-60-7, 79.3 mg, 459 µmol) to give the title compound (45 mg, 74%) as white viscous oil. MS(m/e): 398.3 (M+H).

Example 165

1-[2-tert-butyl-9-[(3-chloropyridin-2-yl)methyl]purin-6-yl]-3-(trifluoromethyl)pyrrolidin-3-ol

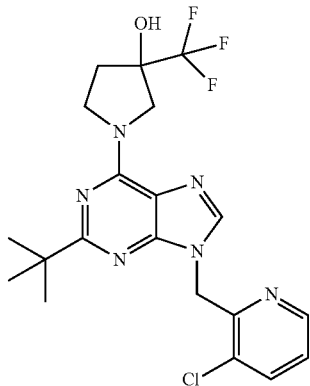 [SMILES: CC(C)(C)c1nc(N2CCC(O)(C(F)(F)F)C2)c2ncn(Cc3ncccc3Cl)c2n1]

DIPEA (CAN 7087-68-5, 46.1 mg, 61.1 µL, 357 µmol) was added to a solution of 2-tert-butyl-6-chloro-9-((3-chloropyridin-2-yl)methyl)-9H-purine (Example 157 a, 30 mg, 89.2 µmol) and 3-(trifluoromethyl)pyrrolidin-3-ol hydrochloride (CAN 1334147-81-7, 34.2 mg, 178 µmol) in NMP (1 mL). The reaction mixture was stirred for 16 h at 100° C. Water was added and the mixture was extracted with EtOAc (2×20 mL). The organic layers were combined, washed with brine, dried over Na₂SO₄ and concentrated in vacuo to give 76 mg of a dark brown oil which was purified by prep. TLC (silica gel, 2.0 mm, 1:1 Heptane/EtOAc) to give the title compound (29 mg, 72%) as off-white viscous oil. MS(m/e): 455.3 (M+H).

Example 166

(3S)-1-[2-tert-butyl-9-[(1-tert-butyltetrazol-5-yl)methyl]purin-6-yl]pyrrolidin-3-ol

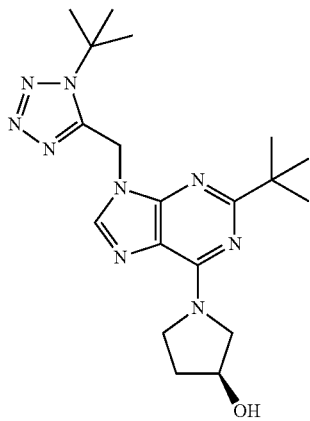 [SMILES: CC(C)(C)c1nc(N2CC[C@H](O)C2)c2ncn(Cc3nnnn3C(C)(C)C)c2n1]

In analogy to the procedure described in example 158 b), (S)-1-(2-tert-butyl-9H-purin-6-yl)pyrrolidin-3-ol (Example 158 a, 40 mg, 153 µmol) was reacted with 1-tert-butyl-5-(chloromethyl)-1H-tetrazole (CAN 75470-92-7, 88.1 mg, 459 µmol) to give the title compound (29 mg, 47%) as off-white solid. MS(m/e): 400.4 (M+H).

Example 167

1-[2-tert-butyl-9-[(3-chloropyridin-2-yl)methyl]purin-6-yl]-3-(trifluoromethyl)azetidin-3-ol

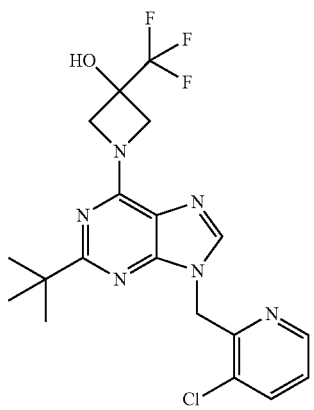 [SMILES: CC(C)(C)c1nc(N2CC(O)(C(F)(F)F)C2)c2ncn(Cc3ncccc3Cl)c2n1]

In analogy to the procedure described in example 171 a), 2-tert-butyl-6-chloro-9-((3-chloropyridin-2-yl)methyl)-9H-purine (Example 157 a, 30 mg, 89.2 µmol) was reacted with 3-(trifluoromethyl)azetidin-3-ol hydrochloride (CAN 848192-96-1, 31.7 mg, 178 µmol) to give the title compound (26 mg, 66%) as white solid. MS(m/e): 441.3 (M+H).

Example 168

2-tert-butyl-9-[(3-chloropyridin-2-yl)methyl]-6-(2,2-difluoro-5-azaspiro[2.4]heptan-5-yl)purine

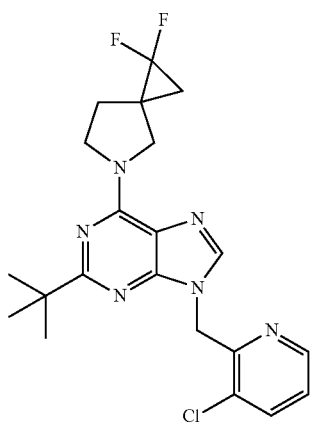 [SMILES: CC(C)(C)c1nc(N2CCC3(C2)CC3(F)F)c2ncn(Cc3ncccc3Cl)c2n1]

In analogy to the procedure described in example 171 a), 2-tert-butyl-6-chloro-9-((3-chloropyridin-2-yl)methyl)-9H-purine (Example 157 a, 29 mg, 86.3 µmol) was reacted with 1,1-difluoro-5-azaspiro[2.4]heptane hydrochloride (CAN 1215071-12-7, 29.3 mg, 173 µmol) to give the title compound (29 mg, 78%) as off-white solid. MS(m/e): 433.3 (M+H).

Example 169

1-[2-tert-butyl-9-[(3-chloropyridin-2-yl)methyl]purin-6-yl]-3-methylazetidin-3-ol

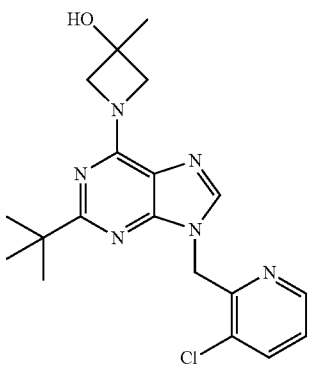 [SMILES: CC1(O)CN(c2nc(C(C)(C)C)nc3c2ncn3Cc2ncccc2Cl)C1]

In analogy to the procedure described in example 171 a), 2-tert-butyl-6-chloro-9-((3-chloropyridin-2-yl)methyl)-9H-purine (Example 157 a, 30 mg, 89.2 µmol) was reacted with 3-methylazetidin-3-ol hydrochloride (CAN 124668-46-8, 22.1 mg, 178 µmol) to give the title compound (11 mg, 32%) as colorless solid. MS(m/e): 387.3 (M+H).

Example 170

Pharmacological Tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM $MgCl_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 µM, more particularly of 1 nM to 3 µM and most particularly of 1 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1× HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. Using the cAMP-Nano-TRF detection kit the assay (Roche Diagnostics) was stopped by the addition of 50 µl lysis reagent (Tris, NaCl, 1.5% Triton X100, 2.5% NP40, 10% $NaN_3$) and 50 µl detection solutions (20 µM mAb Alexa700-cAMP 1:1, and 48 µM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

The compounds of the invention are CB2 receptor agonists with $EC_{50}$ below 1 µM and selectivity versus CB1 in the corresponding assay of at least 10 fold. Particular compound of the invention are CB2 receptor agonists with $EC_{50}$ below 0.05 µM and selectivity versus CB1 in the corresponding assay of at least 500 fold.

For example, the following compounds showed the following human $EC_{50}$ values in the functional cAMP assay described above:

| Example | EC50: CB2 | EC50: CB1 |
|---|---|---|
| 1 | 0.0116 | >10 |
| 2 | 0.0006 | 0.6766 |
| 3 | 0.0181 | >10 |
| 4 | 0.0031 | >10 |
| 5 | 0.0007 | 0.7406 |
| 6 | 0.0005 | 0.4331 |
| 7 | 0.0347 | >10 |
| 8 | 0.0753 | >10 |
| 9 | 0.0488 | >10 |
| 10 | 0.0498 | >10 |
| 11 | 0.0617 | >10 |
| 12 | 0.0031 | >10 |
| 13 | 0.0054 | 1.4971 |
| 14 | 0.023 | >10 |
| 15 | 0.0235 | >10 |
| 16 | 0.006 | >10 |
| 17 | 0.0035 | >10 |
| 18 | 0.0033 | >10 |
| 19 | 0.0352 | >10 |
| 20 | 0.0125 | >10 |
| 21 | 0.0022 | >10 |
| 22 | 0.0057 | >10 |
| 23 | 0.0044 | >10 |
| 24 | 0.0692 | >10 |
| 25 | 0.0588 | >10 |
| 26 | 0.0492 | >10 |
| 27 | 0.0141 | >10 |
| 28 | 0.001 | >10 |
| 29 | 0.4272 | >10 |
| 30 | 0.3007 | >10 |
| 31 | 0.0214 | >10 |
| 32 | 0.0034 | >10 |
| 33 | 0.0034 | >10 |
| 34 | 0.009 | >10 |

-continued

| Example | EC50: CB2 | EC50: CB1 |
|---|---|---|
| 35 | 0.4325 | >10 |
| 36 | 0.1504 | >10 |
| 37 | 0.2743 | >10 |
| 38 | 0.0203 | >10 |
| 39 | 0.0169 | >10 |
| 40 | 0.0712 | >10 |
| 41 | 0.0092 | 2.3294 |
| 42 | 0.0037 | >10 |
| 43 | 0.0166 | >10 |
| 44 | 0.0148 | >10 |
| 45 | 0.0496 | >10 |
| 46 | 0.1394 | >10 |
| 47 | 0.1015 | >10 |
| 48 | 0.1272 | >10 |
| 49 | 0.3109 | >10 |
| 50 | 0.5344 | >10 |
| 51 | 0.0647 | >10 |
| 52 | 0.2294 | >10 |
| 53 | 0.1753 | >10 |
| 54 | 0.3882 | >10 |
| 55 | 0.1378 | >10 |
| 56 | 0.0558 | >10 |
| 57 | 0.4665 | >10 |
| 58 | 0.5058 | >10 |
| 59 | 0.0167 | >10 |
| 60 | 0.1748 | >10 |
| 61 | 0.0296 | >10 |
| 62 | 0.1456 | >10 |
| 63 | 0.6606 | >10 |
| 64 | 0.0134 | >10 |
| 65 | 0.0916 | >10 |
| 66 | 0.2402 | >10 |
| 67 | 0.009 | >10 |
| 68 | 0.0248 | >10 |
| 69 | 0.0468 | >10 |
| 70 | 0.0595 | >10 |
| 71 | 0.6804 | >10 |
| 72 | 0.0124 | >10 |
| 73 | 0.1179 | >10 |
| 74 | 0.0884 | >10 |
| 75 | 0.2802 | >10 |
| 76 | 0.1531 | >10 |
| 77 | 0.2051 | >10 |
| 78 | 0.0175 | >10 |
| 79 | 0.1162 | >10 |
| 80 | 0.1793 | >10 |
| 81 | 0.0685 | 3.1197 |
| 82 | 0.0492 | >10 |
| 83 | 0.0646 | >10 |
| 84 | 0.0793 | >10 |
| 85 | 0.0221 | >10 |
| 86 | 0.0011 | >10 |
| 87 | 0.0021 | >10 |
| 88 | 0.0756 | >10 |
| 89 | 0.5726 | >10 |
| 90 | 0.0079 | >10 |
| 91 | 0.0017 | >10 |
| 92 | 0.0084 | >10 |
| 93 | 0.0898 | >10 |
| 94 | 0.4396 | >10 |
| 95 | 0.3632 | >10 |
| 96 | 0.0148 | >10 |
| 97 | 0.0018 | >10 |
| 98 | 0.0223 | >10 |
| 99 | 0.2276 | >10 |
| 100 | 0.0066 | >10 |
| 101 | 0.3699 | >10 |
| 102 | 0.1346 | >10 |
| 103 | 0.2111 | >10 |
| 104 | 0.1595 | >10 |
| 105 | 0.0089 | >10 |
| 106 | 0.0399 | >10 |
| 107 | 0.0081 | >10 |
| 108 | 0.0067 | >10 |
| 109 | 0.804 | >10 |
| 110 | 0.0183 | >10 |
| 111 | 0.0147 | >10 |

-continued

| Example | EC50: CB2 | EC50: CB1 |
|---|---|---|
| 112 | 0.0079 | >10 |
| 113 | 0.2487 | >10 |
| 114 | 0.0455 | >10 |
| 115 | 0.195 | >10 |
| 116 | 0.0121 | >10 |
| 117 | 0.0072 | >10 |
| 118 | 0.1521 | >10 |
| 119 | 0.1492 | >10 |
| 120 | 0.1077 | >10 |
| 121 | 0.0413 | >10 |
| 122 | 0.1524 | >10 |
| 123 | 0.5626 | >10 |
| 124 | 0.0027 | >10 |
| 125 | 0.0026 | >10 |
| 126 | 0.0245 | >10 |
| 127 | 0.3315 | >10 |
| 128 | 0.1089 | >10 |
| 129 | 0.0956 | >10 |
| 130 | 0.2149 | >10 |
| 131 | 0.0667 | >10 |
| 132 | 0.0221 | >10 |
| 133 | 0.1488 | >10 |
| 134 | 0.1783 | >10 |
| 135 | 0.0307 | >10 |
| 136 | 0.1499 | >10 |
| 137 | 0.0197 | >10 |
| 138 | 0.0781 | >10 |
| 139 | 0.201 | >10 |
| 140 | 0.0092 | >10 |
| 141 | 0.0409 | >10 |
| 142 | 0.6806 | >10 |
| 143 | 0.268 | >10 |
| 144 | 0.2107 | >10 |
| 145 | 0.0061 | >10 |
| 146 | 0.0551 | >10 |
| 147 | 0.1755 | >10 |
| 148 | 0.0157 | >10 |
| 149 | 0.1848 | >10 |
| 150 | 0.0105 | >10 |
| 151 | 0.0287 | >10 |
| 152 | 0.431 | >10 |
| 153 | 0.1102 | >10 |
| 154 | 0.2109 | >10 |
| 155 | 0.0823 | >10 |
| 156 | 0.0091 | >10 |
| 157 | 0.0043 | >10 |
| 158 | 0.0616 | >10 |
| 159 | 0.5913 | >10 |
| 160 | 0.01551 | >10 |
| 161 | 0.01259 | >10 |
| 162 | 0.0701 | 0.3277 |
| 163 | 0.0069 | >10 |
| 164 | 0.0207 | >10 |
| 165 | 0.0624 | 4.0242 |
| 166 | 0.1034 | >10 |
| 167 | 0.035 | >10 |
| 168 | 0.0324 | >10 |
| 169 | 0.0514 | >10 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |

-continued

| Ingredients | Per tablet | |
|---|---|---|
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound of formula (I)

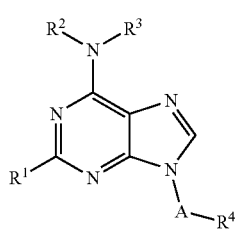

wherein
A is $CH_2$, $CH_2CH_2$, $CH_2CO$ or absent;
$R^1$ is tert-butyl, tert-butylamino, or 2,2-dimethylpropyloxy;
$R^2$ and $R^3$, together with the nitrogen atom to which they are attached, form pyrrolidinyl, substituted pyrrolidinyl, thiazolidinyl, alkylpiperazinyl, 2-oxa-7-azaspiro[3.4]octyl, 2-oxa-6-azaspiro[3.3]heptyl, azetidinyl, substituted azetidinyl, 2,2-dioxo-2$\lambda^6$-thia-6-azaspiro[3.3]heptyl or halo-5-azaspiro[2.4]heptyl, wherein substituted pyrrolidinyl is pyrrolidinyl substituted with one to four substituents independently selected from halogen, hydroxyl, alkyl, hydroxyalkyl, cyano, alkylcarbonylamino, alkylcarbonyloxy and haloalkyl and wherein substituted azetidinyl is azetidinyl substituted with one or two substituents selected from halogen, hydroxyl, alkyl and haloalkyl; and
$R^4$ is hydrogen, phenyl, halophenyl, alkylphenyl, haloalkylphenyl, pyridinyl, halopyridinyl, cycloalkyl, alkyl, alkyloxadiazolyl, oxolanyl, alkyltetrazolyl, alkoxy, alkylsulfonylphenyl, haloalkyl, alkoxyphenyl, dioxothietanyl, cycloalkyltetrazolyl, haloalkyl-1H-pyrazolyl or cycloalkylalkyltetrazolyl;
or a pharmaceutically acceptable salt or ester thereof.

2. A compound according to claim 1, wherein A is $CH_2$.

3. A compound according to claim 1, wherein $R^1$ is tert.-butyl or 2,2-dimethylpropyloxy.

4. A compound according to claim 1, wherein $R^2$ and $R^3$, together with the nitrogen atom to which they are attached, form thiazolidinyl, substituted pyrrolidinyl or substituted azetidinyl, wherein substituted pyrrolidinyl is pyrrolidinyl substituted with one or two substituents independently selected from halogen, hydroxyl, hydroxyalkyl and cyano and wherein substituted azetidinyl is azetidinyl substituted with one or two substituents selected from halogen, hydroxyl and haloalkyl.

5. A compound according to claim 1, wherein $R^2$ and $R^3$, together with the nitrogen atom to which they are attached, form thiazolidinyl, substituted pyrrolidinyl or substituted azetidinyl, wherein substituted pyrrolidinyl is pyrrolidinyl substituted with one or two substituents independently selected from fluorine, hydroxyl, hydroxymethyl and cyano and wherein substituted azetidinyl is azetidinyl substituted with one or two substituents selected from fluorine, hydroxyl and trifluoromethyl.

6. A compound according to claim 1, wherein $R^2$ and $R^3$, together with the nitrogen atom to which they are attached, form thiazolidinyl, difluoropyrrolidinyl, hydroxypyrrolidinyl, hydroxymethylpyrrolidinyl, cyanopyrrolidinyl, difluoroazetidinyl or (hydroxyl)(trifluoromethyl)azetidinyl.

7. A compound according to claim 1, wherein $R^4$ is halophenyl, haloalkylphenyl, halopyridinyl, oxolanyl, alkyl sulfonylphenyl, pyridinyl or cycloalkyltetrazolyl.

8. A compound according to claim 1, wherein $R^4$ is chlorophenyl, chlorofluorophenyl, trifluoromethylphenyl, chloropyridinyl, oxolanyl, methyl sulfonylphenyl, pyridinyl or cyclopropyltetrazolyl.

9. A compound according to claim 1 selected from:
2-tert-butyl-9-[(4-chlorophenyl)methyl]-6-(3,3-difluoropyrrolidin-1-yl)purine;
2-tert-butyl-9-[(2-chlorophenyl)methyl]-6-(3,3-difluoropyrrolidin-1-yl)purine;
2-tert-butyl-6-(3,3-difluoropyrrolidin-1-yl)-9-[(4-methylphenyl)methyl]purine;
2-tert-butyl-9-[(2-chloro-4-fluorophenyl)methyl]-6-(3,3-difluoropyrrolidin-1-yl)purine;

2-tert-butyl-6-(3,3-difluoropyrrolidin-1-yl)-9-[[2-(trifluoromethyl)phenyl]methyl] purine;
2-tert-butyl-9-[(2-chloropyridin-3-yl)methyl]-6-(3,3-difluoropyrrolidin-1-yl)purine;
5-[[2-tert-butyl-6-(3,3-difluoropyrrolidin-1-yl)purin-9-yl]methyl]-3-methyl-1,2,4-oxadiazole;
2-tert-butyl-9-(cyclohexylmethyl)-6-(3,3-difluoropyrrolidin-1-yl)purine;
2-tert-butyl-6-(3,3-difluoropyrrolidin-1-yl)-9-ethylpurine;
2-tert-butyl-6-(3,3-difluoropyrrolidin-1-yl)-9-propylpurine;
2-[[2-tert-butyl-6-(3,3-difluoropyrrolidin-1-yl)purin-9-yl]methyl]-5-methyl-1,3,4-oxadiazole;
2-tert-butyl-6-(3,3-difluoropyrrolidin-1-yl)-9-(oxolan-3-yl)purine;
2-tert-butyl-6-(3,3-difluoropyrrolidin-1-yl)-9-(2-phenylethyl)purine;
2-tert-butyl-6-(3,3-difluoropyrrolidin-1-yl)-9-[(1-methyltetrazol-5-yl)methyl]purine;
2-tert-butyl-6-(3,3-difluoropyrrolidin-1-yl)-9-(2-methoxyethyl)purine;
3-[[2-tert-butyl-6-(3,3-difluoropyrrolidin-1-yl)purin-9-yl]methyl]-4-methyl-1,2,5-oxadiazole;
2-[2-tert-butyl-6-(3,3-difluoropyrrolidin-1-yl)purin-9-yl]-1-(2-chlorophenyl) ethanone;
2-tert-butyl-6-(3,3-difluoropyrrolidin-1-yl)-9-[(2-methylsulfonylphenyl)methyl] purine;
2-tert-butyl-6-(3,3-difluoropyrrolidin-1-yl)-9-(3,3,3-trifluoropropyl)purine;
2-tert-butyl-6-(3,3-difluoropyrrolidin-1-yl)-9-[(4-methoxyphenyl)methyl]purine;
2-tert-butyl-9-[(3-chloropyridin-2-yl)methyl]-6-(3,3-difluoropyrrolidin-1-yl)purine;
1-[2-tert-butyl-9-[(2-chlorophenyl)methyl]purin-6-yl]pyrrolidin-3-ol;
2-tert-butyl-6-(3,3-difluoropyrrolidin-1-yl)-9-(2-pyridin-3-ylethyl)purine;
2-[2-tert-butyl-6-(3,3-difluoropyrrolidin-1-yl)purin-9-yl]-1-pyridin-2-ylethanone;
1-[2-tert-butyl-9-[(3-chlorophenyl)methyl]purin-6-yl]pyrrolidin-3-ol;
1-[2-tert-butyl-9-[(4-chlorophenyl)methyl]purin-6-yl]pyrrolidin-3-ol;
3-[2-tert-butyl-6-(3,3-difluoropyrrolidin-1-yl)purin-9-yl] thietane 1,1-dioxide;
1-[2-tert-butyl-9-[[2-(trifluoromethyl)phenyl]methyl]purin-6-yl]pyrrolidin-3-ol;
1-[2-tert-butyl-9-[(3-methyl-1,2,4-oxadiazol-5-yl)methyl]purin-6-yl]pyrrolidin-3-ol;
1-[2-tert-butyl-9-[(1-methyltetrazol-5-yl)methyl]purin-6-yl]pyrrolidin-3-ol;
1-[2-tert-butyl-9-[(4-methoxyphenyl)methyl]purin-6-yl]pyrrolidin-3-ol;
1-[2-tert-butyl-9-[(3-chloropyridin-2-yl)methyl]purin-6-yl]pyrrolidin-3-ol;
1-[2-tert-butyl-9-[(2-chloropyridin-3-yl)methyl]purin-6-yl]pyrrolidin-3-ol;
1-[2-tert-butyl-9-[(2-methylsulfonylphenyl)methyl]purin-6-yl]pyrrolidin-3-ol;
1-(2-tert-butyl-9-ethylpurin-6-yl)pyrrolidin-3-ol;
1-(2-tert-butyl-9-propylpurin-6-yl)pyrrolidin-3-ol;
1-[2-tert-butyl-9-(2-methoxyethyl)purin-6-yl]pyrrolidin-3-ol;
1-[2-tert-butyl-9-(2-phenylethyl)purin-6-yl]pyrrolidin-3-ol;
1-[2-tert-butyl-9-[(4-methylphenyl)methyl]purin-6-yl]pyrrolidin-3-ol;
1-[2-tert-butyl-9-(cyclohexylmethyl)purin-6-yl]pyrrolidin-3-ol;
2-tert-butyl-6-(3,3-difluoropyrrolidin-1-yl)-9-[[3-(trifluoromethyl)-1H-pyrazol-4-yl]methyl]purine;
1-[2-tert-butyl-9-[(2-chloro-4-fluorophenyl)methyl]purin-6-yl]pyrrolidin-3-ol;
1-[2-tert-butyl-9-[(4-methyl-1,2,5-oxadiazol-3-yl)methyl]purin-6-yl]pyrrolidin-3-ol;
1-[2-tert-butyl-9-[[3-(trifluoromethyl)-1H-pyrazol-4-yl]methyl]purin-6-yl]pyrrolidin-3-ol;
1-[2-tert-butyl-9-(3,3,3-trifluoropropyl)purin-6-yl]pyrrolidin-3-ol;
1-[2-tert-butyl-9-(oxolan-3-yl)purin-6-yl]pyrrolidin-3-ol;
2-[2-tert-butyl-6-(3-hydroxypyrrolidin-1-yl)purin-9-yl]-1-(2-chlorophenyl)ethanone;
N—{(S)-1-[2-tert-Butyl-9-(2-chloro-benzyl)-9H-purin-6-yl]-pyrrolidin-3-yl}-acetamide;
N—[(S)-1-[2-tert-butyl-9-[(3-chlorophenyl)methyl]purin-6-yl]pyrrolidin-3-yl]acetamide;
N—[(S)-1-[2-tert-butyl-9-[(4-chlorophenyl)methyl]purin-6-yl]pyrrolidin-3-yl]acetamide;
N—[(S)-1-[2-tert-butyl-9-[[2-(trifluoromethyl)phenyl]methyl]purin-6-yl]pyrrolidin-3-yl]acetamide;
N—[(S)-1-[2-tert-butyl-9-[(2-methylsulfonylphenyl)methyl]purin-6-yl]pyrrolidin-3-yl]acetamide;
N—[(S)-1-[2-tert-butyl-9-[(2-chloropyridin-3-yl)methyl]purin-6-yl]pyrrolidin-3-yl]acetamide;
N—[(S)-1-[2-tert-butyl-9-[(3-chloropyridin-2-yl)methyl]purin-6-yl]pyrrolidin-3-yl]acetamide
N—[(S)-1-[2-tert-butyl-9-[(4-methyl-1,2,5-oxadiazol-3-yl)methyl]purin-6-yl]pyrrolidin-3-yl]acetamide;
7-[2-tert-butyl-9-[(2-chlorophenyl)methyl]purin-6-yl]-2-oxa-7-azaspiro[3.4]octane;
7-[2-tert-butyl-9-[(3-chlorophenyl)methyl]purin-6-yl]-2-oxa-7-azaspiro[3.4]octane;
7-[2-tert-butyl-9-[(4-chlorophenyl)methyl]purin-6-yl]-2-oxa-7-azaspiro[3.4]octane;
7-[2-tert-butyl-9-[[2-(trifluoromethyl)phenyl]methyl]purin-6-yl]-2-oxa-7-azaspiro[3.4]octane;
7-[2-tert-butyl-9-[(2-methylsulfonylphenyl)methyl]purin-6-yl]-2-oxa-7-azaspiro[3.4]octane;
7-[2-tert-butyl-9-[(2-chloropyridin-3-yl)methyl]purin-6-yl]-2-oxa-7-azaspiro[3.4]octane;
7-[2-tert-butyl-9-[(4-methyl-1,2,5-oxadiazol-3-yl)methyl]purin-6-yl]-2-oxa-7-azaspiro[3.4]octane;
7-[2-tert-butyl-9-(2-methoxyethyl)purin-6-yl]-2-oxa-7-azaspiro[3.4] octane;
1-[2-tert-butyl-9-[(2-chlorophenyl)methyl]purin-6-yl]-3-methylpyrrolidin-3-ol;
1-[2-tert-butyl-9-[(3-chlorophenyl)methyl]purin-6-yl]-3-methylpyrrolidin-3-ol;
1-[2-tert-butyl-9-[(4-chlorophenyl)methyl]purin-6-yl]-3-methylpyrrolidin-3-ol;
1-[2-tert-butyl-9-[[2-(trifluoromethyl)phenyl]methyl]purin-6-yl]-3-methylpyrrolidin-3-ol;
1-[2-tert-butyl-9-[(2-chloropyridin-3-yl)methyl]purin-6-yl]-3-methylpyrrolidin-3-ol;
1-[2-tert-butyl-9-[(3-chloropyridin-2-yl)methyl]purin-6-yl]-3-methylpyrrolidin-3-ol;
1-[2-tert-butyl-9-[(4-methyl-1,2,5-oxadiazol-3-yl)methyl]purin-6-yl]-3-methylpyrrolidin-3-ol;
1-[2-tert-butyl-9-(2-methoxyethyl)purin-6-yl]-3-methylpyrrolidin-3-ol;
2-tert-butyl-9-[(2-chlorophenyl)methyl]-6-(3,3,4,4-tetrafluoropyrrolidin-1-yl)purine;

2-tert-butyl-9-[(3-chlorophenyl)methyl]-6-(3,3,4,4-tetrafluoropyrrolidin-1-yl)purine;
1-[2-tert-butyl-9-[(2-methylsulfonylphenyl)methyl]purin-6-yl]-3-methylpyrrolidin-3-ol;
N—[(S)-1-[2-tert-butyl-9-[[3-(trifluoromethyl)-1H-pyrazol-4-yl]methyl]purin-6-yl]pyrrolidin-3-yl]acetamide;
7-[2-tert-butyl-9-[[3-(trifluoromethyl)-1H-pyrazol-4-yl]methyl]purin-6-yl]-2-oxa-7-azaspiro[3.4]octane;
N—[(S)-1-[2-tert-butyl-9-[[4-(trifluoromethyl)-1H-pyrazol-3-yl]methyl]purin-6-yl]pyrrolidin-3-yl]acetamide;
7-[2-tert-butyl-9-[[4-(trifluoromethyl)-1H-pyrazol-3-yl]methyl]purin-6-yl]-2-oxa-7-azaspiro[3.4]octane;
2-[[2-tert-butyl-6-(3,3,4,4-tetrafluoropyrrolidin-1-yl)purin-9-yl]methyl]-5-methyl-1,3,4-oxadiazole;
5-[[2-tert-butyl-6-(3,3,4,4-tetrafluoropyrrolidin-1-yl)purin-9-yl]methyl]-3-methyl-1,2,4-oxadiazole;
2-tert-butyl-9-[(1-methyltetrazol-5-yl)methyl]-6-(3,3,4,4-tetrafluoropyrrolidin-1-yl)purine;
3-[[2-tert-butyl-6-(3,3,4,4-tetrafluoropyrrolidin-1-yl)purin-9-yl]methyl]-4-methyl-1,2,5-oxadiazole;
2-tert-butyl-9-(2-methoxyethyl)-6-(3,3,4,4-tetrafluoropyrrolidin-1-yl)purine;
1-[2-tert-butyl-9-[[3-(trifluoromethyl)-1H-pyrazol-4-yl]methyl]purin-6-yl]-3-methylpyrrolidin-3-ol;
1-[2-tert-butyl-9-[[4-(trifluoromethyl)-1H-pyrazol-3-yl]methyl]purin-6-yl]-3-methylpyrrolidin-3-ol;
(3S)-1-[2-tert-butyl-9-[[2-(trifluoromethyl)phenyl]methyl]purin-6-yl]pyrrolidin-3-ol;
(3S)-1-[2-tert-butyl-9-[(3-chlorophenyl)methyl]purin-6-yl]pyrrolidin-3-ol;
(3S)-1-[2-tert-butyl-9-[(4-chlorophenyl)methyl]purin-6-yl]pyrrolidin-3-ol;
7-[2-tert-butyl-9-(3,3,3-trifluoropropyl)purin-6-yl]-2-oxa-7-azaspiro[3.4] octane;
(3S)-1-[2-tert-butyl-9-[(2-methyl sulfonylphenyl)methyl]purin-6-yl]pyrrolidin-3-ol;
(3S)-1-[2-tert-butyl-9-[(2-chloropyridin-3-yl)methyl]purin-6-yl]pyrrolidin-3-ol;
(3S)-1-[2-tert-butyl-9-[(3-chloropyridin-2-yl)methyl]purin-6-yl]pyrrolidin-3-ol;
2-tert-butyl-6-(3,3,4,4-tetrafluoropyrrolidin-1-yl)-9-(3,3,3-trifluoropropyl)purine;
(3S)-1-[2-tert-butyl-9-(2-methoxyethyl)purin-6-yl]pyrrolidin-3-ol;
(3S)-1-[2-tert-butyl-9-[(1-methyltetrazol-5-yl)methyl]purin-6-yl]pyrrolidin-3-ol;
(3S)-1-[2-tert-butyl-9-[(4-methyl-1,2,5-oxadiazol-3-yl)methyl]purin-6-yl]pyrrolidin-3-ol;
(3S)-1-[2-tert-butyl-9-[(2-chlorophenyl)methyl]purin-6-yl]pyrrolidin-3-ol;
(3S)-1-[2-tert-butyl-9-[[3-(trifluoromethyl)-1H-pyrazol-4-yl]methyl]purin-6-yl]pyrrolidin-3-ol;
(3S)-1-[2-tert-butyl-9-(3,3,3-trifluoropropyl)purin-6-yl]pyrrolidin-3-ol;
(3S)-1-[2-tert-butyl-9-[[4-(trifluoromethyl)-1H-pyrazol-3-yl]methyl]purin-6-yl]pyrrolidin-3-ol;
(3S)-1-[2-tert-butyl-9-[(3-methyl-1,2,4-oxadiazol-5-yl)methyl]purin-6-yl]pyrrolidin-3-ol;
1-[2-tert-butyl-9-(3,3,3-trifluoropropyl)purin-6-yl]-3-methylpyrrolidin-3-ol;
N-[(3S)-1-[2-tert-butyl-9-(3,3,3-trifluoropropyl)purin-6-yl]pyrrolidin-3-yl] acetamide;
7-[2-tert-butyl-9-[(3-chloropyridin-2-yl)methyl]purin-6-yl]-2-oxa-7-azaspiro[3.4]octane;
2-tert-butyl-6-(3,3,4,4-tetrafluoropyrrolidin-1-yl)-9-[[2-(trifluoromethyl)phenyl]methyl]purine;
2-tert-butyl-9-[(2-methyl sulfonylphenyl)methyl]-6-(3,3,4,4-tetrafluoropyrrolidin-1-yl)purine;
N-tert-butyl-9-[(2-chlorophenyl)methyl]-6-(3,3-difluoropyrrolidin-1-yl)purin-2-amine;
N-tert-butyl-6-(3,3-difluoropyrrolidin-1-yl)-9-[[2-(trifluoromethyl)phenyl] methyl]purin-2-amine;
N-tert-butyl-6-(3,3-difluoropyrrolidin-1-yl)-9-[(5-methyl-1,3,4-oxadiazol-2-yl)methyl]purin-2-amine;
N-tert-butyl-6-(3,3-difluoropyrrolidin-1-yl)-9-(3,3,3-trifluoropropyl)purin-2-amine;
N-tert-butyl-6-(3,3-difluoropyrrolidin-1-yl)-9-[(4-methyl-1,2,5-oxadiazol-3-yl)methyl]purin-2-amine;
N-tert-butyl-9-[(3-chloropyridin-2-yl)methyl]-6-(3,3-difluoropyrrolidin-1-yl)purin-2-amine;
N-tert-butyl-6-(3,3-difluoropyrrolidin-1-yl)-9-[(1-methyltetrazol-5-yl)methyl]purin-2-amine;
N-tert-butyl-6-(3,3-difluoropyrrolidin-1-yl)-9-[(2-methylsulfonylphenyl)methyl]purin-2-amine;
N-tert-butyl-6-(3,3-difluoropyrrolidin-1-yl)-9-[(3-methyl-1,2,4-oxadiazol-5-yl)methyl]purin-2-amine;
(3S)-1-[2-(tert-butyl amino)-9-[(2-chlorophenyl)methyl]purin-6-yl]pyrrolidin-3-ol;
(3S)-1-[2-(tert-butylamino)-9-[[2-(trifluoromethyl)phenyl]methyl]purin-6-yl]pyrrolidin-3-ol;
(3S)-1-[2-(tert-butylamino)-9-[(3-chloropyridin-2-yl)methyl]purin-6-yl]pyrrolidin-3-ol;
(3S)-1-[2-(tert-butylamino)-9-[(4-methyl-1,2, 5-oxadiazol-3-yl)methyl]purin-6-yl]pyrrolidin-3-ol;
1-[2-(tert-butylamino)-9-[(2-chlorophenyl)methyl]purin-6-yl]-3-methylpyrrolidin-3-ol;
1-[2-(tert-butylamino)-9-[[2-(trifluoromethyl)phenyl]methyl]purin-6-yl]-3-methylpyrrolidin-3-ol;
(3S)-1-[2-(tert-butylamino)-9-[[3-(trifluoromethyl)-1H-pyrazol-4-yl]methyl]purin-6-yl]pyrrolidin-3-ol;
1-[2-(tert-butylamino)-9-[(4-methyl-1,2,5-oxadiazol-3-yl)methyl]purin-6-yl]-3-methylpyrrolidin-3-ol;
9-[(2-chlorophenyl)methyl]-6-(3,3-difluoropyrrolidin-1-yl)-2-(2,2-dimethylpropoxy)purine;
6-(3,3-difluoropyrrolidin-1-yl)-2-(2,2-dimethylpropoxy)-9-[[2-(trifluoromethyl)phenyl]methyl]purine;
6-(3,3-difluoropyrrolidin-1-yl)-2-(2,2-dimethylpropoxy)-9-[(2-methyl sulfonylphenyl)methyl]purine;
2-[[6-(3,3-difluoropyrrolidin-1-yl)-2-(2,2-dimethylpropoxy)purin-9-yl]methyl]-5-methyl-1,3,4-oxadiazole;
5-[[6-(3,3-difluoropyrrolidin-1-yl)-2-(2,2-dimethylpropoxy)purin-9-yl]methyl]-3-methyl-1,2,4-oxadiazole;
6-(3,3-difluoropyrrolidin-1-yl)-2-(2,2-dimethylpropoxy)-9-[(1-methyltetrazol-5-yl)methyl]purine;
(3S)-1-[2-(tert-butylamino)-9-(3,3,3-trifluoropropyl)purin-6-yl]pyrrolidin-3-ol;
1-[9-[(2-chlorophenyl)methyl]-2-(2,2-dimethylpropoxy)purin-6-yl]-3-methylpyrrolidin-3-ol;
1-[2-(2,2-dimethylpropoxy)-9-[[2-(trifluoromethyl)phenyl]methyl]purin-6-yl]-3-methylpyrrolidin-3-ol;
1-[2-(2,2-dimethylpropoxy)-9-[(2-methylsulfonylphenyl)methyl]purin-6-yl]-3-methylpyrrolidin-3-ol;
1-[9-[(3-chloropyridin-2-yl)methyl]-2-(2,2-dimethylpropoxy)purin-6-yl]-3-methylpyrrolidin-3-ol;
1-[2-(2,2-dimethylpropoxy)-9-[(4-methyl-1,2,5-oxadiazol-3-yl)methyl]purin-6-yl]-3-methylpyrrolidin-3-ol;
1-[2-(tert-butylamino)-9-[[3-(trifluoromethyl)-1H-pyrazol-4-yl]methyl]purin-6-yl]-3-methylpyrrolidin-3-ol;
N-tert-butyl-6-(2-oxa-6-azaspiro[3.3]heptan-6-yl)-9-[[2-(trifluoromethyl)phenyl]methyl]purin-2-amine;

N-tert-butyl-9-[(2-chlorophenyl)methyl]-6-(2-oxa-6-azaspiro[3.3]heptan-6-yl)purin-2-amine;
(3S)-1-[2-tert-butyl-9-[(1-cyclopropyltetrazol-5-yl)methyl]purin-6-yl]pyrrolidin-3-ol;
3-[[6-(3,3-difluoropyrrolidin-1-yl)-2-(2,2-dimethylpropoxy)purin-9-yl]methyl]-4-methyl-1,2,5-oxadiazole;
N-tert-butyl-9-[(3-methyl-1,2,4-oxadiazol-5-yl)methyl]-6-(2-oxa-6-azaspiro[3.3]heptan-6-yl)purin-2-amine;
N-tert-butyl-6-(2-oxa-6-azaspiro[3.3]heptan-6-yl)-9-(3,3,3-trifluoropropyl)purin-2-amine;
6-[9-[(2-chlorophenyl)methyl]-2-(2,2-dimethylpropoxy)purin-6-yl]-2-oxa-6-azaspiro[3.3]heptane;
3-[[2-tert-butyl-6-(4-methylpiperazin-1-yl)purin-9-yl]methyl]-4-methyl-1,2,5-oxadiazole;
[(2R)-1-[2-tert-butyl-9-[(4-methyl-1,2,5-oxadiazol-3-yl)methyl]purin-6-yl]pyrrolidin-2-yl]methanol;
[(2R)-1-[2-tert-butyl-9-[(1-cyclopropyltetrazol-5-yl)methyl]purin-6-yl]pyrrolidin-2-yl]methanol;
(2R)-1-[2-tert-butyl-9-[(1-cyclopropyltetrazol-5-yl)methyl]purin-6-yl]pyrrolidine-2-carbonitrile;
(2R)-1-[2-tert-butyl-9-[(4-methyl-1,2,5-oxadiazol-3-yl)methyl]purin-6-yl]pyrrolidine-2-carbonitrile;
6-[2-tert-butyl-9-[(4-methyl-1,2,5-oxadiazol-3-yl)methyl]purin-6-yl]-2-oxa-6-azaspiro[3.3]heptane;
3-[[2-tert-butyl-6-(1,3-thiazolidin-3-yl)purin-9-yl]methyl]-4-methyl-1,2, 5-oxadiazole;
6-(3,3-Difluoropyrrolidin-1-yl)-2-(2,2-dimethylpropoxy)-9H-purine;
[(3S)-1-[2-(tert-Butylamino)-9-[(4-methyl-1,2,5-oxadiazol-3-yl)methyl]purin-6-yl]pyrrolidin-3-yl] acetate;
[1-[2-(tert-Butylamino)-9-[(4-methyl-1,2,5-oxadiazol-3-yl)methyl]purin-6-yl]-3-methylpyrrolidin-3-yl] acetate;
(3S)-1-[2-tert-Butyl-9-[(1-propan-2-yltetrazol-5-yl)methyl]purin-6-yl]pyrrolidin-3-ol;
2-tert-Butyl-9-[(1-cyclopropyltetrazol-5-yl)methyl]-6-(3,3-difluoropyrrolidin-1-yl)purine;
[(2R)-1-[2-tert-Butyl-9-[(3-chloropyridin-2-yl)methyl]purin-6-yl]pyrrolidin-2-yl]methanol;
(3S)-1-[2-tert-Butyl-9-[(1-propyltetrazol-5-yl)methyl]purin-6-yl]pyrrolidin-3-ol;
(2R,3S)-1-[2-tert-Butyl-9-[(3-chloropyridin-2-yl)methyl]purin-6-yl]-2-(hydroxymethyl)pyrrolidin-3-ol;
2-tert-Butyl-9-[(3-chloropyridin-2-yl)methyl]-6-(3,3-difluoroazetidin-1-yl)purine;
3-[2-tert-Butyl-9-[(3-chloropyridin-2-yl)methyl]purin-6-yl]-1,3-thiazolidine;
6-[2-tert-Butyl-9-[(3-chloropyridin-2-yl)methyl]purin-6-yl]-2λ6-thia-6-azaspiro[3.3]heptane 2,2-dioxide;
(2R)-1-[2-tert-Butyl-9-[(3-chloropyridin-2-yl)methyl]purin-6-yl]pyrrolidine-2-carbonitrile;
(3S)-1-[2-tert-Butyl-9-[[1-(cyclopropylmethyl)tetrazol-5-yl]methyl]purin-6-yl]pyrrolidin-3-ol;
1-[2-tert-Butyl-9-[(3-chloropyridin-2-yl)methyl]purin-6-yl]-3-(trifluoromethyl)pyrrolidin-3-ol;
(3S)-1-[2-tert-Butyl-9-[(1-tert-butyltetrazol-5-yl)methyl]purin-6-yl]pyrrolidin-3-ol;
1-[2-tert-butyl-9-[(3-chloropyridin-2-yl)methyl]purin-6-yl]-3-(trifluoromethyl)azetidin-3-ol;
2-tert-Butyl-9-[(3-chloropyridin-2-yl)methyl]-6-(2,2-difluoro-5-azaspiro[2.4]heptan-5-yl)purine; and
1-[2-tert-Butyl-9-[(3-chloropyridin-2-yl)methyl]purin-6-yl]-3-methylazetidin-3-ol.

10. A compound according to claim 1 selected from
2-tert-butyl-9-[(2-chlorophenyl)methyl]-6-(3,3-difluoropyrrolidin-1-yl)purine;
2-tert-butyl-9-[(2-chloro-4-fluorophenyl)methyl]-6-(3,3-difluoropyrrolidin-1-yl)purine;
2-tert-butyl-6-(3,3-difluoropyrrolidin-1-yl)-9-[[2-(trifluoromethyl)phenyl]methyl]purine;
2-tert-butyl-9-[(2-chloropyridin-3-yl)methyl]-6-(3,3-difluoropyrrolidin-1-yl)purine;
2-tert-butyl-6-(3,3-difluoropyrrolidin-1-yl)-9-(oxolan-3-yl)purine;
2-[2-tert-butyl-6-(3,3-difluoropyrrolidin-1-yl)purin-9-yl]-1-(2-chlorophenyl)ethanone;
2-tert-butyl-6-(3,3-difluoropyrrolidin-1-yl)-9-[(2-methylsulfonylphenyl)methyl]purine;
2-tert-butyl-9-[(3-chloropyridin-2-yl)methyl]-6-(3,3-difluoropyrrolidin-1-yl)purine;
2-tert-butyl-6-(3,3-difluoropyrrolidin-1-yl)-9-(2-pyridin-3-yl ethyl)purine;
1-[2-tert-butyl-9-[[2-(trifluoromethyl)phenyl]methyl]purin-6-yl]pyrrolidin-3-ol;
1-[2-tert-butyl-9-[(3-chloropyridin-2-yl)methyl]purin-6-yl]pyrrolidin-3-ol;
1-[2-tert-butyl-9-[(2-chloropyridin-3-yl)methyl]purin-6-yl]pyrrolidin-3-ol;
1-[2-tert-butyl-9-[(2-chloro-4-fluorophenyl)methyl]purin-6-yl]pyrrolidin-3-ol;
(3S)-1-[2-tert-butyl-9-[[2-(trifluoromethyl)phenyl]methyl]purin-6-yl]pyrrolidin-3-ol;
(3S)-1-[2-tert-butyl-9-[(3-chlorophenyl)methyl]purin-6-yl]pyrrolidin-3-ol;
(3S)-1-[2-tert-butyl-9-[(2-chloropyridin-3-yl)methyl]purin-6-yl]pyrrolidin-3-ol;
(3S)-1-[2-tert-butyl-9-[(2-chlorophenyl)methyl]purin-6-yl]pyrrolidin-3-ol;
9-[(2-chlorophenyl)methyl]-6-(3,3-difluoropyrrolidin-1-yl)-2-(2,2-dimethylpropoxy)purine;
6-(3,3-difluoropyrrolidin-1-yl)-2-(2,2-dimethylpropoxy)-9-[[2-(trifluoromethyl)phenyl]methyl]purine;
2-tert-Butyl-9-[(1-cyclopropyltetrazol-5-yl)methyl]-6-(3,3-difluoropyrrolidin-1-yl)purine;
[(2R)-1-[2-tert-Butyl-9-[(3-chloropyridin-2-yl)methyl]purin-6-yl]pyrrolidin-2-yl]methanol;
2-tert-Butyl-9-[(3-chloropyridin-2-yl)methyl]-6-(3,3-difluoroazetidin-1-yl)purine;
3-[2-tert-Butyl-9-[(3-chloropyridin-2-yl)methyl]purin-6-yl]-1,3-thiazolidine;
(2R)-1-[2-tert-Butyl-9-[(3-chloropyridin-2-yl)methyl]purin-6-yl]pyrrolidine-2-carbonitrile; and
1-[2-tert-butyl-9-[(3-chloropyridin-2-yl)methyl]purin-6-yl]-3-(trifluoromethyl)azetidin-3-ol.

11. A process for the preparation of a compound of claim 1, comprising the reaction of a compound of formula (A)

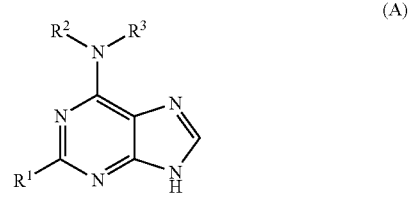

(A)

in the presence of Y-A-R$^4$
wherein Y is a leaving group selected from chlorine and bromine; A is selected from CH$_2$, CH$_2$CH$_2$, and CH$_2$CO; and R$^1$ to R$^4$ are as defined in claim 1.

12. A pharmaceutical composition comprising a compound of claim 1, and a therapeutically inert carrier.

13. A method for the treatment of pain, which method comprises administering an effective amount of a compound as defined in claim 1 to a patient in need thereof.

* * * * *